(12) United States Patent
Pongpeerapat et al.

(10) Patent No.: US 10,772,871 B2
(45) Date of Patent: *Sep. 15, 2020

(54) DEXMEDETOMIDINE TRANSDERMAL DELIVERY DEVICES AND METHODS FOR USING THE SAME

(71) Applicant: Teikoku Pharma USA, Inc., San Jose, CA (US)

(72) Inventors: Adchara Pongpeerapat, Gaithersburg, MD (US); Amit Jain, Milpitas, CA (US); Bret Berner, Seattle, WA (US); Jianye Wen, Palo Alto, CA (US); Jutaro Shudo, San Jose, CA (US)

(73) Assignee: Teikoku Pharma USA, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/505,930

(22) Filed: Oct. 3, 2014

(65) Prior Publication Data
US 2015/0098980 A1 Apr. 9, 2015

Related U.S. Application Data

(60) Provisional application No. 61/887,859, filed on Oct. 7, 2013.

(51) Int. Cl.
*A61K 47/14* (2017.01)
*A61K 9/70* (2006.01)
(Continued)

(52) U.S. Cl.
CPC ........ *A61K 31/4174* (2013.01); *A61K 9/7053* (2013.01); *A61K 9/7061* (2013.01);
(Continued)

(58) Field of Classification Search
CPC .......... A61K 31/4174; A61K 9/7038; A61K 9/7053; A61K 9/7061; A61K 47/12;
(Continued)

(56) References Cited

U.S. PATENT DOCUMENTS 4,544,664 A 10/1985 Karjalainen et al.
4,994,267 A 2/1991 Sablotsky
(Continued)

FOREIGN PATENT DOCUMENTS

CN 1994290 A 7/2007
DE 19938823 A1 2/2001
(Continued)

OTHER PUBLICATIONS

Hadgraft (Transdermal Drug Delivery Systems. CRC Press 2002 pp. 306, 307, 309 and 317).*
(Continued)

*Primary Examiner* — Ernst V Arnold
(74) *Attorney, Agent, or Firm* — Khin K. Chin; Bret E. Field; Bozicevic, Field & Francis LLP

(57) ABSTRACT

Aspects of the invention include transdermal delivery devices for delivering dexmedetomine to a subject, where the transdermal delivery devices include a single layer matrix dexmedetomine composition. Transdermal delivery devices according to certain embodiments include dexmedetomidine and a pressure sensitive adhesive provided as a single layer formulation. Also provide are methods of using the subject transdermal delivery devices to deliver dexmedetomidine to a subject, as well as kits containing the transdermal delivery devices.

21 Claims, 24 Drawing Sheets

(51) Int. Cl.
 *A61K 31/4174* (2006.01)
 *A61K 47/32* (2006.01)
 *A61K 47/12* (2006.01)
(52) U.S. Cl.
 CPC .............. *A61K 47/12* (2013.01); *A61K 47/14* (2013.01); *A61K 47/32* (2013.01)
(58) Field of Classification Search
 CPC ......... A61K 47/14; A61K 47/32; A61P 25/20; A61P 29/00
 See application file for complete search history.

(56) References Cited

U.S. PATENT DOCUMENTS

| | | | |
|---|---|---|---|
| 5,091,402 A | 2/1992 | Kalso et al. | |
| 5,124,157 A | 6/1992 | Colley et al. | |
| 5,176,916 A | 1/1993 | Yamanaka et al. | |
| 5,217,718 A | 6/1993 | Colley et al. | |
| 5,304,569 A | 4/1994 | Lammintausta et al. | |
| 5,352,456 A | 10/1994 | Fallon et al. | |
| 5,438,067 A | 8/1995 | Jalonen et al. | |
| 5,447,947 A | 9/1995 | Campbell | |
| 5,712,301 A | 1/1998 | Jaatinen et al. | |
| 5,817,332 A | 10/1998 | Uitti et al. | |
| 5,891,461 A | 4/1999 | Jona et al. | |
| 5,994,384 A | 11/1999 | Akerman et al. | |
| 6,071,531 A * | 6/2000 | Jona et al. ..................... | 424/449 |
| 6,329,369 B1 | 12/2001 | Chow et al. | |
| 6,562,363 B1 | 5/2003 | Mantelle et al. | |
| 6,689,379 B1 * | 2/2004 | Bracht ........................ | 424/448 |
| 7,001,609 B1 | 2/2006 | Matson et al. | |
| 7,097,853 B1 * | 8/2006 | Garbe ................... | A61K 9/7053 |
| | | | 424/448 |
| 7,838,563 B2 | 11/2010 | DeJovin et al. | |
| 8,017,146 B2 * | 9/2011 | Stefano ................ | A61K 9/7061 |
| | | | 424/447 |
| 8,114,898 B2 | 2/2012 | Shanler et al. | |
| 8,242,158 B1 | 8/2012 | Roychowdhury et al. | |
| 8,673,953 B2 | 3/2014 | Shanler et al. | |
| 2002/0016319 A1 | 2/2002 | Olney et al. | |
| 2002/0020600 A1 | 2/2002 | Reik et al. | |
| 2002/0068754 A1 | 6/2002 | Olney et al. | |
| 2002/0102291 A1 | 8/2002 | Mantelle et al. | |
| 2002/0177592 A1 | 11/2002 | Olney et al. | |
| 2003/0170195 A1 | 9/2003 | Houze et al. | |
| 2005/0020600 A1 | 1/2005 | Scherer | |
| 2005/0042173 A1 | 2/2005 | Besse et al. | |
| 2005/0042194 A1 | 2/2005 | Ng et al. | |
| 2005/0058696 A1 | 3/2005 | Donello et al. | |
| 2005/0059664 A1 | 3/2005 | Gil et al. | |
| 2006/0210613 A1 | 9/2006 | Carliss | |
| 2006/0240086 A1 | 10/2006 | Tateishi et al. | |
| 2006/0264515 A1 | 11/2006 | Dejovin et al. | |
| 2007/0098771 A1 * | 5/2007 | Audett ................. | A61K 9/7061 |
| | | | 424/449 |
| 2007/0134310 A1 | 6/2007 | Nedberge et al. | |
| 2007/0161543 A1 | 7/2007 | Yu et al. | |
| 2007/0207222 A1 | 9/2007 | Yu et al. | |
| 2009/0041832 A1 | 2/2009 | Govil et al. | |
| 2009/0098191 A1 | 4/2009 | Anderson et al. | |
| 2009/0130027 A1 | 5/2009 | Shanler et al. | |
| 2009/0258063 A1 | 10/2009 | Udagawa et al. | |
| 2009/0285877 A1 | 11/2009 | Yasukochi et al. | |
| 2010/0081669 A1 * | 4/2010 | Yang ................... | A61K 9/7061 |
| | | | 514/254.07 |
| 2010/0196286 A1 | 8/2010 | Armer et al. | |
| 2010/0197694 A1 | 8/2010 | Horn | |
| 2010/0202979 A1 | 8/2010 | Horn | |
| 2010/0305160 A1 | 12/2010 | Brummett | |
| 2011/0244058 A1 | 10/2011 | Horn | |
| 2011/0257188 A1 | 10/2011 | Horn | |
| 2011/0263542 A1 | 10/2011 | Gulati | |
| 2011/0264028 A1 | 10/2011 | Ramdas et al. | |
| 2012/0095104 A1 | 4/2012 | Zachar | |
| 2012/0202864 A1 | 8/2012 | Horn | |
| 2012/0309720 A1 | 12/2012 | Horn | |
| 2013/0072532 A1 | 3/2013 | Henwood et al. | |
| 2013/0172428 A1 | 7/2013 | Audett et al. | |
| 2013/0211351 A1 | 8/2013 | Fuhrherr et al. | |
| 2013/0237576 A1 | 9/2013 | Roychowdhury et al. | |
| 2013/0331803 A1 | 12/2013 | Fleschhut et al. | |
| 2014/0155446 A1 | 6/2014 | Roychowdhury et al. | |
| 2014/0343160 A1 * | 11/2014 | Govil ................... | A61K 9/7061 |
| | | | 514/654 |
| 2015/0044148 A1 | 2/2015 | Scherer | |
| 2015/0098982 A1 | 4/2015 | Pongpeerapat et al. | |

FOREIGN PATENT DOCUMENTS

| | | | |
|---|---|---|---|
| EA | 200501166 A1 | 2/2006 | |
| EA | 014504 B1 | 12/2010 | |
| EP | 0072615 B1 | 12/1985 | |
| EP | 0270267 A2 | 6/1988 | |
| EP | 413487 A1 | 2/1991 | |
| EP | 0187471 B1 | 7/1991 | |
| EP | 452837 A2 | 10/1991 | |
| EP | 0300652 B1 | 1/1992 | |
| EP | 0424059 B1 | 3/1993 | |
| EP | 0331374 B1 | 2/1994 | |
| EP | 0413487 B1 | 5/1995 | |
| EP | 0587819 B1 | 2/1997 | |
| EP | 0818470 A1 | 1/1998 | |
| EP | 1329225 A2 | 7/2003 | |
| EP | 0517850 B1 | 11/2003 | |
| EP | 1444977 * | 8/2004 | .............. A61K 9/70 |
| EP | 1227807 B1 | 3/2005 | |
| EP | 1069893 B1 | 12/2006 | |
| EP | 2165706 A1 | 3/2010 | |
| EP | 2363147 A1 | 9/2011 | |
| EP | 2370136 A1 | 10/2011 | |
| EP | 2395997 A1 | 12/2011 | |
| EP | 2429521 A2 | 3/2012 | |
| EP | 2481412 A1 | 8/2012 | |
| EP | 2481747 A1 | 8/2012 | |
| EP | 2521544 A2 | 11/2012 | |
| EP | 2696874 A2 | 2/2014 | |
| EP | 2815748 A1 | 12/2014 | |
| EP | 2890376 A1 | 7/2015 | |
| GB | 2290964 A | 1/1996 | |
| JP | S60163811 A | 8/1985 | |
| JP | H041127 A | 1/1992 | |
| JP | H05503916 A | 6/1993 | |
| JP | H06507888 A | 9/1994 | |
| JP | H776526 A | 3/1995 | |
| JP | 2007-505113 A | 3/2007 | |
| JP | 2011529490 A | 12/2011 | |
| JP | 2012-158521 A | 8/2012 | |
| KR | 10-2001-0075528 A | 8/2001 | |
| TW | 187070 | 7/1992 | |
| TW | 200732001 | 9/2007 | |
| TW | 200738645 | 10/2007 | |
| TW | 201332546 A | 8/2013 | |
| WO | WO9102505 A1 | 3/1991 | |
| WO | WO9307842 A1 | 4/1993 | |
| WO | WO9325199 A3 | 12/1993 | |
| WO | WO9601626 A1 | 1/1996 | |
| WO | WO-9610429 A2 * | 4/1996 | ........... A61K 9/7084 |
| WO | WO9949854 A2 | 10/1999 | |
| WO | WO0019987 A1 | 4/2000 | |
| WO | WO0023066 A2 | 4/2000 | |
| WO | WO0041681 A2 | 7/2000 | |
| WO | WO0076545 A1 | 12/2000 | |
| WO | WO0147512 A2 | 7/2001 | |
| WO | WO0189448 A2 | 11/2001 | |
| WO | WO2004032927 A1 | 4/2004 | |
| WO | WO2004080468 A1 | 9/2004 | |
| WO | WO2006034343 A2 | 3/2006 | |
| WO | WO2006074114 A2 | 7/2006 | |
| WO | WO2007050369 A1 | 5/2007 | |
| WO | WO2007085556 A2 | 8/2007 | |
| WO | WO2007100775 A2 | 9/2007 | |
| WO | WO2008059190 A1 | 5/2008 | |
| WO | WO2009124755 A1 | 10/2009 | |

(56) References Cited

FOREIGN PATENT DOCUMENTS

| WO | WO2010050211 | A1 |   | 5/2010 |   |
|---|---|---|---|---|---|
| WO | WO2010063030 | A2 |   | 6/2010 |   |
| WO | WO2010065547 | A1 |   | 6/2010 |   |
| WO | WO2010092312 | A1 |   | 8/2010 |   |
| WO | WO2011070069 | A1 |   | 6/2011 |   |
| WO | WO2011085162 | A2 |   | 7/2011 |   |
| WO | WO2011127586 | A1 |   | 10/2011 |   |
| WO | WO2011133212 | A1 |   | 10/2011 |   |
| WO | WO2012065740 | A1 |   | 5/2012 |   |
| WO | WO-2012097197 | A1 | * | 7/2012 | ........... A61K 31/445 |
| WO | WO2012142372 | A2 |   | 10/2012 |   |
| WO | WO2012144405 | A1 |   | 10/2012 |   |
| WO | WO2013055528 | A1 |   | 4/2013 |   |
| WO | WO2013072763 | A2 |   | 5/2013 |   |
| WO | WO2013090278 | A2 |   | 6/2013 |   |
| WO | WO2013173317 | A1 |   | 11/2013 |   |
| WO | WO2014035446 | A1 |   | 3/2014 |   |
| WO | WO2014076453 | A1 |   | 5/2014 |   |
| WO | WO2015093503 | A1 |   | 6/2015 |   |
| WO | WO2016105449 | A1 |   | 6/2016 |   |

OTHER PUBLICATIONS

Michaelis 2015 characterization of pressure sensitive adhesive systems 2 pages.*
Zhang et al. (AAPS PharmSciTech 2010, vol. 11(2):894-903) (Year: 2010).*
Baddigam et al., Dexmedetomidine in the treatment of withdrawal syndromes in cardiothoracic surgery patients, J Intensive Care Med (2005), 20(2):118-123.
Demuro et al., Use of dexmedetomidine for the treatment of alcohol withdrawal syndrome in critically ill patients: a retrospective case series, J Anesth (2012), 26(4):601-605.
Oschman et al., Dexmedetomidine for opioid and benzodiazepine withdrawal in pediatric patients, Am J Health Syst Pharm (2011), 68(13):1233-1238.
Finkel et al., The Use of Dexmedetomidine to Facilitate Opioid and Benzodiazepine Detoxification in an Infant, Anesth Analg ( 2004), 98(6):1658-1659.
Precedex® Dosing for Intensive Care Setting Sedation,www.precedex. com, 4 pages. 2014.
Ramsay, How to use the Ramsay Score to assess the level of ICU Sedation, Article, Conscious Sedation Consulting, 9 pages. 2014.
Smith et al., Alpha2 receptors and agonists in pain management, Current Opinion in Anaesthesiology (2001), 14:513-518.
Owens, A Clinical Overview of Sleep and Attention-Deficit/ Hyperactivity Disorder in Children and Adolescents, J Can Acad Child Adolesc Psychiatry (2009), 18(2): 92-102.
Kanwaljeet et al., Tolerance and Withdrawal From Prolonged Opioid Use in Critically Ill Children, Pediatrics (2010), 125(5): e1208-e1225.
Phan et al., Clinical uses of dexmedetomidine in pediatric patients, Paediatr Drugs. 2008;10(1):49-69.
Taghizadeh et al., A statistical experimental design approach to evaluate the influence of various penetration enhancers on transdermal drug delivery of buprenorphine, Journal of Advanced Research (2014), 6(2):155-162, Accepted manuscript.

Zhang et al., In vitro enhancement of lactate esters on the percutaneous penetration of drugs with different lipophilicity, AAPS PharmSciTech. Jun. 2010;11(2):894-903.
Huang et al., Topical/Transdermal Drug Delivery System for Natural Antioxidants: Resveratrol and Soy Isoflavones, Journal of Chang Gung Institute of Technology (2009), 11:1-10.
Li et al., Topical Delivery of Breviscapine-loaded Cataplasma, Journal of Liaoning University of TCM (2012), 14 (9):45-47.
Cheung et al., Analgesic and sedative effects of intranasal dexmedetomidine in third molar surgery under local anaesthesia, Br J Anaesth. Sep. 2011 ;107(3):430-7.
Kivistö et al., Pharmacokinetics and pharmacodynamics of transdermal dexmedetomidine, Eur J Clin Pharmacol. 1994;46(4):345-9.
Kamibayashi et al., Clinical uses of alpha2 -adrenergic agonists, Anesthesiology. Nov. 2000;93(5):1345-9.
Stern et al., Current approaches to the recognition and treatment of alcohol withdrawal and delirium tremens: "old wine in new bottles" or "new wine in old bottles", Prim Care Companion J Clin Psychiatry. 2010;12(3). pii: PCC.10r00991. doi: 10.4088/PCC. 10r00991ecr, 14 pages.
Maccioli, Dexmedetomidine to facilitate drug withdrawal, Anesthesiology. Feb. 2003;98(2):575-7.
Muzyk et al., Dexmedetomidine for the treatment of alcohol withdrawal syndrome: rationale and current status of research, CNS Drugs. Nov. 2013;27(11):913-20.
Hayashi et al., P1-2 Two Cases with Use of Dexmedetomidine (Precedex) for Palliative Care, Japanese Society for Palliative Medicine, Congress Program vol. 18, p. 368 (2013), English abstract enclosed.
Ebert et al., The effects of increasing plasma concentrations of dexmedetomidine in humans, Anesthesiology. Aug. 2000;93(2):382-94.
Tan et al., Pressure-sensitive adhesives for transdermal drug delivery systems, Pharm Sci Technolo Today. Feb. 1999;2(2):60-69.
Morrison et al., Organic Chemistry, Allyn and Bacon, Inc., 1959, p. 444.
Kim et al., Effect of vehicles and pressure sensitive adhesives on the permeation of tacrine across hairless mouse skin, Int J Pharm. Feb. 25, 2000;196(1):105-13.
Barry et al., Prevention of Surgical Oliguria and Renal-Hemodynamic Suppression by Sustained Hydration, The New England Journal of Medicine, 1964; 270:1371-1377.
Daniels et al., Efficacy and safety of oxycodone HCI/niacin tablets for the treatment of moderate-to-severe postoperative pain following bunionectomy surgery, Curr Med Res Opin. Mar. 2011;27(3):593-603, Abstract Only.
Soto et al., Analgesic effect of intra-articularly administered morphine, dexmedetomidine, or a morphine-combination immediately following stifle joint surgery in dogs, J Am Vet Med Assoc. Jun. 1, 2014;244(11):1291-7, Abstract Only.
Weinbroum et al., Dextromethorphan and Dexmedetomidine: New Agents for the Control of Perioperative Pain, Eur J Surg, Jul. 31, 2001, vol. 167, p. 563-569.
Tang et al., Dexmedetomidine in perioperative acute pain management: a non-opioid adjuvant analgesic, J Pain Res. Aug. 11, 2017;10:1899-1904.
Lundorf et al., Perioperative dexmedetomidine for acute pain after abdominal surgery in adults, Cochrane Database Syst Rev. Feb. 18, 2016;2:CD010358.

* cited by examiner

DEXMEDETOMIDINE TRANSDERMAL DELIVERY DEVICES AND METHODS FOR USING THE SAME

CROSS-REFERENCE TO RELATED APPLICATIONS

Pursuant to 35 U.S.C. § 119(e), this application claims priority to the filing date of U.S. Provisional Application Ser. No. 61/887,859 filed Oct. 7, 2013, the disclosure of which is herein incorporated by reference.

INTRODUCTION

Dexmedetomidine is the S-enantiomer of medetomidine and is an agonist of $\alpha_2$-adrenergic receptors that is used as a sedative medication in intensive care units and by anesthetists for intubated and nonintubated patients requiring sedation for surgery or short term procedures. The $\alpha_2$-adrenergic receptor is a G-protein coupled receptor associated with the $G_i$ heterotrimeric G-protein that includes three highly homologous subtypes, including $\alpha_{2a}$, $\alpha_{2b}$ and $\alpha_{2c}$-adrenergic receptors. Agonists of the $\alpha_2$-adrenergic receptor are implicated in sedation, muscle relaxation and analgesia through effects on the central nervous system.

Dexmedetomidine is used in clinical settings as a sedative through parenteral, intravenous and oral administration and thus, requires close supervision by a health care professional in a hospital setting. Dexmedetomidine is currently employed for sedation of intubated or mechanically ventilated subjects in an in-clinic (e.g., hospital) setting as well as for the sedation of non-intubated subjects as a part of monitored anesthesia during surgery, radiography or diagnostic procedures. Dexmedetomidine is also approved for continuous intravenous infusion in non-intubated subjects since it does not adversely affect breathing.

SUMMARY

Aspects of the invention include transdermal delivery devices for delivering dexmedetomine to a subject, where the transdermal delivery devices include a single layer matrix dexmedetomine composition. Transdermal delivery devices according to certain embodiments include dexmedetomidine and a pressure sensitive adhesive provided as a single layer formulation. Also provide are methods of using the subject transdermal delivery devices to deliver dexmedetomidine to a subject, as well as kits containing the transdermal delivery devices.

DETAILED DESCRIPTION

Figure 1:
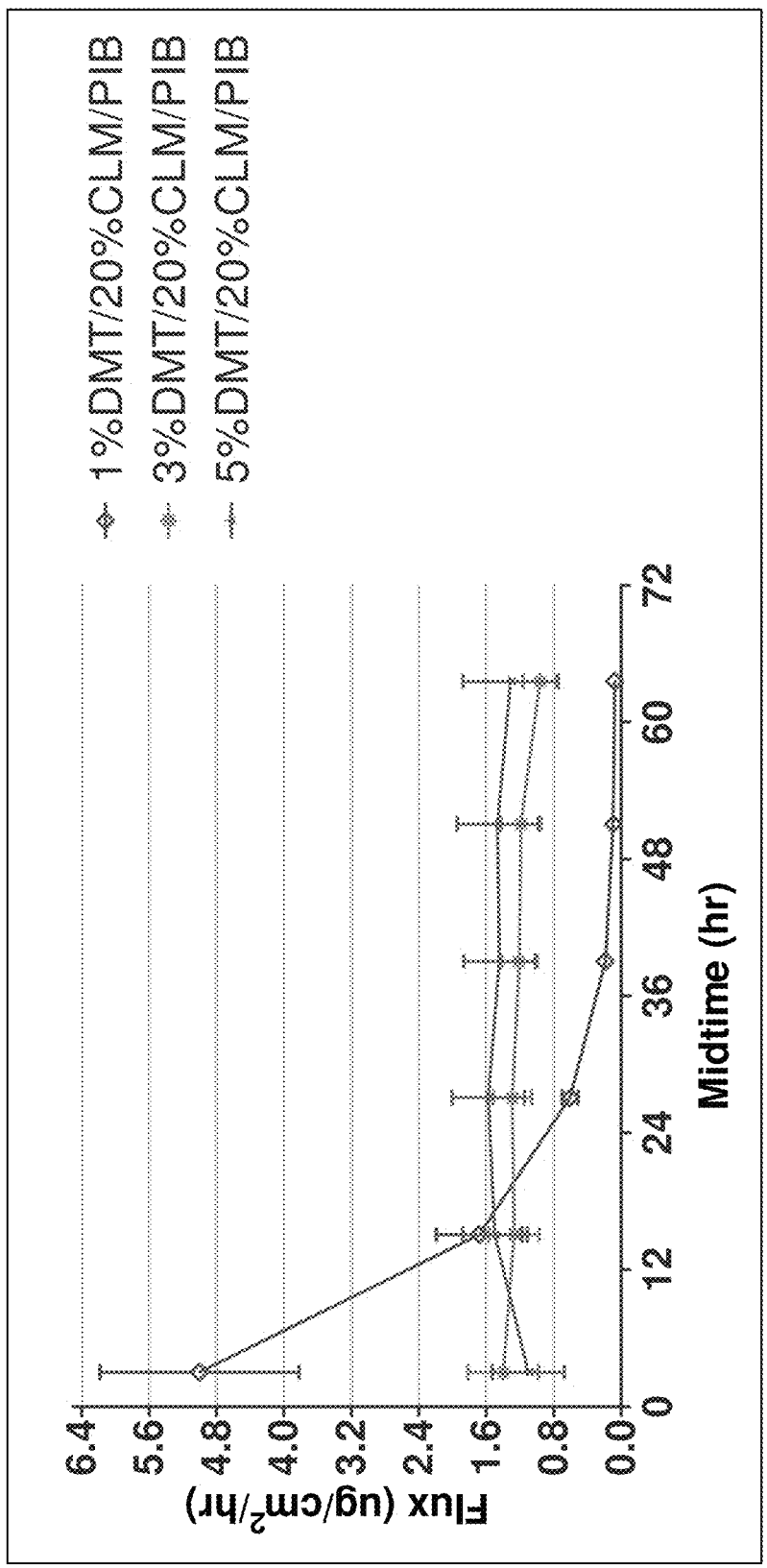
FIG. 1 shows an example of a plot of average dexmedetomidine flux as a function of transdermal delivery device application time for a dexmedetomidine transdermal composition with polyisobutylene/polybutene and crosslinked polyvinylpyrrolidone adhesive according to one embodiment.

Aspects of the invention include transdermal delivery devices for delivering dexmedetomine to a subject, where the transdermal delivery devices include a single layer matrix dexmedetomine composition. Transdermal delivery devices according to certain embodiments include dexmedetomidine and a pressure sensitive adhesive provided as a single layer formulation. Also provide are methods of using the subject transdermal delivery devices to deliver dexmedetomidine to a subject, as well as kits containing the transdermal delivery devices.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various embodiments of the invention, aspects of the transdermal delivery devices having a single layer matrix of a dexmedetomidine composition are reviewed first in greater detail, followed by a detailed description of embodiments of using the transdermal delivery systems to deliver dexmedetomidine to a subject and a review of kits that include the subject extended transdermal delivery devices.

Dexmedetomidine Transdermal Delivery Devices Containing a Single Layer Matrix Dexmedetomidine Composition As summarized above, aspects of the invention include dexmedetomidine transdermal delivery devices for delivering an amount of dexmedetomidine to a subject. The transdermal delivery devices include a single layer matrix composition having dexmedetomidine and a pressure sensitive adhesive. Dexmedetomidine is the S-enantiomer of medetomidine described by the formula:

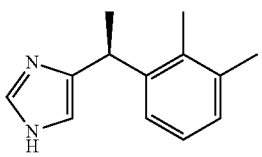

Dexmedetomidine according to embodiments of the invention may be in the form of a free base, salt, solvate, hydrate or complex. For example, dexmedetomidine may be in the form of a pharmaceutically acceptable salt including, but not limited to, a mesylate, maleate, fumarate, tartrate, hydrochloride, hydrobromide, esylate, p-toluenesulfonate, benzoate, acetate, phosphate and sulfate salt. Dexmedetomidine according to some embodiments may be a free base. In other instances, dexmedetomidine may form a complex.

In embodiments of the invention, the transdermal delivery device is configured with a single layer matrix dexmedetomidine composition. By "single layer" is meant that the transdermal delivery device includes only a single layer of dexmedetomidine composition disposed on the surface of a substrate of the transdermal delivery device and does not include separate distinct layers for the pressure sensitive adhesive, transdermal dexmedetomidine composition, or if present any solubility enhancers. Likewise, single layer transdermal delivery devices of the present invention do not further include a separate dexmedetomidine reservoir (i.e., active agent reservoir) separate from the pressure sensitive adhesive. As such, single layer transdermal delivery devices of the present invention may include in a single matrix an amount of each of the components of the transdermal dexmedetomidine compositions necessary for practicing the subject methods, as described in greater detail below. For example, in some embodiments, single layer transdermal delivery devices of interest include a single layer matrix of dexmedetomidine and a pressure sensitive adhesive which is configured to deliver a non-sedative amount of dexmedetomidine to a subject. In another embodiment, single layer transdermal delivery devices of interest include a single layer matrix of dexmedetomidine, a pressure sensitive adhesive and a solubility enhancer which is configured to deliver a non-sedative amount of dexmedetomidine to a subject. In another embodiment, single layer transdermal delivery devices of interest include a single layer matrix of dexmedetomidine, a pressure sensitive adhesive and a fatty acid ester which is configured to deliver a non-sedative amount of dexmedetomidine to a subject. In certain embodiments, single layer transdermal delivery devices of interest include a single layer matrix having only dexmedetomidine and a pressure sensitive adhesive. Depending on the length of the dosage interval and the desired target dosage, the thickness of single layer matrices of interest may vary, in some instances ranging in thickness from 10 to 260 microns, such as 15 to 250 microns, such as 25 to 225 microns, such as 50 to 200 microns, such as 75 to 175 microns and including 20 to 130 microns such as 35 to 110 microns.

Depending on the site of application and physiology of the subject (e.g., body mass), the amount of dexmedetomidine in compositions of interest may vary, in some instances, the amount of dexmedetomidine ranges from 0.001 mg to 50 mg, such as 0.005 mg to 40 mg, such as 0.01 to 30 mg, such as 0.05 to 20 mg, and including 0.1 mg to 10 mg. In some embodiments, the amount of dexmedetomidine in the transdermal composition ranges from 0.1% to 20% w/w, such as 0.5% to 18% w/w, such as 1% to 15%, such as 2% to 12.5% w/w and including 3% to 10% w/w. In other embodiments, the amount of dexmedetomidine in the subject transdermal compositions is 10% by weight or less of the total weight of the transdermal composition, such as 9% by weight or less, such as 8% by weight or less, such as 7% by weight or less, such as 6% by weight or less, such as 5% by weight or less and including 3% by weight or less of the total weight of the transdermal composition. In certain embodiments, dexmedetomidine compositions include an amount which is below the saturation point of dexmedetomidine. In other embodiments, dexmedetomidine compositions include a saturated amount of dexmedetomidine. In yet other embodiments, dexmedetomidine compositions include a supersaturated amount of dexmedetomidine.

In certain embodiments, dexmedetomidine compositions described herein are formulated to be non-sedative. By "non-sedative" is meant that the dexmedetomidine composition is formulated to deliver an amount of dexmedetomidine to the subject which does not cause complete sedation of the subject. In other words, a subject remains conscious and responsive throughout the entire time dexmedetomidine compositions of interest are transdermally administered to the subject. In certain instances, throughout administration of the dexmedetomidine transdermal composition, the subject remains in a cooperative, oriented and tranquil state. In other instances, throughout administration of the dexmedetomidine transdermal composition, the subject remains alert and capable of responding to commands (e.g., oral or written commands). In yet other instances, throughout administration of the dexmedetomidine transdermal composition, the subject is in an alert, cooperative, oriented and tranquil state and is capable of responding to commands (e.g., oral or written commands).

As described in greater detail below, in some embodiments dexmedetomidine transdermal compositions of interest are formulated such that throughout transdermal administration the subject may be evaluated according to the Ramsey Sedation Scale and assigned a Ramsey score of 4 or less, such as a Ramsey score of 3 or less, such as a Ramsey score of 2 or less and including where the subject is assigned a Ramsey score of 1. In certain instances, throughout administration of the dexmedetomidine transdermal composition, the subject exhibits brisk response to light glabellar tap or loud auditory stimulus. In other instances, throughout administration of the dexmedetomidine transdermal composition, the subject is responsive to oral commands. In yet other instances, throughout administration of the dexmedetomidine transdermal composition, the subject is cooperative, oriented and tranquil. In yet other instances, throughout administration of the dexmedetomidine transdermal composition, the subject is anxious, agitated or restless.

In embodiments of the present invention, transdermal dexmedetomidine compositions also include a pressure sensitive adhesive. Pressure sensitive adhesives may include, but are not limited to, poly-isobutene adhesives, polyisobutylene adhesives, poly-isobutene/polyisobutylene adhesive mixtures, carboxylated polymers, acrylic or acrylate copolymers, such as carboxylated acrylate copolymers.

Where the pressure sensitive adhesive includes polybutene, the polybutene may be saturated polybutene. Alternatively, the polybutene may be unsaturated polybutene. Still further, the polybutene may be a mixture or combination of saturated polybutene and unsaturated polybutene. In some embodiments, the pressure sensitive adhesive may include a composition that is, or is substantially the same as, the composition of Indopol® L-2, Indopol® L-3, Indopol® L-6, Indopol® L-8, Indopol® L-14, Indopol® H-7, Indopol® H-8, Indopol® H-15, Indopol® H-25, Indopol® H-35, Indopol® H-50, Indopol® H-100, Indopol® H-300, Indopol® H-1200, Indopol® H-1500, Indopol® H-1900, Indopol® H-2100, Indopol® H-6000, Indopol® H-18000, Panalane® L-14E, Panalane® H-300E and combinations thereof. In certain embodiments, the polybutene pressure-sensitive adhesive is Indopol® H-1900. In other embodiments, the polybutene pressure-sensitive adhesive is Panalane® H-300E.

Acrylate copolymers of interest include copolymers of various monomers, such as "soft" monomers, "hard" monomers or "functional" monomers. The acrylate copolymers can be composed of a copolymer including bipolymer (i.e., made with two monomers), a terpolymer (i.e., made with three monomers), or a tetrapolymer (i.e., made with four monomers), or copolymers having greater numbers of monomers. The acrylate copolymers may be crosslinked or non-crosslinked. The polymers can be cross-linked by known methods to provide the desired polymers. The monomers from of the acrylate copolymers may include at least two or more exemplary components selected from the group including acrylic acids, alkyl acrylates, methacrylates, copolymerizable secondary monomers or monomers with functional groups. Monomers ("soft" and "hard" monomers) may be methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989), the disclosure of which is herein incorporated by reference. In some embodiments, the pressure sensitive adhesive is an acrylate-vinyl acetate copolymer. In some embodiments, the pressure sensitive adhesive may include a composition that is, or is substantially the same as, the composition of Duro-Tak® 87-9301, Duro-Tak® 87-200A, Duro-Tak®87-2353, Duro-Tak®87-2100, Duro-Tak®87-2051, Duro-Tak®87-2052, Duro-Tak®87-2194, Duro-Tak®87-2677, Duro-Tak®87-201A, Duro-Tak®87-2979, Duro-Tak®87-2510, Duro-Tak®87-2516, Duro-Tak®87-387, Duro-Tak®87-4287, Duro-Tak®87-2287, and Duro-Tak®87-2074 and combinations thereof. The term "substantially the same" as used herein refers to a composition that is an acrylate-vinyl acetate copolymer in an organic solvent solution. In certain embodiments, the acrylic pressure-sensitive adhesive is Duro-Tak® 87-2054.

In certain embodiments, the pressure sensitive adhesive is an acrylate adhesive that is a non-functionalized acrylate, hydroxyl-functionalized acrylate or an acid functionalized acrylate. For example, the acrylate adhesive may be an acrylic adhesive having one or more —OH functional groups. Where the acrylic adhesive has one or more —OH functional groups, in some instances, the pressure sensitive adhesive may be a composition that is, or is substantially the same as, the composition of Duro-Tak® 87-4287, Duro-Tak® 87-2287, Duro-Tak® 87-2510 and Duro-Tak® 87-2516 and combinations thereof. The acrylate adhesive may alternatively be an acrylic adhesive having one or more —COOH functional groups. Where the acrylic adhesive has one or more —COOH functional groups, in some instances, the pressure sensitive adhesive may be a composition that is or is substantially the same as, the composition of Duro-Tak® 87-387, Duro-Tak® 87-2979 and Duro-Tak® 87-2353 and combinations thereof. Still further, the acrylate adhesive may be a non-functionalized acrylic adhesive. Where the acrylic adhesive is non-functionalized, in some instances the pressure sensitive adhesive may be a composition that is or is substantially the same as, the composition of Duro-Tak® 87-9301.

The amount of pressure sensitive adhesive in transdermal dexmedetomidine compositions of interest may vary, the amount of pressure sensitive adhesive ranging from 0.1 mg to 2000 mg, such as 0.5 mg to 1500 mg, such as 1 to 1000 mg, such as 10 to 750 mg, and including 10 mg to 500 mg. As such, the amount of pressure sensitive adhesive in the transdermal composition ranges from 1% to 99% w/w, such as 5% to 95% w/w, such as 10% to 95%, such as 15% to 90% w/w and including 20% to 85% w/w. In other embodiments, the amount of pressure sensitive adhesive in the subject transdermal compositions is 70% by weight or greater of the total weight of the transdermal composition, such as 75% by weight or greater, such as 80% by weight or greater, such as 85% by weight or greater, such as 90% by weight or greater, such as 95% by weight or greater and including 97% by weight or greater of the total weight of the transdermal composition.

The weight ratio of pressure sensitive adhesive to dexmedetomidine in the subject compositions may range from 1:2 and 1:2.5; 1:2.5 and 1:3; 1:3 and 1:3.5 1:3.5 and 1:4; 1:4 and 1:4.5; 1:4.5 and 1:5; 1:5 and 1:10; 1:10 and 1:25; 1:25 and 1:50; 1:50 and 1:75; and 1:75 and 1:99 or a range thereof. For example, the weight ratio of pressure sensitive adhesive to dexmedetomidine in compositions of interest may range between 1:1 and 1:5; 1:5 and 1:10; 1:10 and 1:15; 1:15 and 1:25; 1:25 and 1:50; 1:50 and 1:75 or 1:75 and 1:99. Alternatively, the weight ratio of dexmedetomidine to pressure sensitive adhesive in the subject compositions ranges between 2:1 and 2.5:1; 2.5:1 and 3:1; 3:1 and 3.5:1; 3.5:1 and 4:1; 4:1 and 4.5:1; 4.5:1 and 5:1; 5:1 and 10:1; 10:1 and 25:1; 25:1 and 50:1; 50:1 and 75:1; and 75:1 and 99:1 or a range thereof. For example, the ratio of dexmedetomidine to pressure sensitive adhesive in compositions of interest may range between 1:1 and 5:1; 5:1 and 10:1; 10:1 and 15:1; 15:1 and 25:1; 25:1 and 50:1; 50:1 and 75:1; or 75:1 and 99:1.

In some embodiments, transdermal dexmedetomidine compositions may further include one or more crosslinked hydrophilic polymers. For example, the crosslinked polymer may be an amine-containing hydrophilic polymer. Amine-containing polymers may include, but are not limited to, polyethyleneimine, amine-terminated polyethylene oxide, amine-terminated polyethylene/polypropylene oxide, polymers of dimethyl amino ethyl methacrylate, and copolymers of dimethyl amino ethyl methacrylate and vinyl pyrrolidone.

In certain embodiments, the crosslinked polymer is crosslinked polyvinylpyrrolidone, such as for example PVP-CLM.

The matrix may contain other additives depending on the adhesive used. For example, materials, such as PVP-CLM, PVP K17, PVP K30, PVP K90, that inhibit drug crystallization, have hygroscopic properties that improve the duration of wear, and improve the physical properties, e.g., cold flow, tack, cohesive strength, of the adhesive.

The amount of crosslinked polymer in dexmedetomidine compositions of interest may vary, the amount of crosslinked polymer ranging from 0.1 mg to 500 mg, such as 0.5 mg to 400 mg, such as 1 to 300 mg, such as 10 to 200 mg, and including 10 mg to 100 mg. As such, the amount of crosslinked polymer in the transdermal composition ranges from 2% to 30% w/w, such as 4% to 30% w/w, such as 5% to 25%, such as 6% to 22.5% w/w and including 10% to 20% w/w. In other embodiments, the amount of crosslinked polymer in the subject transdermal compositions is 8% by weight or greater of the total weight of the transdermal composition, such as 10% by weight or greater, such as 12% by weight or greater, such as 15% by weight or greater, such as 20% by weight or greater, such as 25% by weight or greater and including 30% by weight crosslinked polymer or greater of the total weight of the transdermal composition.

In certain embodiments, the subject transdermal dexmedetomidine compositions further include a dexmedetomidine solubility enhancer. By "solubility enhancer" is meant a compound or composition which increases the dexmedetomidine solubility in the subject compositions, such as, for example, to prevent any unwanted crystallization of dexmedetomidine in the composition. The dexmedetomidine solubilization enhancer is incorporated into the dexmedetomidine composition in an amount ranging from 0.01% to 20% (w/w), such as from 0.05% to 15% (w/w), such as from 0.1% to 10% (w/w), such as from 0.5% to 8% (w/w) and including from 1% to 5% (w/w).

Example solubility enhancers include, but are not limited to acids including linolic acid, oleic acid, linolenic acid, stearic acid, isostearic acid, levulinic acid, palmitic acid, octanoic acid, decanoic acid, dodecanoic acid, tetradecanoic acid, hexadecanoic acid, octadecanoic acid (i.e., stearic acid), N-lauroyl sarcosine, L-pyroglutamic acid, lauric acid, succinic acid, pyruvic acid, glutaric acid, sebacic acid, cyclopentane carboxylic acid; acylated amino acids. Other solubility enhancers of interest may include, but is not limited to aliphatic alcohols, such as saturated or unsaturated higher alcohols having 12 to 22 carbon atoms (e.g., oleyl alcohol or lauryl alcohol); fatty acid esters, such as isopropyl myristate, diisopropyl adipate, lauryl lactate, propyl laurate, ethyl oleate and isopropyl palmitate; alcohol amines, such as triethanolamine, triethanolamine hydrochloride, and diisopropanolamine; polyhydric alcohol alkyl ethers, such as alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, polypropylene glycolmonolaurate, sorbitan, sorbitol, isosorbide, methyl glucoside, oligosaccharides, and reducing oligosaccharides, where the number of carbon atoms of the alkyl group moiety in the polyhydric alcohol alkyl ethers is preferably 6 to 20; polyoxyethylene alkyl ethers, such as polyoxyethylene alkyl ethers in which the number of carbon atoms of the alkyl group moiety is 6 to 20, and the number of repeating units (e.g. —O—$CH_2CH_2$—) of the polyoxyethylene chain is 1 to 9, such as but not limited to polyoxyethylene lauryl ether, polyoxyethylene cetyl ether, polyoxyethylene stearyl ether, and polyoxyethylene oleyl ether; glycerides (i.e., fatty acid esters of glycerol), such as glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols; lactic acid alkyl esters; dibasic acid alkyl esters; acylated amino acids; pyrrolidone; pyrrolidone derivatives and combinations thereof. Additional types of solubility enhancers may include lactic acid, tartaric acid, 1,2,6-hexanetriol, benzyl alcohol, lanoline, potassium hydroxide (KOH), tris(hydroxymethyl)aminomethane, glycerol monooleate (GMO), sorbitan monolaurate (SML), sorbitan monooleate (SMO), laureth-4 (LTH), and combinations thereof. In certain embodiments, the solubility absorption enhancer is levulinic acid, lauryl lactate or propylene glycolmonolaurate.

The formulation of the subject transdermal dexmedetomidine composition may vary. For example, compositions of the invention may be in the form of a liquid solution or suspension, syrup, gel, foam or any combination thereof for application by the transdermal delivery device.

The size of subject transdermal delivery devices may vary, in some instances sized to cover the entire application site on the subject. As such, the transdermal delivery device may have a length ranging from 1 to 100 cm, such as from 1 to 60 cm and a width ranging from 1 to 100 cm, such as from 1 to 60 cm. As such, the area of the transdermal delivery device may range from 4 $cm^2$ to 10,000 $cm^2$, such as from 5 $cm^2$ to 1000 $cm^2$, such as from 10 $cm^2$ to 100 $cm^2$, such as from 15 $cm^2$ to 50 $cm^2$ and including from 20 $cm^2$ to 40 $cm^2$. In certain embodiments, the transdermal delivery device is sized to have an area of 30 $cm^2$. In certain instances, the transdermal delivery device is insoluble in water. By insoluble in water is meant that that the transdermal delivery device may be immersed in water for a period of 1 day or longer, such as 1 week or longer, including 1 month or longer, and exhibit little if any dissolution, e.g., no observable dissolution.

In certain embodiments, the transdermal delivery device as described above furthers includes an overlay backing layer. The overlay backing may be flexible, such as so that it can be brought into close contact with the desired application site on the subject. The overlay backing may be fabricated from a material that does not absorb the dexmedetomidine, and does not allow the dexmedetomidine to be leached from the matrix. Overlay backing layers of interest may include, but are not limited to, non-woven fabrics, woven fabrics, films (including sheets), porous bodies, foamed bodies, paper, composite materials obtained by laminating a film on a non-woven fabric or fabric, and combinations thereof.

Non-woven fabric may include polyolefin resins such as polyethylene and polypropylene; polyester resins such as polyethylene terephthalate, polybutylene terephthalate and polyethylene naphthalate; rayon, polyamide, poly(ester ether), polyurethane, polyacrylic resins, polyvinyl alcohol, styrene-isoprene-styrene copolymers, and styrene-ethylene-propylene-styrene copolymers; and combinations thereof. Fabrics may include cotton, rayon, polyacrylic resins, polyester resins, polyvinyl alcohol, and combinations thereof. Films may include polyolefin resins such as polyethylene and polypropylene; polyacrylic resins such as polymethyl methacrylate and polyethyl methacrylate; polyester resins such as polyethylene terephthalate, polybutylene terephthalate and polyethylene naphthalate; and besides cellophane, polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof. Papers may include impregnated paper, coated paper, wood free paper, Kraft paper, Japanese paper, glassine paper, synthetic paper, and combinations thereof.

Depending on the dosage interval and the desired target dosage, the size of the overlay backing may vary, and in some instances sized to cover the entire application site on the subject. As such, the backing layer may have a length ranging from 2 to 100 cm, such as 4 to 60 cm and a width ranging from 2 to 100 cm, such as 4 to 60 cm. In certain instances, the overlay backing layer may insoluble in water. By insoluble in water is meant that that the backing layer may be immersed in water for a period of 1 day or longer, such as 1 week or longer, including 1 month or longer, and exhibit little if any dissolution, e.g., no observable dissolution.

Transdermal delivery devices having a dexmedetomidine composition according to embodiments of the invention are non-irritable to the skin of the subject at the site of application. Irritation of the skin is referred to herein in its general sense to refer to adverse effects, discoloration or damage to the skin, such as for example, redness, pain, swelling or dryness. As such, in practicing methods with the subject transdermal delivery devices the quality of the skin remains normal and transdermal delivery is consistent throughout the entire dosage interval.

In some embodiments, skin irritation is evaluated to determine the quality and color of the skin at the application site and to determine whether any damage, pain, swelling or dryness has resulted from maintaining the transdermal composition in contact with the subject. The skin may be evaluated for irritation by any convenient protocol, such as for example using the Draize scale, as disclosed in Draize, J. H., *Appraisal of the Safety of Chemicals in Foods, Drugs and Cosmetics*, pp. 46-49, The Association of Food and Drug Officials of the United States: Austin, Tex., the disclosure of which is herein incorporated by reference. In particular, the skin may be evaluated at the transdermal application site for erythema or edema. For example, grades for erythema and edema may be assigned based on visual observation or palpation:

Erythema: 0=no visible redness; 1=very slight redness (just perceptible); 2=slight but defined redness; 3=moderately intense redness; 4=severe erythema (dark red discoloration of the skin) 5=eschar formation Edema: 0=no visible reactions or swelling; 1=very mild edema (just perceptible swelling); 2=mild edema (corners of area are well defined due to swelling); 3=moderate edema (up to 1 mm swelling); 4=severe edema (more than 1 mm swelling).

The site of application may be evaluated for skin irritation at any time during the subject methods. In some instances, the skin is evaluated for irritation while maintaining the transdermal delivery device in contact with the subject by observing or palpating the skin at regular intervals, e.g., every 0.25 hours, every 0.5 hours, every 1 hour, every 2 hours, every 4 hours, every 12 hours, every 24 hours, including every 72 hours, or some other interval. For instance, the site of application may be evaluated for skin irritation while maintaining the transdermal delivery device in contact with the subject, such as 15 minutes after applying the transdermal delivery device to the subject, 30 minutes after applying the transdermal delivery device, 1 hour after applying the transdermal delivery device, 2 hours after applying the transdermal delivery device, 4 hours after applying the transdermal delivery device, 8 hours after applying the transdermal delivery device, 12 hours after applying the transdermal delivery device, 24 hours after applying the transdermal delivery device, 48 hours after applying the transdermal delivery device, 72 hours after applying the transdermal delivery device, 76 hours after applying the transdermal delivery device, 80 hours after applying the transdermal delivery device, 84 hours after applying the transdermal delivery device, 96 hours after applying the transdermal delivery device, 120 hours after applying the transdermal delivery device, including 168 hours after applying the transdermal delivery device.

In other embodiments, the site of transdermal application is evaluated for skin irritation after the transdermal delivery device has been removed from contact with the subject. For example, the site of application may be evaluated for skin irritation 30 minutes after removing the transdermal delivery device, such as 1 hour after removing the transdermal delivery device, such as 2 hours after removing the transdermal delivery device, such as 4 hours after removing the transdermal delivery device, such as 8 hours after removing the transdermal delivery device, such as 12 hours after removing the transdermal delivery device, such as 24 hours after removing the transdermal delivery device, such as 48 hours after removing the transdermal delivery device, including 72 hours after removing the transdermal delivery device.

In some embodiments, the site of transdermal application is evaluated for skin irritation before the transdermal delivery device is applied to a subject, such as to record the skin color and texture before commencing a dosage interval. For example, the site of application may be evaluated for skin irritation 5 minutes before applying the transdermal delivery device, such as 10 minutes, such as 30 minutes, such as 60 minutes, such as 120 minutes, such as 240 minutes and including 480 minutes before applying the transdermal delivery device. Where methods include multiple dosage intervals applied sequentially, the site of application may be evaluated for skin irritation after each transdermal delivery device is removed and before the subsequent transdermal delivery device is applied. For example, when a first transdermal delivery device is removed, the site of application may be evaluated for skin irritation 2 hours, 24 hours and 48 hours after removal and before application of a second transdermal delivery device. A subsequent transdermal delivery device may be applied to the previous site of application immediately after evaluating the skin for irritation or may be applied after a predetermined time after evaluating the skin for irritation, such as 4 hours, 12 hours, 24 hours, 48 hours, 72 hours, 96 hours, 120 hours, 144 hours or 168 hours after evaluating the skin for irritation.

The site of application may be evaluated for skin irritation one or more times before, during or after a dosage interval, such as 2 or more times, such as 3 or more times, including 5 or more times before, during or after a dosage interval. An upper limit for the number of times the site of application may be evaluated for skin irritation before, during or after a dosage interval is, in some instances, 10 times or fewer, such as 7 times or fewer, such as 5 times or fewer, such as 3 times or fewer and including 2 times or fewer. In certain embodiments, the number of times the site of application may be evaluated for skin irritation before, during or after a dosage interval ranges such as from 2 times to 10 times, such as from 3 times to 9 times, such as from 4 times to 8 times and including from 5 times to 7 times. In certain embodiments, skin irritation may be monitored throughout the entire time the transdermal delivery device is maintained in contact with the subject, such by video monitoring.

Methods for Applying Transdermal Delivery Devices Having a Single Layer Dexmeditomidine Composition Aspects of the invention also include methods for applying to a subject, transdermal delivery devices having a single layer dexmedetomidine composition configured to deliver dexmedetomidine to the subject. The term "transdermal" is used in its conventional sense to refer to the route of administration where an active agent (i.e., drug) is delivered across the skin (e.g., topical administration) or mucous membrane for systemic distribution. As such, transdermal dexmedetomidine compositions as described herein include compositions which are delivered to the subject through one or more of the subcutis, dermis and epidermis, including the stratum corneum, stratum germinativum, stratum spinosum and stratum basale. Accordingly, extended transdermal delivery devices containing a transdermal dexmedetomidine composition may be applied at any convenient location, such as for example, the arms, legs, buttocks, abdomen, back, neck, scrotum, vagina, face, behind the ear, buccally as well as sublingually. In describing methods of the present invention, the term "subject" is meant the person or organism to which the transdermal composition is applied and maintained in contact. As such, subjects of the invention may include but are not limited to mammals, e.g., humans and other primates, such as chimpanzees and other apes and monkey species; and the like, where in certain embodiments the subject are humans. The term subject is also meant to include a person or organism of any age, weight or other physical characteristic, where the subjects may be an adult, a child, an infant or a newborn.

Transdermal administration of dexmedetomidine may be passive or active. By "passive" transport is meant that the dexmedetomidine composition is delivered across the skin or mucous membrane in the absence of applied energy (e.g., rubbing or heat) and is primarily dependent on the permeability of the barrier (e.g., skin or mucous membrane) and by entropy of delivery. However, transdermal administration according to certain embodiments may also include active transport of the dexmedetomidine composition across the skin or mucous membrane. Active transport can be any convenient protocol sufficient to transport the composition through the skin or mucous membrane in conjunction with applied energy and may include, but is not limited to microneedle delivery, facilitated diffusion, electrochemically-produced gradients, iontophoretic systems, among other protocols.

As described above, transdermal delivery devices having a single layer matrix dexmedetomidine composition include only one layer of the dexmedetomidine composition disposed on the surface of a substrate of the transdermal delivery device and does not include separate distinct layers for the pressure sensitive adhesive, dexmedetomidine composition, or if present any solubility enhancers, etc. As such, methods according to some embodiments include applying to a subject a transdermal delivery device having a single layer dexmedetomidine composition and maintaining the single layer dexmedetomidine composition in contact with the subject over a period of time sufficient to deliver dexmedetomidine to the subject.

In some embodiments, methods include extended transdermal delivery of dexmedetomidine to the subject. By "extended transdermal delivery" is meant that transdermal administration is formulated to provide for delivery of the dexmedetomidine composition over an extended period of time, such as over the course of hours, days and including weeks, including 1 hour or longer, such as 2 hours or longer, such as 4 hours or longer, such as 8 hours or longer, such as 12 hours or longer, such as 24 hours or longer, such as 48 hours or longer, such as 72 hours or longer, such as 96 hours or longer, such as 120 hours or longer, such as 144 hours or longer and including 168 hours or longer. For the above ranges an upper limit period of time is, in some instances, 168 hours or shorter, such as 144 hours or shorter, such as 120 hours or shorter, such as 96 hours or shorter, such as 72 hours or shorter, such as 48 hours or shorter and including 24 hours or shorter. In certain embodiments, extended transdermal delivery ranges such as from 0.5 hours to 168 hours, such as from 1 hour to 144 hours, such as from 1.5 hours to 120 hours, such from 2 hours to 96 hours, such as from 2.5 hours to 72 hours, such as from 3 hours to 48 hours, such as from 3.5 hours to 24 hours, such as from 4 hours to 12 hours and including from 5 hours to 8 hours.

In some embodiments, sustained release transdermal administration of the dexmedetomidine composition includes multi-day delivery of a therapeutically effective amount of the dexmedetomidine active agent that is applied to the skin of a subject. By multi-day delivery is meant that the transdermal composition is formulated to provide a therapeutically effective amount to a subject when the transdermal delivery device is applied to the skin of a subject for a period of time that is 1 day or longer, such as 2 days or longer, such as 4 days or longer, such as 7 days or longer, such as 14 days and including 30 days or longer. In certain embodiments, transdermal delivery devices provide a therapeutically effective amount of dexmedetomidine to a subject for a period of 10 days or longer. For multi-day delivery, an upper limit period of time is, in some instances, 30 days or shorter, such as 28 days or shorter, such as 21 days or shorter, such as 14 days or shorter, such as 7 days or shorter and including 3 days or shorter. In certain embodiments, multi-day transdermal delivery ranges such as from 2 days to 30 days, such as from 3 days to 28 days, such as from 4 days to 21 days, such as from 5 days to 14 days and including from 6 days to 10 days.

In certain embodiments, protocols may include multiple dosage intervals. By "multiple dosage intervals" is meant more than one transdermal delivery device is applied and maintained in contact with the subject in a sequential manner. As such, a transdermal delivery device is removed from contact with the subject and a new transdermal delivery device is reapplied to the subject. In practicing methods of the invention, treatment regimens may include two or more dosage intervals, such as three or more dosage intervals, such as four or more dosage intervals, such as five or more dosage intervals, including ten or more dosage intervals.

The duration between dosage intervals in a multiple dosage interval treatment protocol may vary, depending on the physiology of the subject or by the treatment protocol as determined by a health care professional. For example, the duration between dosage intervals in a multiple dosage treatment protocol may be predetermined and follow at regular intervals. As such, the time between dosage intervals may vary and may be 1 day or longer, such as 2 days or longer, such as 3 days or longer, such as 4 days or longer, such as 5 days or longer, such as 6 days or longer, such as 7 days or longer, such as 10 days or longer, including 30 days or longer. An upper limit period of time between dosage intervals is, in some instances, 30 days or shorter, such as 28 days or shorter, such as 21 days or shorter, such as 14 days or shorter, such as 7 days or shorter and including 3 days or shorter. In certain embodiments, the time between dosage intervals ranges such as from 2 days to 30 days, such as from 3 days to 28 days, such as from 4 days to 21 days, such as from 5 days to 14 days and including from 6 days to 10 days.

In certain instances, the duration between dosage intervals may depend on the plasma concentration of dexmedetomidine during the time the transdermal delivery device is not in contact with the subject between dosage intervals. For example, a subsequent dosage interval may commence when the plasma concentration of dexmedetomidine reaches below a particular threshold.

In certain embodiments, transdermal delivery devices provide a therapeutically effective amount of dexmedetomidine to a subject for a period of 10 days.

Methods for applying and maintaining a dexmedetomidine composition in contact with a subject according to methods of the present invention find use in any application where a subject would benefit from being transdermally administered dexmedetomidine, such as a malady, disease, ailment or condition that can be treated with the stimulation of α-adrenergic receptor agonist activity. For example, transdermal delivery devices having a single layer matrix dexmedetomidine composition may be employed according to certain embodiments to treat or manage pain syndromes, including neuropathic pain, idiopathic pain, acute pain, sympathetically mediated pain, complex regional pain, chronic pain, such as cancer pain, post-operative pain, post-herpetic neuralgia, irritable bowel syndrome and other visceral pain, diabetic neuropathy, pain associated with muscle spasticity, complex regional pain syndrome (CRPS), sympathetically maintained pain, headache pain including migraine headaches, allodynic pain, inflammatory pain, such as pain associated with arthritis, gastrointestinal pain, such as irritable bowel syndrome (IBS) and Crohn's disease, opioid addiction, attention deficit hyperactivity disorder and associated ailments such as restless legs syndrome, hypertension, Tourette's syndrome, depression and other psychiatric disorders such as schizophrenia and bipolar disorder, ocular hypertension, glaucoma, spasticity, atypical depression, panic disorder, social phobia, enuresis in children, obsessive-compulsive disorder, bulimia, narcolepsy, Parkinson's disease, Alzheimer's disease, amyotrophic lateral sclerosis and multiple sclerosis, ischemia, epilepsy, neuropathies such as diabetic and ischemic retinopathy, among other types of ailments and conditions where the subject will benefit from stimulation of α-adrenergic receptor agonist activity with a non-sedative amount of dexmedetomidine. In certain embodiments, transdermal delivery devices having a single layer dexmedetomidine composition may be employed according to embodiments of the invention to treat withdrawal syndrome such as opioid addiction. In other embodiments, transdermal delivery devices having a single layer dexmedetomidine composition may be employed to manage pain. In yet other embodiments, transdermal delivery devices having a single layer dexmedetomidine composition may be employed to treat attention deficit hyperactivity disorder or insomnia.

The term "treatment" is used herein in its conventional sense to mean that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely eliminated, such that the subject no longer suffers from the condition, or at least the symptoms that characterize the condition. The term "manage" is used herein in its conventional sense to mean that the symptoms associated with the condition afflicting the subject are at least kept under control (i.e., magnitude of the symptom are kept within a predetermined level), where in some instances the symptoms are ameliorated without eliminating the underlying condition.

In certain embodiments, compositions of the invention can be administered prior to, concurrent with, or subsequent to other therapeutic agents for treating the same or an unrelated condition. If provided at the same time as another therapeutic agent, the subject dexmedetomidine compositions may be administered in the same or in a different composition. Thus, dexmedetomidine compositions of interest and other therapeutic agents can be administered to the subject by way of concurrent therapy. By "concurrent therapy" is intended administration to a subject such that the therapeutic effect of the combination of the substances is caused in the subject undergoing therapy. For example, concurrent therapy may be achieved by administering dexmedetomidine compositions of the invention with a pharmaceutical composition having at least one other agent, such as an analgesic (such as an opioid), anesthetic, antihypertensive, chemotherapeutic, among other types of therapeutics, which in combination make up a therapeutically effective dose, according to a particular dosing regimen. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Where dexmedetomidine is administered concurrently with a second therapeutic agent to treat the same condition, the weight ratio of dexmedetomidine to second therapeutic agent may range from 1:2 and 1:2.5; 1:2.5 and 1:3; 1:3 and 1:3.5 1:3.5 and 1:4; 1:4 and 1:4.5; 1:4.5 and 1:5; 1:5 and 1:10; and 1:10 and 1:25 or a range thereof. For example, the weight ratio of dexmedetomidine to second therapeutic agent may range between 1:1 and 1:5; 1:5 and 1:10; 1:10 and 1:15; or 1:15 and 1:25. Alternatively, the weight ratio of the second therapeutic agent to dexmedetomidine ranges between 2:1 and 2.5:1; 2.5:1 and 3:1; 3:1 and 3.5:1; 3.5:1 and 4:1; 4:1 and 4.5:1; 4.5:1 and 5:1; 5:1 and 10:1; and 10:1 and 25:1 or a range thereof. For example, the ratio of the second therapeutic agent dexmedetomidine may range between 1:1 and 5:1; 5:1 and 10:1; 10:1 and 15:1; or 15:1 and 25:1.

Depending on the specific protocol employed and condition being treated, methods may include one or more dosage intervals. Dosage intervals may last about 0.5 hours or longer, such as 1 hour or longer, such as 2 hours or longer, such as 4 hours or longer, such as 8 hours or longer, such as 12 hours or longer, such as 16 hours or longer, such as 20 hours or longer, such as 24 hours or longer, such as about 48 hours or longer, such as about 72 hours or longer, such as 96 hours or longer, such as 120 hours or longer, such as 144 hours or longer and including about 168 hours or longer. An upper limit period of time for the duration of dosage intervals is, in some instances, 168 hours or shorter, such as 144 hours or shorter, such as 120 hours or shorter, such as 96 hours or shorter, such as 72 hours or shorter, such as 48 hours or shorter and including 24 hours or shorter. In certain embodiments, the duration of dosage intervals such as from 0.5 hours to 168 hours, such as from 1 hour to 144 hours, such as from 1.5 hours to 120 hours, such from 2 hours to 96 hours, such as from 2.5 hours to 72 hours, such as from 3 hours to 48 hours, such as from 3.5 hours to 24 hours, such as from 4 hours to 12 hours and including from 5 hours to 8 hours.

Treatment protocols may include one or more dosage intervals, as desired, such as two or more dosage intervals, such as five or more dosage intervals, including ten or more dosage intervals. Depending on the physiology of the subject and the desired therapeutic effect, the duration of dosage intervals and treatment protocols according to embodiments of the present invention may vary, as described below.

In certain embodiments, dexmedetomidine compositions described herein are formulated to be non-sedative. By "non-sedative" is meant that the dexmedetomidine composition is formulated to deliver an amount of dexmedetomidine to the subject which does not cause complete sedation of the subject. In other words, a subject remains conscious and responsive throughout the entire time dexmedetomidine is transdermally administered to the subject. In certain instances, throughout administration of the dexmedetomidine transdermal composition, the subject remains in a cooperative, oriented and tranquil state. In other instances, throughout administration of the dexmedetomidine transdermal composition, the subject remains alert and capable of responding to commands (e.g., oral or written commands). In yet other instances, throughout administration of the dexmedetomidine transdermal composition, the subject is in an alert, cooperative, oriented and tranquil state and is capable of responding to commands (e.g., oral or written commands).

Suitable protocols for determining level of sedation may include but are not limited to the Ramsay Sedation Scale, the Vancouver Sedative Recovery Scale, the Glasgow Coma Scale modified by Cook and Palma, the Comfort Scale, the New Sheffield Sedation Scale, the Sedation-Agitation Scale, and the Motor Activity Assessment Scale, among other convenient protocols for determining the level of sedation.

In some embodiments, subject methods (described in greater detail below) may further include evaluating the level of sedation of the subject to determine whether any reduction in responsiveness or cognitive or motor activity has resulted from administration of a transdermal delivery device formulated to deliver a non-sedative amount of dexmedetomidine. The level of sedation may be evaluated by any convenient protocol, such as with those mentioned above. In certain embodiments, the level of sedation is evaluated using the Ramsey Sedation Scale, (as disclosed in Ramsay, et al. Controlled sedation with alphaxalone-alphadolone, British Med Journal 1974; 2:656-659, the disclosure of which is herein incorporated by reference). For example, each subject may be evaluated by a qualified health care professional and assigned a score for the level of sedation according to the Ramsey Sedation Scale, summarized below.

Ramsay Sedation Scale

| Score | Description of Responsiveness, Cognitive and Motor Activity |
|---|---|
| 1 | Patient is anxious and agitated or restless, or both |
| 2 | Patient is co-operative, oriented, and tranquil |
| 3 | Patient responds to commands only |
| 4 | Patient exhibits brisk response to light glabellar tap or loud auditory stimulus |

-continued

| Score | Description of Responsiveness, Cognitive and Motor Activity |
|---|---|
| 5 | Patient exhibits a sluggish response to light glabellar tap or loud auditory stimulus |
| 6 | Patient exhibits no response |

In some embodiments, during administration of subject dexmedetomidine transdermal compositions the level of sedation of a subject is evaluated and the subject is assigned a Ramsey score of 4 or less, such as a Ramsey score of 3 or less, such as a Ramsey score of 2 or less and including where the subject is assigned a Ramsey score of 1. In certain instances, throughout administration of the dexmedetomidine transdermal composition, the subject exhibits brisk response to light glabellar tap or loud auditory stimulus. In other instances, throughout administration of the dexmedetomidine transdermal composition, the subject is responsive to oral commands. In yet other instances, throughout administration of the dexmedetomidine transdermal composition, the subject is co-operative, oriented and tranquil. In yet other instances, throughout administration of the dexmedetomidine transdermal composition, the subject is anxious, agitated or restless.

The level of sedation of a subject may be evaluated at any time during the methods. In some instances, the level of sedation is evaluated while maintaining the extended transdermal delivery device in contact with the subject at regular intervals, e.g., every 0.25 hours, every 0.5 hours, every 1 hour, every 2 hours, every 4 hours or some other interval. For instance, the level of sedation may be evaluated while maintaining the transdermal delivery device in contact with the subject, such as 15 minutes after applying the transdermal delivery device to the subject, 30 minutes after applying the transdermal delivery device, 1 hour after applying the transdermal delivery device, 2 hours after applying the transdermal delivery device, 4 hours after applying the transdermal delivery device including 8 hours after applying the transdermal delivery device.

The level of sedation of the subject may be evaluated one or more times during a dosage interval, such as 2 or more times, such as 3 or more times, including 5 or more times before, during or after a dosage interval. An upper limit for the number of times the subject may be evaluated during a dosage interval is, in some instances, 10 times or fewer, such as 7 times or fewer, such as 5 times or fewer, such as 3 times or fewer and including 2 times or fewer. In certain embodiments, the number of times the subject may be evaluated during a dosage interval ranges such as from 2 times to 10 times, such as from 3 times to 9 times, such as from 4 times to 8 times and including from 5 times to 7 times.

In certain embodiments, sedation level may be monitored throughout the entire time the transdermal delivery device is maintained in contact with the subject, such by heart rate monitors, breathing monitors or by visual observation, including with the aid of a video monitor.

In some embodiments, the subject being treated is in a non-sedated state and is awake, alert, oriented, coherent and capable of responding to oral or written commands including questions or requests. For example, the subject may be in a non-sedated state when administration commences. In other embodiments, the subject is in a non-sedated state when administration commences and remains in a non-sedated state throughout one or more dosage intervals (i.e. the period of time dexmedetomidine transdermal delivery devices of interest are maintained in contact with the subject). In yet other embodiments, the subject is in a non-sedated state when administration commences and remains in a non-sedated stated throughout the entire treatment protocol.

As described above, aspects of the invention include applying to a subject a transdermal delivery device having a single layer dexmedetomidine composition and maintaining the single layer dexmedetomidine composition in contact with the subject over a period of time sufficient to deliver dexmedetomidine to the subject. In some embodiments, methods include maintaining the transdermal delivery device in contact with a subject in a manner sufficient to deliver a target dosage of dexmedetomidine to the subject, such as for example delivering a target dosage as determined by total drug exposure or by average daily drug exposure. Depending on the desired therapeutic effect of the transdermal dexmedetomidine composition, the treatment protocol and the physiology of the subject, target drug exposure may vary. In certain embodiments, the target drug exposure of dexmedetomidine is an amount which is in the therapeutic window of the subject. In embodiments of the invention, a therapeutically effective amount provides for a systemic amount of dexmedetomidine that enables the desired treatment. For example, the target dosage of dexmedetomidine may range from 25 µg/day to 500 µg/day, such as from 50 µg/day to 475 µg/day, such as from 75 µg/day to 450 µg/day, such as from 100 µg/day to 425 µg/day, such as from 125 µg/day to 400 µg/day, such as from 150 µg/day to 375 µg/day, such as from 175 µg/day to 350 µg/day, such as from 200 µg/day to 325 µg/day and including from 200 µg/day to 300 µg/day over the course of a dosage interval (e.g., a 168 hour dosage interval). In certain embodiments, the target dosage of dexmedetomidine ranges from 147 µg/day to 290 µg/day over the course of a dosage interval (e.g., a 168 hour or longer dosage interval).

In some embodiments, the target dosage is an amount that provides for a systemic amount of dexmedetomidine that gives a desired mean plasma concentration of dexmedetomidine at specific times during treatment. In other embodiments, the target dosage is an amount that when applied to a subject provides for a steady state mean plasma concentration of the dexmedetomidine throughout a dosage interval or treatment protocol. In other embodiments, the target dosage is an amount that when applied to a subject provides for a particular rate of delivery of dexmedetomidine to the subject in vivo.

In some embodiments, applying and maintaining a transdermal delivery device containing a single layer dexmedetomidine composition in contact with a subject includes delivery of a target amount of dexmedetomidine, such as for example an average cumulative amount of dexmedetomidine delivered over the course of a dosage interval (e.g., 7 days or longer). The term "target cumulative amount" is meant the total quantity of dexmedetomidine which is delivered to the subject through the skin and may vary due to skin or mucous membrane permeability and metabolic activity of the site of application. In some embodiments, the average cumulative amount of dexmedetomidine may be 5 µg/cm$^2$ or greater, such as 25 µg/cm$^2$ or greater, such as 50 µg/cm$^2$ or greater over a 7 day delivery interval, such as 75 µg/cm$^2$ or greater, such as 100 µg/cm$^2$ or greater, such as 125 µg/cm$^2$ or greater and including 200 µg/cm$^2$ or greater over the dosage interval. For average cumulative amount of dexmedetomidine delivery over a dosage interval, an upper limit is, in some instances, 500 µg/cm$^2$ or less, such as 400 µg/cm$^2$ or less, such as 300 µg/cm$^2$ or less, such as 200 µg/cm$^2$ or less, such as 100 µg/cm$^2$ or less and including 50 µg/cm$^2$ or less. In certain embodiments, average cumulative amount of dexmedetomidine delivery over a dosage interval ranges such as from 5 µg/cm$^2$ to 500 µg/cm$^2$, such as from 25 µg/cm$^2$ to 400 µg/cm$^2$ and including from 50 µg/cm$^2$ to 300 µg/cm$^2$.

Methods according to certain embodiments may include applying to the subject a transdermal delivery device containing a single layer dexmedetomidine composition and maintaining the transdermal dexmedetomidine composition in contact with the subject in a manner sufficient to provide a mean plasma concentration which ranges from 0.05 ng/mL to 0.5 ng/mL over the course of a dosasge interval, such as from 0.1 ng/mL to 0.45 ng/mL, such as from 0.15 ng/mL to 0.4 ng/mL, such as from 0.2 ng/mL to 0.35 ng/mL and including from 0.25 ng/mL to 0.3 ng/mL. For example, the transdermal delivery device may be maintained in contact with the subject in a manner sufficient to provide a mean plasma concentration which ranges from 0.16 ng/mL to 0.36 ng/mL over the course of a dosage interval (e.g., a 168 hour or longer dosage interval). In other embodiments, methods include maintaining the single layer dexmedetomidine transdermal composition in contact with the subject in a manner sufficient to provide a mean plasma concentration which ranges from 0.05 ng/mL to 0.5 ng/mL over the course of the entire treatment protocol (i.e., over one or more dosage intervals), such as from 0.1 ng/mL to 0.45 ng/mL, such as from 0.15 ng/mL to 0.4 ng/mL, such as from 0.2 ng/mL to 0.35 ng/mL and including from 0.25 ng/mL to 0.3 ng/mL over the course of the entire treatment protocol. For example, the transdermal delivery device may be maintained in contact with the subject in a manner sufficient to provide a mean plasma concentration which ranges from 0.16 ng/mL to 0.36 ng/mL over the course of the entire treatment protocol.

In certain embodiments, methods may also include determining the plasma concentration of dexmedetomidine in the subject. The plasma concentration may be determined using any convenient protocol, such for example by liquid chromatography-mass spectrometry (LCMS). The plasma concentration of the dexmedetomidine may be determined at any time desired. In some embodiments, the plasma concentration of dexmedetomidine may be monitored throughout the entire time the transdermal delivery device is maintained in contact with the subject, such by real-time data collection. In other instances, the plasma concentration of dexmedetomidine is monitored while maintaining the transdermal delivery device in contact with the subject by collecting data at regular intervals, e.g., collecting data every 0.25 hours, every 0.5 hours, every 1 hour, every 2 hours, every 4 hours, every 12 hours, every 24 hours, including every 72 hours, or some other interval. In yet other instances, the plasma concentration of dexmedetomidine is monitored while maintaining the transdermal delivery device in contact with the subject by collecting data according to a particular time schedule after applying the transdermal delivery device to the subject. For instance, the plasma concentration of dexmedetomidine may be determined 15 minutes after applying the transdermal delivery device to the subject, 30 minutes after applying the transdermal delivery device to the subject, 1 hour after applying the transdermal delivery device to the subject, 2 hours after applying the transdermal delivery device to the subject, 4 hours after applying the transdermal delivery device to the subject, 8 hours after applying the transdermal delivery device to the subject, 12 hours after applying the transdermal delivery device to the subject, 24 hours after applying the transdermal delivery device to the subject, 48 hours after applying the transdermal delivery device to the subject, 72 hours after applying the transdermal delivery device to the subject, 76 hours after applying the transdermal delivery device to the subject, 80 hours after applying the transdermal delivery device to the subject, 84 hours after applying the transdermal delivery device to the subject, 96 hours after applying the transdermal delivery device to the subject, 120 hours after applying the transdermal delivery device to the subject and including 168 hours after applying the transdermal delivery device to the subject.

In certain embodiments, the plasma concentration of dexmedetomidine is determined before the transdermal delivery device is applied to a subject, such as for example, to determine the basal plasma concentration of the dexmedetomidine. For example, the plasma concentration may be determined 5 minutes before applying the transdermal delivery device, such as 10 minutes before, such as 30 minutes before, such as 60 minutes before, such as 120 minutes before, such as 240 minutes before and including 480 minutes before applying the transdermal delivery device. As described detail below, methods may include multiple dosage intervals where applying and maintaining the transdermal delivery device in contact with the subject may be repeated. In these embodiments, the plasma concentration may be determined after a first transdermal delivery device is removed and before a second transdermal delivery device is applied.

The blood plasma concentration of the dexmedetomidine may be determined one or more times at any given measurement period, such as 2 or more times, such as 3 or more times, including 5 or more times at each measurement period. An upper limit for the number of times the blood plasma concentration of dexmedetomidine is determined at any given measurement period is, in some instances, 10 times or fewer, such as 7 times or fewer, such as 5 times or fewer, such as 3 times or fewer and including 2 times or fewer. In certain embodiments, the number of times the blood plasma concentration of dexmedetomidine is determined at any given measurement period ranges such as from 2 times to 10 times, such as from 3 times to 9 times, such as from 4 times to 8 times and including from 5 times to 7 times.

Methods according to certain embodiments may include applying to the subject a transdermal delivery device containing a single layer dexmedetomidine composition and maintaining the transdermal dexmedetomidine composition in contact with the subject in a manner sufficient to maintain a transdermal dexmedetomidine flux which is within 30% or more of the peak transdermal dexmedetomidine flux after reaching the peak transdermal flux. As such, once transdermal delivery devices of interest reach peak transdermal dexmedetomidine flux, the transdermal delivery device is configured to maintain a flux of dexmedetomidine to the subject that is at least 30% of peak flux during the course of any given dosage interval, such as at least 35%, such as at least 40% and including at least 50% of peak flux during the course of any given dosage interval. In other words, once peak flux is reached by the transdermal delivery device according to these particular embodiments, the transdermal flux of dexmedetomidine to the subject does not fall below 30% or more of the peak flux at any time during the dosage interval.

For example, the single layer transdermal dexmedetomidine composition may be maintained in contact with the subject in a manner sufficient to maintain the transdermal dexmedetomidine flux which is within 80% or more of peak transdermal flux, such as within 85% or more, such as within 90% or more, such as within 95% and including within 99% of peak transdermal dexmedetomidine flux after reaching peak transdermal flux. In certain embodiments, the transdermal dexmedetomidine flux does not decrease at all after reaching peak flux and maintains a rate of 100% of peak dexmedetomidine flux from the moment it reaches peak flux until the end of a given dosage interval.

The flux of an active agent by transdermal administration is the rate of penetration of the active agent through the skin or mucous membrane of the subject. In some instances, the flux of the dexmedetomidine can be determined by the equation:

$$J_{skin\,flux} = P \times C \qquad (1)$$

where J is the skin flux, C is the concentration gradient across the skin or mucous membrane and P is the permeability coefficient. Skin flux is the change in cumulative amount of drug entering the body across the skin or mucous membrane with respect to time.

In some instances, the single layer transdermal dexmedetomidine composition is maintained in contact with the subject in a manner sufficient to provide a peak flux of 0.05 µg/cm$^2$/hr or greater, such as 0.1 µg/cm$^2$/hr or greater, such as 0.5 µg/cm$^2$/hr or greater, such as 1 µg/cm$^2$/hr, such as 2 µg/cm$^2$/hr, such as 3 µg/cm$^2$/hr or greater, such as 5 µg/cm$^2$/hr or greater, such as 7.5 µg/cm$^2$/hr or greater and including maintaining the single layer transdermal dexmedetomidine composition in contact with the subject in a manner sufficient to provide a peak flux of 10 µg/cm$^2$/hr or greater. For peak flux of transdermal dexmedetomidine delivery, an upper limit is, in some instances, 10 µg/cm$^2$/hr or less, such as 9 µg/cm$^2$/hr or or less, such as 8 µg/cm$^2$/hr or less, such as 7 µg/cm$^2$/hr or less, 6 µg/cm$^2$/hr or or less, such as 5 µg/cm$^2$/hr or less and including 2 µg/cm$^2$/hr or less. In certain embodiments, the peak flux of transdermal dexmedetomidine delivery ranges such as from 0.05 µg/cm$^2$/hr to 10 µg/cm$^2$/hr, such as from 1 µg/cm$^2$/hr to 9 g/cm$^2$/hr and including from 2 µg/cm$^2$/hr to 8 µg/cm$^2$/hr.

As such, where the single layer transdermal dexmedetomidine composition is maintained in contact with the subject in a manner sufficient to provide a transdermal dexmedetomidine flux which is within at least 30% of peak transdermal dexmedetomidine flux, the single layer transdermal composition may be maintained in contact with the subject in a manner sufficient to provide a flux which is 0.15 µg/cm$^2$/hr or greater after reaching a peak transdermal flux of 0.5 µg/cm$^2$/hr, such as 0.18 µg/cm$^2$/hr or greater after reaching a peak transdermal flux of 0.6 µg/cm$^2$/hr, such as 0.225 µg/cm$^2$/hr or greater after reaching a peak transdermal flux of 0.75 µg/cm$^2$/hr, such as 0.27 µg/cm$^2$/hr or greater after reaching a peak flux of 0.9 µg/cm$^2$/hr, such as 0.3 µg/cm$^2$/hr or greater after reaching a peak flux of 1.0 µg/cm$^2$/hr, such as 1.5 µg/cm$^2$/hr after reaching a peak flux of 5 µg/cm$^2$/hr or greater and including maintaining the single layer transdermal dexmedetomidine composition in contact with the subject in a manner sufficient to provide a flux which is 3.0 µg/cm$^2$/hr or greater after reaching a peak flux of 10.0 µg/cm$^2$/hr.

Depending on the amount of dexmedetomidine present in the single layer transdermal composition, the physiology of the subject, target site of application, the time required to reach peak dexmedetomidine flux may vary. In some instances, peak dexmedetomidine flux is reached 2 hours or more after applying the transdermal delivery device to the subject, such as 4 hours or more, such as 6 hours or more, such as 12 hours or more, such as 18 hours or more and including at 24 hours or more after applying the transdermal delivery device to the subject. In other instances, the peak dexmedetomidine flux is reached at 168 hours or earlier, such as 144 hours or earlier, such as 120 hours or earlier, such as 96 hours or earlier, such as 72 hours or earlier, such as 48 hours or earlier, such as 24 hours or earlier, such as 12 hours or earlier, such as 8 hours earlier, such as 4 hours or earlier and including at 2 hours or earlier. In some embodiments, peak dexmedetomidine flux is reached at 24 hours after applying the transdermal delivery device to the subject.

In certain embodiments, the single layer transdermal composition is maintained in contact with the subject sufficient to provide a steady state average flux of dexmedetomidine to the subject. As such, the dexmedetomidine flux from transdermal delivery devices of interest increases or decreases by 30% or less at any time while the transdermal delivery device is maintained in contact with the subject, such as 20% or less, such as 15% or less, such as 12% or less, such as 10% or less, such as 6% or less, such as 5% or less, such as 4% or less, and including 1% or less at any time while the transdermal delivery device is maintained in contact with the subject.

Where the single layer dexmedetomidine transdermal composition is maintained in contact with the subject sufficient to provide a steady state average flux of dexmedetomidine, the steady state average dexmedetomidine flux may be maintained from for 0.5 hours or longer, such as 1 hour or longer, such as 2 hours or longer, such as 3 hours or longer, such as 4 hours or longer, such as 8 hours or longer, 12 hours or longer, such as 24 hours or longer, such as 36 hours or longer, such as 48 hours or longer, such as 72 hours or longer, such as 96 hours or longer, such as 120 hours or longer, such as 144 hours or longer and including 168 hours or longer. For maintaining a steady state average dexmedetomidine flux, an upper limit is, in some instances, for 168 hours or shorter, such as 144 hours or shorter, such as 120 hours or shorter, such as 96 hours or shorter, such as 72 hours or shorter, such as 48 hours or shorter, such as 24 hours or shorter, such as 12 hours or shorter, such as 8 hours or shorter, such as 4 hours or shorter and including 2 hours or shorter. In these embodiments, the transdermal delivery device is configured to provide a constant flux, such as by introducing a concentration gradient across the skin or mucous membrane or providing an excess in dexmedetomidine dosage amount. For example, single layer dexmedetomidine transdermal compositions may include a dexmedetomidine dosage that is 5% or greater in excess of the normal dosage amount, such as 10% or greater, such as 15% or greater, such as 20% or greater, and including 25% or greater in excess of the normal dosage amount. For amount of excess dexmedetomidine present in the transdermal delivery device to provide a constant flux, an upper limit is, in some instances 50% or less in excess, such as 45% or less in excess, such as 25% or less in excess, such as 20% or less in excess and including 10% or less in excess of the normal dosage amount. While single layer dexmedetomidine transdermal compositions may include an excess in order to provide a constant flux, the excess dosage amount is not absorbed as part of the dosage interval. As such, in some embodiments where the single layer transdermal dexmedetomidine composition is maintained in a manner sufficient to provide a constant flux, 25% or less of the available dexmedetomidine in the transdermal composition may not be utilized, such as 20% or less, such as 15% or less, such as 10% or less, such as 5% or less and including 1% or less of the available dexmedetomidine in the transdermal composition may not be utilized during the dosage interval.

Methods according to certain embodiments may include applying to the subject a transdermal delivery device containing a single layer dexmedetomidine composition and maintaining the transdermal dexmedetomidine composition in contact with the subject in a manner sufficient to provide an average flux of dexmedetomidine in vivo of from about 0.005 to about 5 $\mu g/cm^2 \cdot hr$, such as from about 0.01 to about 4 $\mu g/cm^2 \cdot hr$, such as from about 0.02 to about 3 $\mu g/cm^2 \cdot hr$, such as from about 0.05 to about 2.5 $\mu g/cm^2 \cdot hr$, such as from about 0.1 to about 2 $\mu g/cm^2 \cdot hr$ and including from about 0.1 to about 1 $\mu g/cm^2 \cdot hr$ at any time after applying the transdermal delivery device. In some embodiments, methods include applying the single layer transdermal dexmedetomidine composition to the subject and maintaining the single layer transdermal composition in contact with the subject in a manner sufficient to provide an average flux of dexmedetomidine in vivo of from about 0.005 to about 2.0 $\mu g/cm^2 \cdot hr$ at 24 hours after application, such as from about 0.01 to about 1.75 $\mu g/cm^2 \cdot hr$, such as from about 0.02 to about 1.5 $\mu g/cm^2 \cdot hr$, such as from about 0.05 to about 1.25 $\mu g/cm^2 \cdot hr$ and including from about 0.1 to about 1 $\mu g/cm^2 \cdot hr$ at 24 hours after application. In yet other embodiments, methods include applying the single layer transdermal dexmedetomidine composition to the subject and maintaining the single layer transdermal composition in contact with the subject in a manner sufficient to provide an average flux of dexmedetomidine in vivo of from about 0.005 to about 2.0 $\mu g/cm^2 \cdot hr$ at 168 hours after application, such as from about 0.01 to about 1.75 $\mu g/cm^2 \cdot hr$, such as from about 0.02 to about 1.5 $\mu g/cm^2 \cdot hr$, such as from about 0.05 to about 1.25 $\mu g/cm^2 \cdot hr$ and including from about 0.1 to about 1 $\mu g/cm^2 \cdot hr$ at 168 hours after application.

In certain embodiments, methods include determining the transdermal dexmedetomidine flux. The transdermal dexmedetomidine flux may be determined using any convenient protocol, such for example by protocols employing human cadaver skin with epidermal layers (stratum corneum and epidermis) in a Franz cell having donor and receptor sides clamped together and receptor solution containing phosphate buffer. The amount of permeated dexmedetomidine can further be characterized by liquid chromatography. The transdermal dexmedetomidine flux may be determined at any time during methods of the invention. In some embodiments, the transdermal dexmedetomidine flux may be monitored throughout the entire time the single layer transdermal dexmedetomidine composition is maintained in contact with the permeation barrier (e.g., human cadaver skin), such by real-time data collection. In other instances, the transdermal dexmedetomidine flux is monitored by collecting data at regular intervals, e.g., collecting data every 0.25 hours, every 0.5 hours, every 1 hour, every 2 hours, every 4 hours, every 12 hours, every 24 hours, including every 72 hours, or some other regular or irregular intervals. In yet other instances, the transdermal dexmedetomidine flux is monitored by collecting data according to a particular time schedule. For instance, the transdermal dexmedetomidine flux may be determined 15 minutes after applying the transdermal delivery device, 30 minutes after applying the transdermal delivery device, 1 hour after applying the transdermal delivery device, 2 hours after applying the transdermal delivery device, 4 hours after applying the transdermal delivery device, 8 hours after applying the transdermal delivery device, 12 hours after applying the transdermal delivery device, 24 hours after applying the transdermal delivery device, 48 hours after applying the transdermal delivery device, 72 hours after applying the transdermal delivery device, 76 hours after applying the transdermal delivery device, 80 hours after applying the transdermal delivery device, 84 hours after applying the transdermal delivery device, 96 hours after applying the transdermal delivery device, 120 hours after applying the transdermal delivery device and including 168 hours after applying the transdermal delivery device.

The transdermal dexmedetomidine flux may be determined one or more times at any given measurement period, such as 2 or more times, such as 3 or more times, including 5 or more times at each measurement period. An upper limit for the number of times the transdermal dexmedetomidine flux is determined is, in some instances, 10 times or fewer, such as 7 times or fewer, such as 5 times or fewer, such as 3 times or fewer and including 2 times or fewer. In certain embodiments, the number of times the transdermal dexmedetomidine flux is determined ranges such as from 2 times to 10 times, such as from 3 times to 9 times, such as from 4 times to 8 times and including from 5 times to 7 times.

In some embodiments, in maintaining the single layer dexmedetomidine transdermal composition in contact with the subject the average cumulative amount of permeated dexmedetomidine increases at a substantially linear rate over the course of the dosage interval (e.g., 7 days or longer). By "substantially linearly" is meant that the cumulative amount of dexmedetomidine released from the single layer transdermal composition increases at a substantially constant rate (i.e., defined by zero-order kinetics). As such, the change in rate of cumulative permeated dexmedetomidine increases or decreases by 10% or less at any given time while maintaining the transdermal composition in contact with the subject, such as 8% or less, such as 7% or less, such as 6% or less, such as 5% or less, such as 3% or less, such as 2.5% or less, such as 2% or less, and including 1% or less at any time while maintaining the single layer dexmedetomidine transdermal composition in contact with the subject.

As described above, aspects of the invention include applying to a subject a transdermal delivery device having a single layer dexmedetomidine composition and maintaining the single layer dexmedetomidine composition in contact with the subject over a period of time sufficient to deliver dexmedetomidine to the subject. In some embodiments, methods may include maintaining the single layer dexmedetomidine transdermal composition in contact with the subject in a manner sufficient to deliver a predetermined amount of dexmedetomidine to the subject. Where protocols include delivering a predetermined amount of dexmedetomidine to the subject, the amount of dexmedetomidine in single layer compositions of interest may range from 0.001 mg to 50 mg, such as 0.005 to 40 mg, such as 0.01 mg to 30 mg, such as 0.05 to 20 mg, such as 0.1 mg to 15 mg, such as 0.5 mg to 12.5 mg and including from 0.5 mg to 10 mg.

In certain embodiments, the predetermined amount of dexmedetomidine delivered to the subject may be a percentage of the total amount of dexmedetomidine present in the single layer compositions. For instance, the predetermined amount of dexmedetomidine delivered to the subject may be 1% or greater of the total amount of dexmedetomidine present in the single layer composition, such as 2% or greater, such as 5% or greater, such as 10% or greater, such as 25% or greater and including 50% or greater of the total amount of dexmedetomidine present in the single layer composition. In other words, methods may include maintaining the single layer dexmedetomidine transdermal composition in contact with the subject in a manner sufficient to deliver 5% or greater of the dexmedetomidine in the single layer dexmedetomidine composition to the subject over the course of a single dosage interval. In these embodiments, the utilization percentage of dexmedetomidine is 5% or greater during the time the transdermal delivery device is maintained in contact with the subject. As such, 95% or less of the original amount of dexmedetomidine remains in the single layer transdermal dexmedetomidine composition after a dosage interval. As described in greater detail below, the subject transdermal delivery devices are capable of high utilization percentage. In other words, the subject transdermal delivery devices are capable of delivering dexmedetomidine to the subject leaving little residual dexmedetomidine in the transdermal delivery device after a given dosage interval. The utilization percentage may be 5% or greater over the course of a dosage interval, such as 10% or greater, such as 25% or greater, such as 40% or greater, such as 45% or greater and including 50% or greater of the dexmedetomidine over the course of a dosage interval. For utilization percentage, an upper limit over the course of a dosage interval is, in some instances, 90% or less, such as 50% or less, such as 25% or less and including 5% or less over the course of a dosage interval.

For instance, where the single layer transdermal dexmedetomidine composition contains 1 mg of dexmedetomidine, methods may include maintaining the transdermal delivery device in contact with the subject in a manner sufficient to deliver 0.05 mg or more of dexmedetomidine in the single layer transdermal composition over the course of the dosage interval (e.g., 7 days or longer), such as 0.1 mg or more, such as 0.25 mg or more, such as 0.4 mg or more, such as 0.45 mg or more and including maintaining the transdermal delivery device in contact with the subject in a manner sufficient to deliver 0.5 mg or more of dexmedetomidine in the single layer transdermal composition. As such, 0.95 mg or less of dexmedetomidine remains in the single layer transdermal dexmedetomidine composition after 7 days or longer, such as 0.9 mg or less, such as 0.75 mg or less, such as 0.6 mg or less and including 0.5 mg or less of dexmedetomidine remains in the single layer transdermal dexmedetomidine composition after the dosage interval.

In certain embodiments, each of the subject methods described in greater detail below may further include the step of removing the transdermal delivery device from contact with the subject at the conclusion of a dosage interval. For example, the transdermal delivery device may be removed from contact with the subject after maintaining the transdermal delivery device in contact with the subject for 0.5 hours or more, such as 1 hour or more, such as 2 hours or more, such as 4 hours or more, such as 8 hours or more, such as 12 hours or more, such as 24 hours or more, such as 36 hours or more, such as 48 hours or more, such as 60 hours or more, such as 72 hours or more, such as 96 hours or more, such as 120 hours or more, including 144 hours or more, and including 168 hours or more. An upper limit for the amount of time the transdermal delivery device is maintained in contact with a subject before removal is, in some instances, 168 hours or shorter, such as 144 hours or shorter, such as 120 hours or shorter, such as 96 hours or shorter, such as 72 hours or shorter, such as 48 hours or shorter, such as 24 hours or shorter, such as 12 hours or shorter, such as 8 hours or shorter, such as 4 hours or shorter and including 2 hours or shorter.

By "removing" the transdermal delivery device from contact with the subject is meant that no amount of dexmedetomidine from the transdermal composition remains in contact with the subject, including any residual amount of dexmedetomidine left behind on the surface of the skin or mucous membrane when the transdermal delivery device was applied. In other words, when the transdermal delivery device is removed all traces of dexmedetomidine are no longer on the surface of the skin or mucous membrane at the application site, resulting in zero transdermal flux of dexmedetomidine into the subject.

As described above, a dosage interval is a single administration of applying and maintaining the transdermal delivery device in contact with the subject which begins with applying the transdermal dexmedetomidine composition to the skin or mucous membrane of the subject and ends with the removal of the transdermal delivery device from contact with the subject. In certain embodiments, protocols for may include multiple dosage intervals. By "multiple dosage intervals" is meant more than one transdermal delivery device is applied and maintained in contact with the subject in a sequential manner. As such, a transdermal delivery device is removed from contact with the subject and a new transdermal delivery device is reapplied to the subject. In practicing methods of the invention, treatment regimens may include two or more dosage intervals, such as three or more dosage intervals, such as four or more dosage intervals, such as five or more dosage intervals, including ten or more dosage intervals.

The location on the subject for reapplying subsequent transdermal delivery devices in multiple dosage treatment regimens may be the same or different from the location on the subject where the previous transdermal delivery device was removed. For example, if a first transdermal delivery device is applied and maintained on the leg of the subject, one or more subsequent transdermal delivery devices may be reapplied to the same position on the leg of the subject. On the other hand, if a first transdermal delivery device was applied and maintained on the leg of the subject, one or more subsequent transdermal delivery device may be reapplied to a different position, such as the abdomen or back of the subject. Subsequent dosages applied in multiple dosage interval regimens may have the same or different formulation of dexmedetomidine. In certain instances, a subsequent dosage interval in a treatment regimen may contain a higher or lower concentration of dexmedetomidine than the previous dosage interval. For example, the concentration of dexmedetomidine may be increased in subsequent dosage intervals by 10% or greater, such as 20% or greater, such as 50% or greater, such as 75% or greater, such as 90% or greater and including 100% or greater. An upper limit for the increase in concentration of dexmedetomidine in subsequent dosage intervals is, in some instances, 10-fold or less, such as 5-fold or less, such as 2-fold or less, such as 1-fold or less, such as 0.5-fold or less and including 0.25-fold or less.

On the other hand, the concentration of dexmedetomidine may be decreased in subsequent dosage intervals, such as by 10% or greater, such as 20% or greater, such as 50% or greater, such as 75% or greater, such as 90% or greater and including 100% or greater. An upper limit for the decrease in concentration of dexmedetomidine in subsequent dosage intervals is, in some instances, 10-fold or less, such as 5-fold or less, such as 2-fold or less, such as 1-fold or less, such as 0.5-fold or less and including 0.25-fold or less.

In other instances, a subsequent dosage interval may contain a different formulation of dexmedetomidine than the previous dosage interval, such as a different pressure sensitive adhesive or the presence or absence of a permeation enhancer, as described above.

Methods for applying and maintaining in contact with a subject a transdermal delivery device having a single layer matrix dexmedetomidine composition according to the present invention find use in any application where a subject would benefit from being transdermally administered dexmedetomidine, such as a malady, disease, ailment or condition that can be treated with the stimulation of α-adrenergic receptor agonist activity. For example, transdermal delivery devices having a single layer matrix dexmedetomidine composition may be employed according to certain embodiments to treat or manage pain syndromes, including but not limited to neuropathic pain, idiopathic pain, acute pain, sympathetically mediated pain, complex regional pain, chronic pain, such as cancer pain, post-operative pain, post-herpetic neuralgia, irritable bowel syndrome and other visceral pain, diabetic neuropathy, pain associated with muscle spasticity, complex regional pain syndrome (CRPS), sympathetically maintained pain, headache pain including migraine headaches, allodynic pain, inflammatory pain, such as pain associated with arthritis, gastrointestinal pain, such as irritable bowel syndrome (IBS) and Crohn's disease, opioid addiction, attention deficit hyperactivity disorder and associated ailments such as restless legs syndrome, hypertension, Tourette's syndrome, depression and other psychiatric disorders such as schizophrenia and bipolar disorder, ocular hypertension, glaucoma, spasticity, atypical depression, panic disorder, social phobia, enuresis in children, obsessive-compulsive disorder, bulimia, narcolepsy, Parkinson's disease, Alzheimer's disease, amyotrophic lateral sclerosis and multiple sclerosis, ischemia, epilepsy, neuropathies such as diabetic and ischemic retinopathy, among other types of ailments and conditions where the subject will benefit from stimulation of α-adrenergic receptor agonist activity with an amount of dexmedetomidine. Other indications and applications of interest also include, but are not limited to those indications as described in United States Patent Publication No. 2005/0058696, United States Patent Publication No. 2005/0059664, United States Patent Publication No. 2010/0196286 and International Patent Publication No. WO 2011/085162, the disclosures of which are herein incorporated by reference in their entirety.

In certain embodiments, transdermal delivery devices having a single layer matrix dexmedetomidine composition may be employed to manage pain, such as for example as more fully described in U.S. Provisional Patent Application Ser. No. 61/887,870, entitled "Methods and Compositions for Managing Pain Comprising Non-Sedative Dexmedetomidine Transdermal Compositions" (Attorney Docket No. TEIK-067PRV) filed Oct. 7, 2013, the disclosure of which is herein incorporated by reference in its entirety.

In other embodiments, transdermal delivery devices having a single layer matrix dexmedetomidine composition may be employed according to embodiments of the invention to treat withdrawal syndrome, such as for example as more fully described in U.S. Provisional Patent Application Ser. No. 61/887,871, entitled "Methods and Compositions for Treating Withdrawal Syndromes Comprising Non-Sedative Dexmedetomidine Transdermal Compositions" (Attorney Docket No. TEIK-068PRV) filed Oct. 7, 2013, the disclosure of which is herein incorporated by reference in its entirety.

In yet other embodiments, transdermal delivery devices having a single layer matrix dexmedetomidine composition may be employed to treat attention deficit hyperactivity disorder or insomnia, such as for example as more fully described in U.S. Provisional Patent Application Ser. No. 61/887,862, entitled "Methods and Compositions for Treating Attention Deficit Hyperactivity Disorder, Anxiety and Insomnia Comprising Dexmedetomidine Transdermal Compositions" (Attorney Docket No. TEIK-065PRV) filed Oct. 7, 2013, the disclosure of which is herein incorporated by reference in its entirety.

Kits

Kits for use in practicing certain methods described herein are also provided. In certain embodiments, the kits include one or more transdermal delivery devices containing a single layer matrix dexmedetomidine composition having an amount of dexmedetomidine and pressure sensitive adhesive as described above. In certain embodiments, the kits include an adhesive overlay as described above. In a given kit that includes two or more of the subject transdermal delivery devices, the compositions may be individually packaged or present within a common container. In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following examples are offered by way of illustration and not by way of limitation. Specifically, the following examples are of specific embodiments for carrying out the present invention. The examples are for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXPERIMENTAL

Materials and Methods

Preparation of Example Dexmedetomidine Transdermal Formulations

Formulations were prepared by mixing dexmedetomidine and a pressure sensitive adhesive in organic solvents (e.g., 30-60 wt % solid content in ethyl acetate, isopropyl alcohol, hexane, or heptane), followed by mixing. Once a homogeneous mixture was formed, the solution was cast on a release liner (siliconized polyester or fluoropolymer coated polyester sheets of 2-3 mils) and dried at 60°-80° C. for 10-90 minutes. The single layer adhesive films were then laminated to a PET backing, cut to the desired size, and pouched. In some instances, crosslinked polyvinylpyrrolidone (PVP-CLM), polyvinylpyrrolidone K90 (PVP K90), levulinic acid (LA), oleic acid (OA), lauryl lactate (LL), and propylene glycolmonolaurate (PGML) was added to the adhesive composition.

Transdermal Flux Tests

Human cadaver skin was used and epidermal layers (stratum corneum and viable epidermis) were separated from the full-thickness skin as skin membrane. Samples were die-cut with an arch punch to a final diameter of about 2.0 cm$^2$. The release liner was removed and the system was placed on top of the epidermis/stratum corneum with the dexmedetomidine adhesive layer facing the outer surface of the stratum corneum. Gentle pressure was applied to effect good contact between the adhesive layer and stratum corneum. The donor and receptor sides of the Franz cell were clamped together and the receptor solution containing a phosphate buffer at pH 6.5 and 0.01% gentamicin was added to the Franz cell. The cells were kept at 32° C.-35° C. for the duration of the experiment. Samples of the receptor solution were taken at regular intervals and the active agent concentration was measured by HPLC. The removed receptor solution was replaced with fresh solution to maintain sink conditions. The flux was calculated from the slope of cumulative amount of the drug permeated into the receiver compartment versus time plot.

Examples

Example 1

In-Vitro Flux Obtained from Dexmedetomidine Transdermal Composition Formulations in PIB/PB Polymers Pressure-sensitive adhesives used in this example are polyisobutylene/polybutene (PIB/PB) adhesives. The PIB/PB adhesives are mixtures of high molecular weight PIB (5% Oppanol B100), low molecular weight PIB (25% Oppanol B12) and a polybutene tackifier, e.g., Indopol H1900 or Panalane H-300e (20%) in organic solvent, e.g., heptane (50%). The combination was mixed for about 3 days, until the mixture was homogeneous. Example dexmedetomidine transdermal composition formulations are shown in Tables 1 and 2.

An in-vitro skin flux study was performed as described above with transdermal delivery devices having different concentrations of dexmedetomidine as shown in Table 1. The average dexmedetomidine in-vitro skin flux with respect to time is illustrated in FIG. 1. As depicted in FIG. 1, dexmedetomidine in-vitro skin flux was high in the initial hours in the case of 1% formulation (Formulation 1) as compared to higher drug loading (Formulations 2 and 3). Formulations 2 and 3 were found to have needle-like crystals of dexmedetomidine, therefore flux profile is constant and did not change with drug loading. However, no crystals were observed in Formulation 1. Formulation 1 includes a saturated or supersaturated amount of dexmedetomidine.

Figure 2:
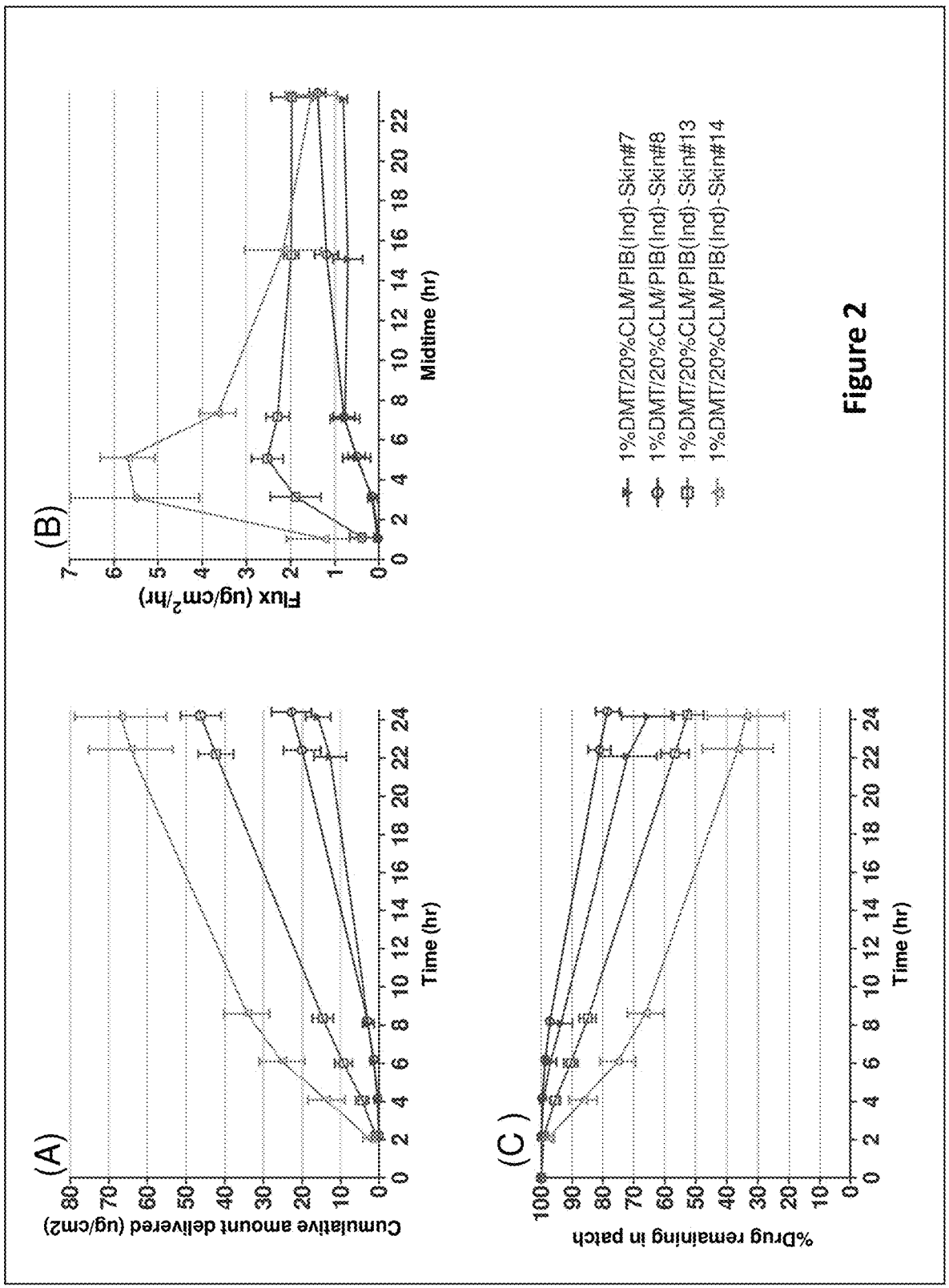
FIG. 2A shows an example of cumulative dexmedetomidine delivered amount with time according to one embodiment.
FIG. 2B shows an example of a plot of average dexmedetomidine flux as a function of transdermal delivery device application time for a dexmedetomidine transdermal composition having a non-functionalized acrylate adhesive according to one embodiment.
FIG. 2C shows an example of dexmedetomidine utilization with time according to one embodiment.

Dexmedetomidine transdermal formulation was also made using PIB made from Indopol H1900 as shown in Table 2. The results of dexmedetomidine in-vitro permeation from 1% dexmedetomidine formulation made with 20% PVP-CLM in PIB/PB adhesive (Formulation 4) through skins that have different skin permeability are illustrated in FIG. 2. FIG. 2(A) shows the cumulative dexmedetomidine delivered amount with time. The in-vitro permeation of dexmedetomidine deviated depending on the permeability of the skin. The in-vitro dexmedetomidine delivered amount could vary from 4-35 ug/cm2 at 8 hr. and 15-67 ug/cm2 at 24 hr. FIG. 2(B) shows the flux or derivative of cumulative drug delivered amount with respect to time. The delivery rate of dexmedetomidine from Formulation 2 reached the maximum at about 5-7 hr, then maintain constant for at least 24 hr. In case of high permeable skin (Skin#14), the flux might decreased due to depletion. FIG. 2(C) shows the % drug remaining in patch with time. As depicted in FIG. 2(C), the utilization of dexmedetomidine obtained from Formulation 4 was 20-70% after applying the patch for 24 hr.

TABLE 1

| | % w/w | | |
| --- | --- | --- | --- |
| Components | Formulation 1 (1% DMT/20% CLM/PIB) | Formulation 2 (3% DMT/20% CLM/PIB) | Formulation 3 (5% DMT/20% CLM/PIB) |
| Dexmedetomidine | 1.00 | 3.00 | 5.00 |
| PVP-CLM | 20.00 | 20.00 | 20.00 |
| PIB/PB (Panalane H-300e) | 79.00 | 77.00 | 75.00 |

TABLE 2

| Components | % w/w Formulation 4 [1% DMT/20% CLM/PIB(Ind)] |
|---|---|
| Dexmedetomidine | 1.00 |
| PVP-CLM | 20.00 |
| PIB/PB (Indopol H1900) | 79.00 |

Example 2

Figure 3:
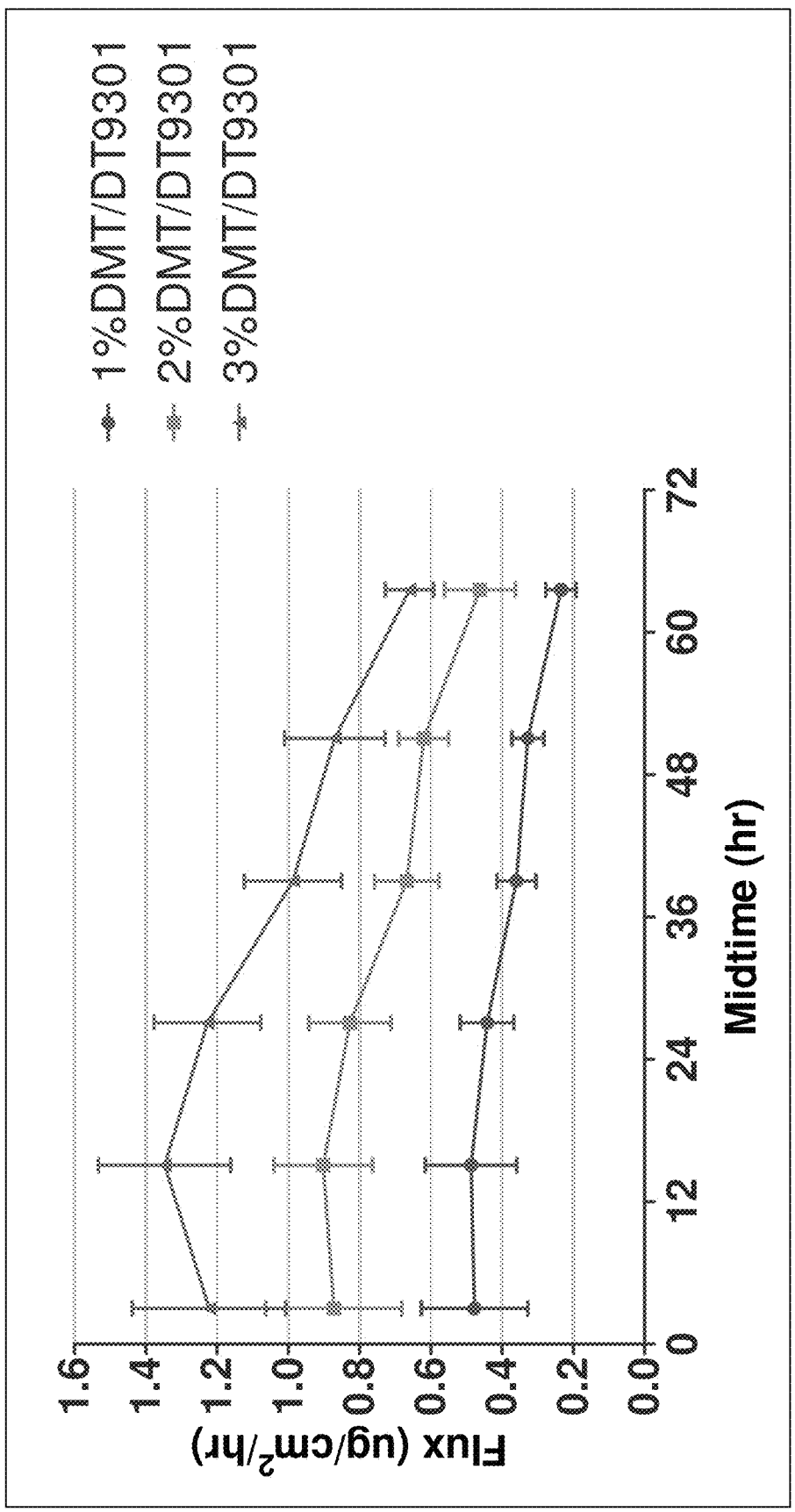
FIG. 3 shows an example of a plot of average dexmedetomidine flux as a function of transdermal delivery device application time for a dexmedetomidine transdermal composition having a non-functionalized acrylate adhesive according to one embodiment.

In-Vitro Flux Obtained from Dexmedetomidine Transdermal Composition Formulations in Non-Functionalized Acrylate Polymers Dexmedetomidine in-vitro flux was measured using non-functionalized acrylate adhesive. An example of a non-functionalized acrylate adhesive used experimentally includes non-functionalized acrylate polymer Duro-Tak 87-9301. An in-vitro skin flux study was performed as described above with transdermal delivery devices having different concentrations of dexmedetomidine in non-functional Duro-Tak 87-9301. Dexmedetomidine transdermal composition formulations are shown in Table 3. The average dexmedetomidine in-vitro flux with respect to time is illustrated in FIG. 3. As depicted in FIG. 3, higher dexmedetomidine loading gave increased in-vitro skin flux.

TABLE 3

| | % w/w | | |
|---|---|---|---|
| Components | Formulation 5 (1% DMT/ DT9301) | Formulation 6 (2% DMT/ DT9301) | Formulation 7 (3% DMT/ DT9301) |
| Dexmedetomidine base | 1.00 | 2.00 | 3.00 |
| Pressure Sensitive Adhesive Duro-Tak 87-9301 | 99.00 | 98.00 | 97.00 |

Example 3

In-Vitro Flux Obtained from Dexmedetomidine Transdermal Composition Formulations in Hydroxyl (—OH) Functionalized Acrylate Polymers Dexmedetomidine in-vitro flux was measured using hydroxyl (—OH) functionalized acrylate adhesives. Examples of a hydroxyl functionalized acrylate adhesive used experimentally include hydroxyl functionalized acrylate polymers, e.g., Duro-Tak 87-4287, Duro-Tak 387/87-2510, Duro-Tak 387/87-2287 and Duro-Tak 387/87-2516. An in-vitro skin flux study was performed as described above with transdermal delivery devices having different concentrations of dexmedetomidine with different hydroxyl functionalized acrylate adhesives.

Figure 4:
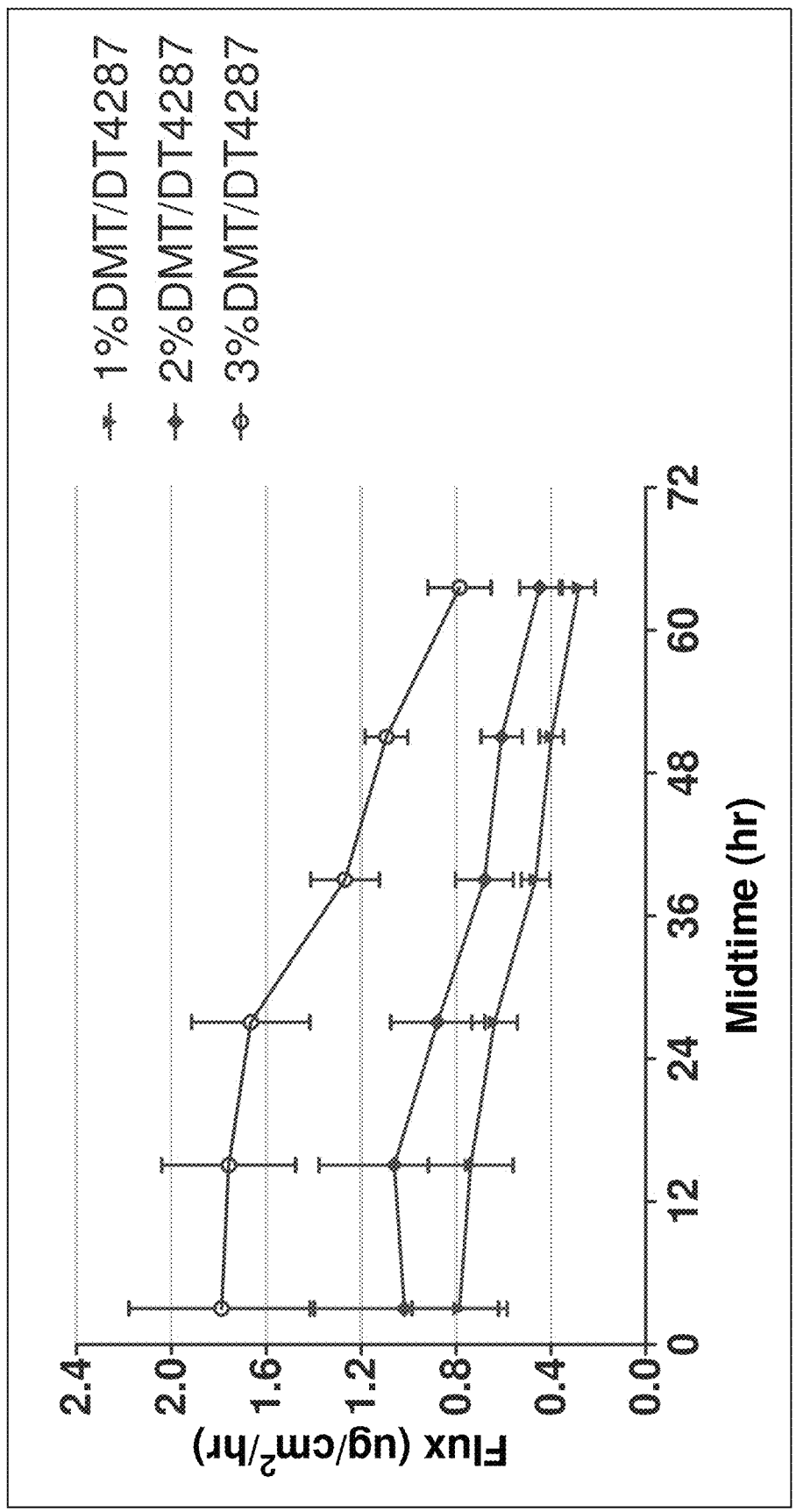
FIG. 4 shows an example of a plot of average dexmedetomidine flux as a function of transdermal delivery device application time for a dexmedetomidine transdermal composition having a hydroxyl functionalized acrylate adhesive containing vinyl acetate according to one embodiment.
Figure 5:
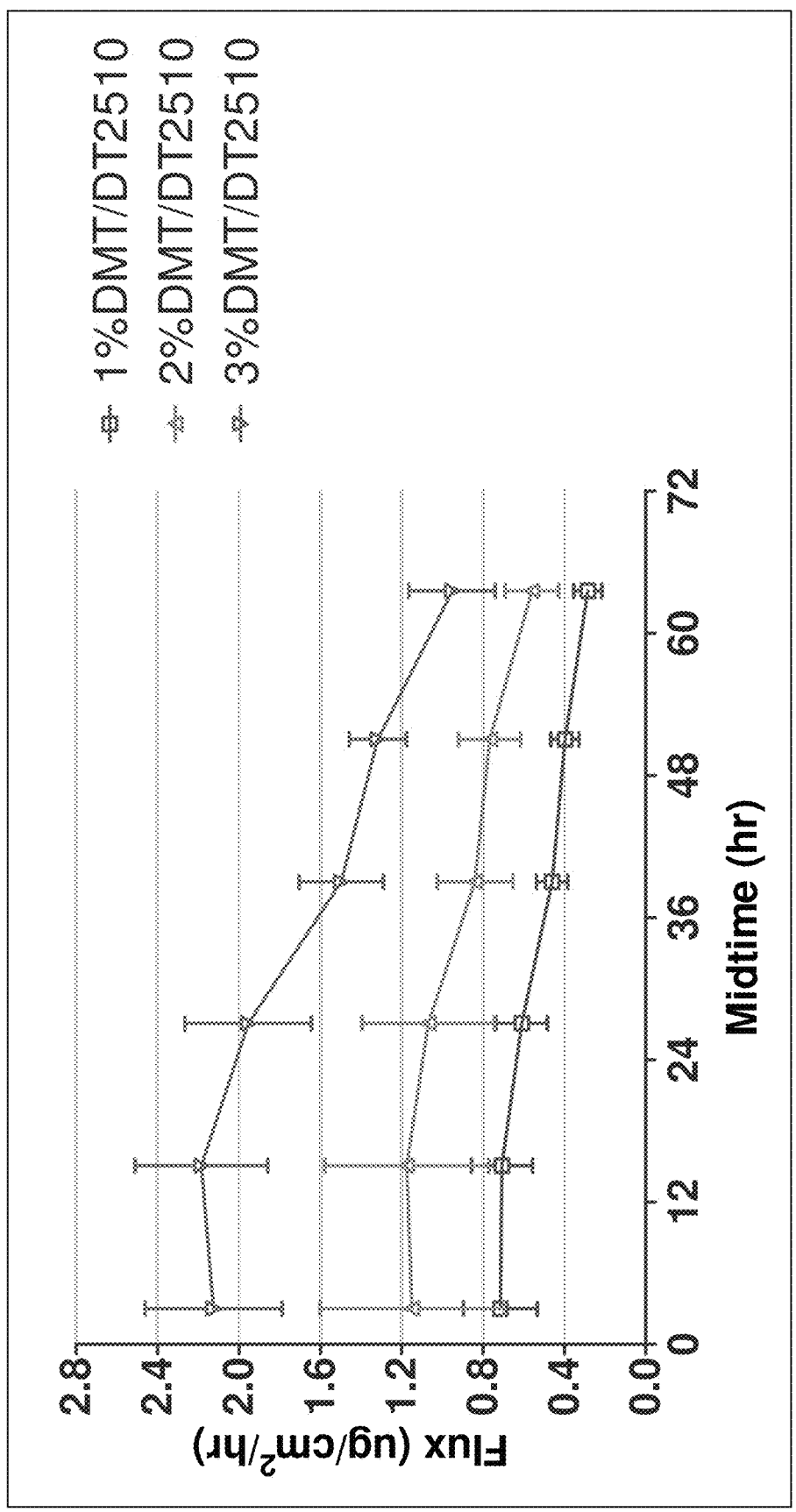
FIG. 5 shows an example of a plot of average dexmedetomidine flux as a function of transdermal delivery device application time for a dexmedetomidine transdermal composition having a hydroxyl functionalized acrylate adhesive according to another embodiment.

Tables 4 and 5 show the dexmedetomidine transdermal composition formulations with different concentrations of dexmedetomidine in Duro-Tak 87-4287 (acrylate-vinyl acetate polymer) or Duro-Tak 387/87-2510 (acrylate polymer). The mean dexmedetomidine in-vitro fluxes are illustrated in FIGS. 4 and 5. As depicted in FIGS. 4 and 5, dexmedetomidine in-vitro flux increased with the dexmedetomidine loading in the formulation.

TABLE 4

| | % w/w | | |
|---|---|---|---|
| Components | Formulation 8 (1% DMT/ DT4287) | Formulation 9 (2% DMT/ DT4287) | Formulation 10 (3% DMT/ DT4287) |
| Dexmedetomidine base | 1.00 | 2.00 | 3.00 |
| Pressure Sensitive Adhesive Duro-Tak 87-4287 | 99.00 | 98.00 | 97.00 |

TABLE 5

| | % w/w | | |
|---|---|---|---|
| Components | Formulation 11 (1% DMT/ DT2510) | Formulation 12 (2% DMT/ DT2510) | Formulation 13 (3% DMT/ DT2510) |
| Dexmedetomidine base | 1.00 | 2.00 | 3.00 |
| Pressure Sensitive Adhesive Duro-Tak 387/87-2510 | 99.00 | 98.00 | 97.00 |

Figure 6:
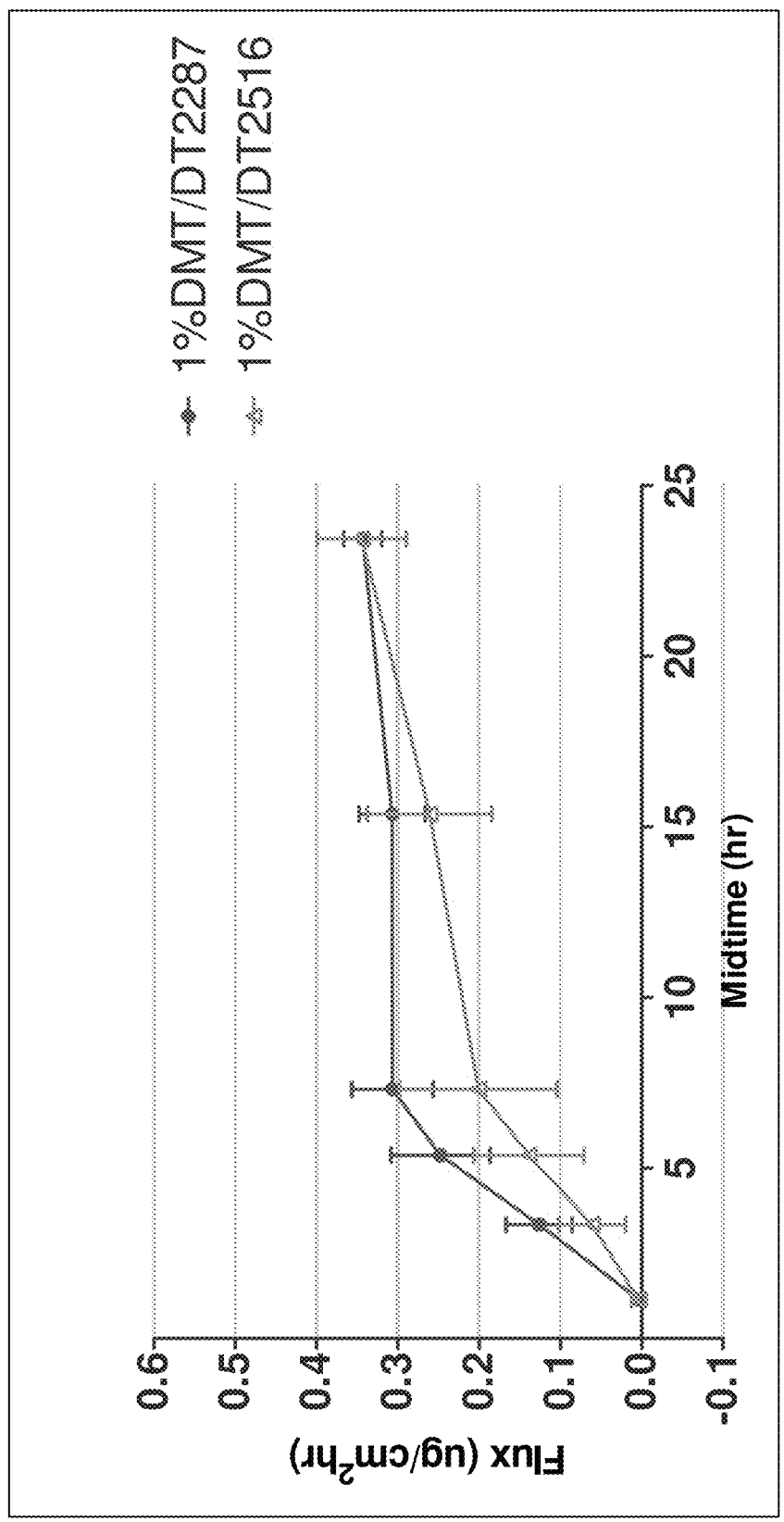
FIG. 6 shows an example of a plot of average dexmedetomidine flux as a function of transdermal delivery device application time for a dexmedetomidine transdermal composition having hydroxyl functionalized acrylate adhesive and a hydroxyl functionalized acrylate adhesive containing vinyl acetate according to another embodiment.

Tables 6 show the dexmedetomidine transdermal composition formulations containing 1% dexmedetomidine in another hydroxyl functionalized acrylate polymers containing vinyl acetate, e.g., Duro-Tak 87-2287 (no crosslinker added polymer) and Duro-Tak 87-2516 (crosslinker added polymer). The mean dexmedetomidine in-vitro fluxes are illustrated in FIG. 6. As depicted in FIG. 6, in-vitro flux obtained from Duro-Tak 387/87-2287 was slightly higher than that from Duro-Tak 387/87-2516, possibly resulting from the higher adhesion properties of Duro-Tak 387/87-2287 compared with Duro-Tak 387/87-2516.

TABLE 6

| | % w/w | |
|---|---|---|
| Components | Formulation 14 (1% DMT/ DT2287) | Formulation 15 (1% DMT/ DT2516) |
| Dexmedetomidine base | 1.00 | 1.00 |
| Pressure Sensitive Adhesive Duro-Tak 387/87-2287 | 99.00 | 0.00 |
| Pressure Sensitive Adhesive Duro-Tak 387/87-2516 | 0.00 | 99.00 |

Example 4

Figure 7A:
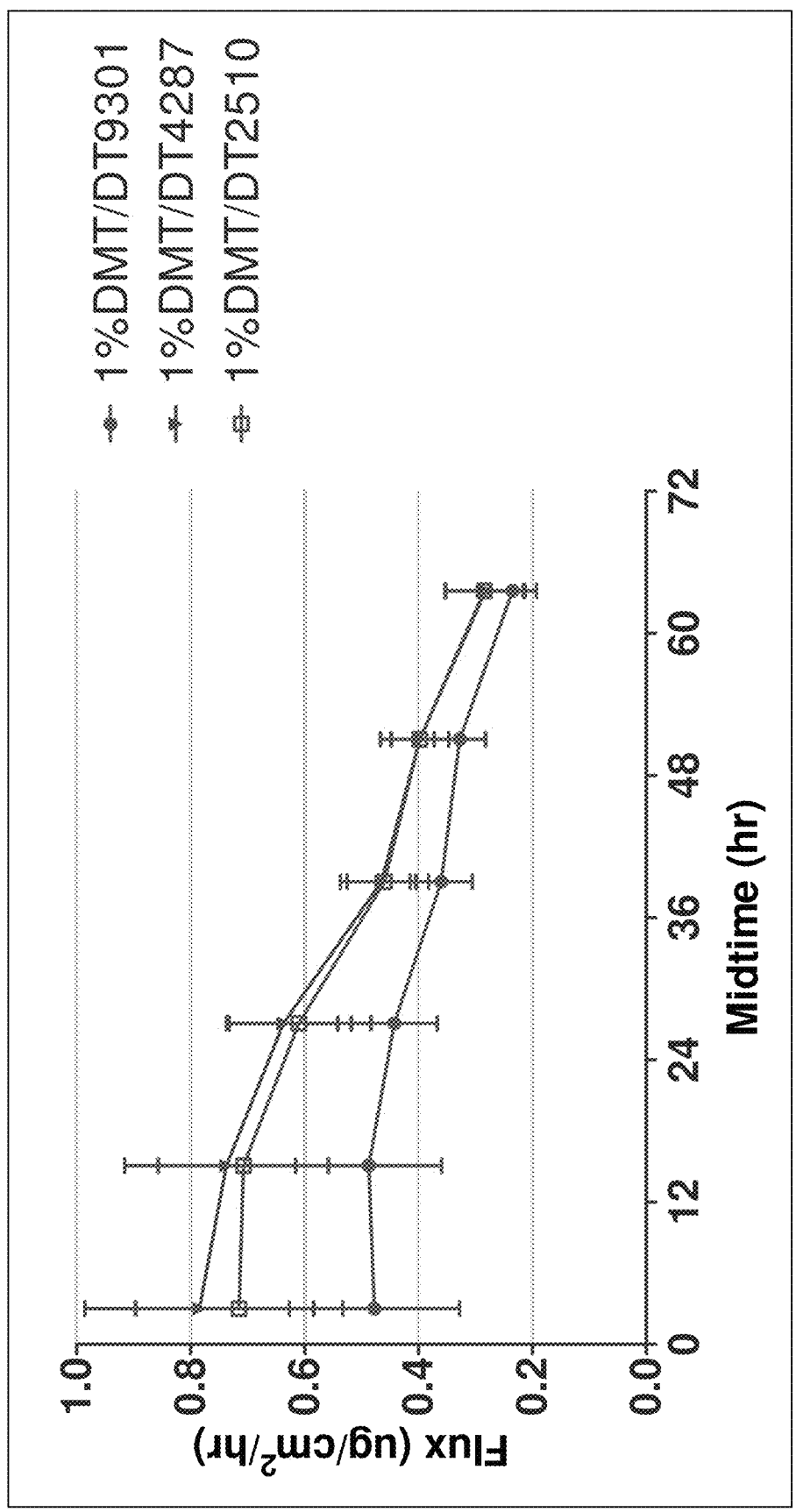
FIGS. 7A-7B shows an example of a plot of average dexmedetomidine flux as a function of transdermal delivery device application time for dexmedetomidine transdermal compositions having a non-functionalized acrylate adhesive, a hydroxyl functionalized acrylate adhesive and a hydroxyl functionalized acrylate adhesive containing vinyl acetate according to one embodiment.
Figure 7B:
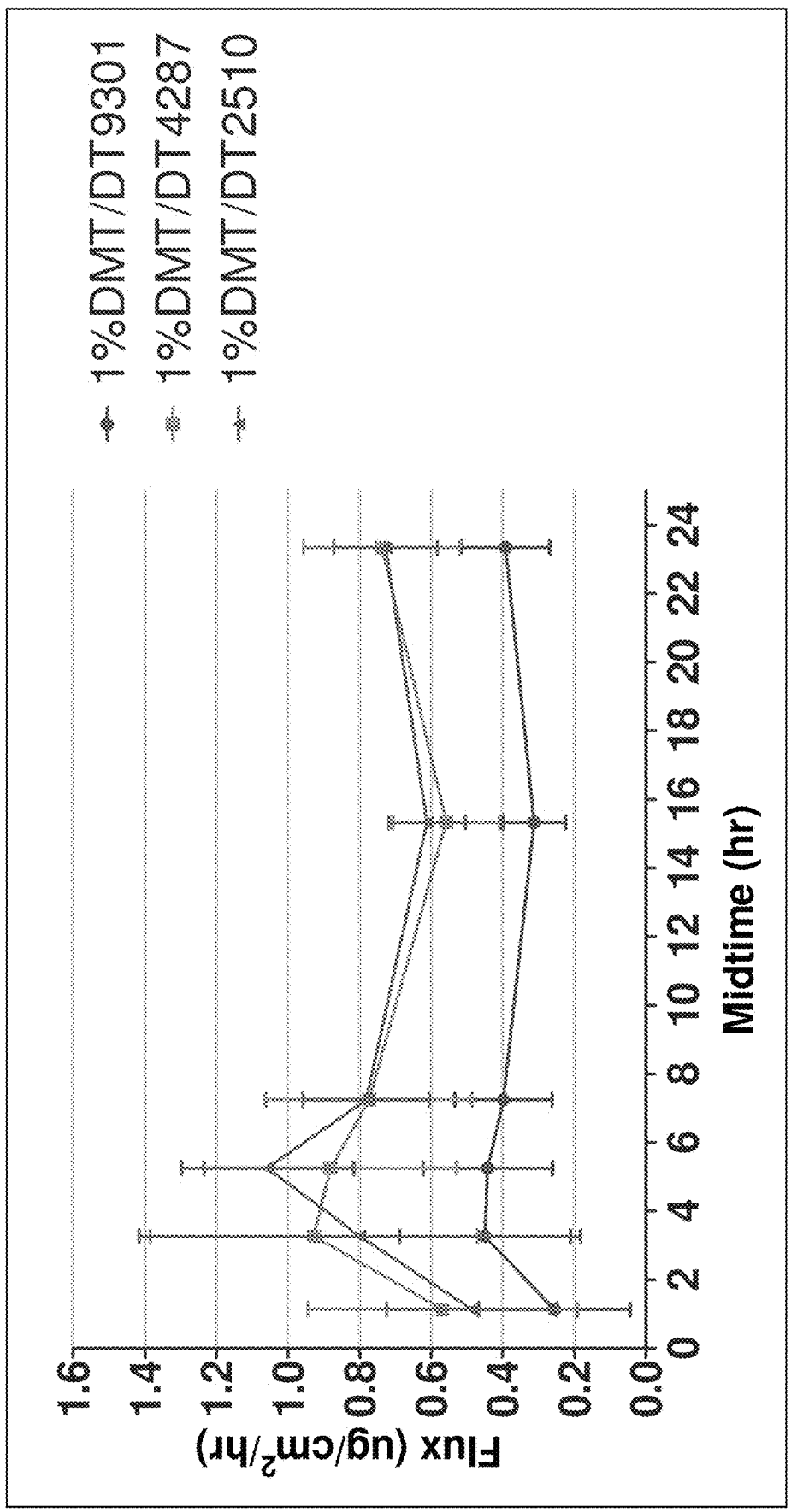

In-Vitro Flux Obtained from 1% Dexmedetomidine Transdermal Composition Formulations in Non-Functionalized or Hydroxyl (—OH) Functionalized Acrylate Polymers Another set of examples of dexmedetomidine transdermal formulations are transdermal compositions which include 1% w/w dexmedetomidine with non-functionalized acrylate polymer (Duro-Tak 87-9301, Formulation 5), hydroxyl functionalized acrylate polymer (Duro-Tak 387/87-2510, Formulation 11) and hydroxyl functionalized acrylate polymer containing vinyl acetate (Duro-Tak 87-4287, Formulation 8). In-vitro flux experiments were performed for 3 days and 1 day and the results are shown in FIGS. 7A and 7B, respectively. As depicted in both FIGS. 7A and 7B, dexmedetomidine in-vitro flux was less in non-functional adhesives as compared to hydroxyl functionalized adhesives with the same drug loading.

Example 5

In-Vitro Flux Obtained from Dexmedetomidine Transdermal Composition Formulations in Acid (—COOH) Functionalized or Acid/Hydroxyl (—COOH/OH) Functionalized Acrylate Polymers Dexmedetomidine in-vitro flux was measured using acid (—COOH) functionalized or acid/hydroxyl (—COOH/OH) functionalized acrylate adhesives. Examples of acid (—COOH) functionalized acrylate adhesive used in this study is Duro-Tak 387/87-2353 (no crosslinker added acrylate polymer). The acid/hydroxyl (—COOH/OH) functionalized acrylate adhesive used in this study is Duro-Tak 87-2979 (crosslinker added acrylate-vinyl acetate polymer). Tables 7 and 8 show the dexmedetomidine transdermal composition formulations with different acid (—COOH) functionalized or acid/hydroxyl (—COOH/OH) functionalized acrylate polymers. The concentration of dexmedetomidine in the formulations was selected based on the solubility of dexmedetomidine in each adhesive. The solubility of dexmedetomidine in Duro-Tak 387/87-2353 was found to be about 10-15%, whereas that in Duro-Tak 87-2979 was found to be less than 2%. The solubility of drug in acid functionalized acrylate adhesives was greater than that in non-functionalized or hydroxyl functionalized acrylate adhesives.

Figure 8:
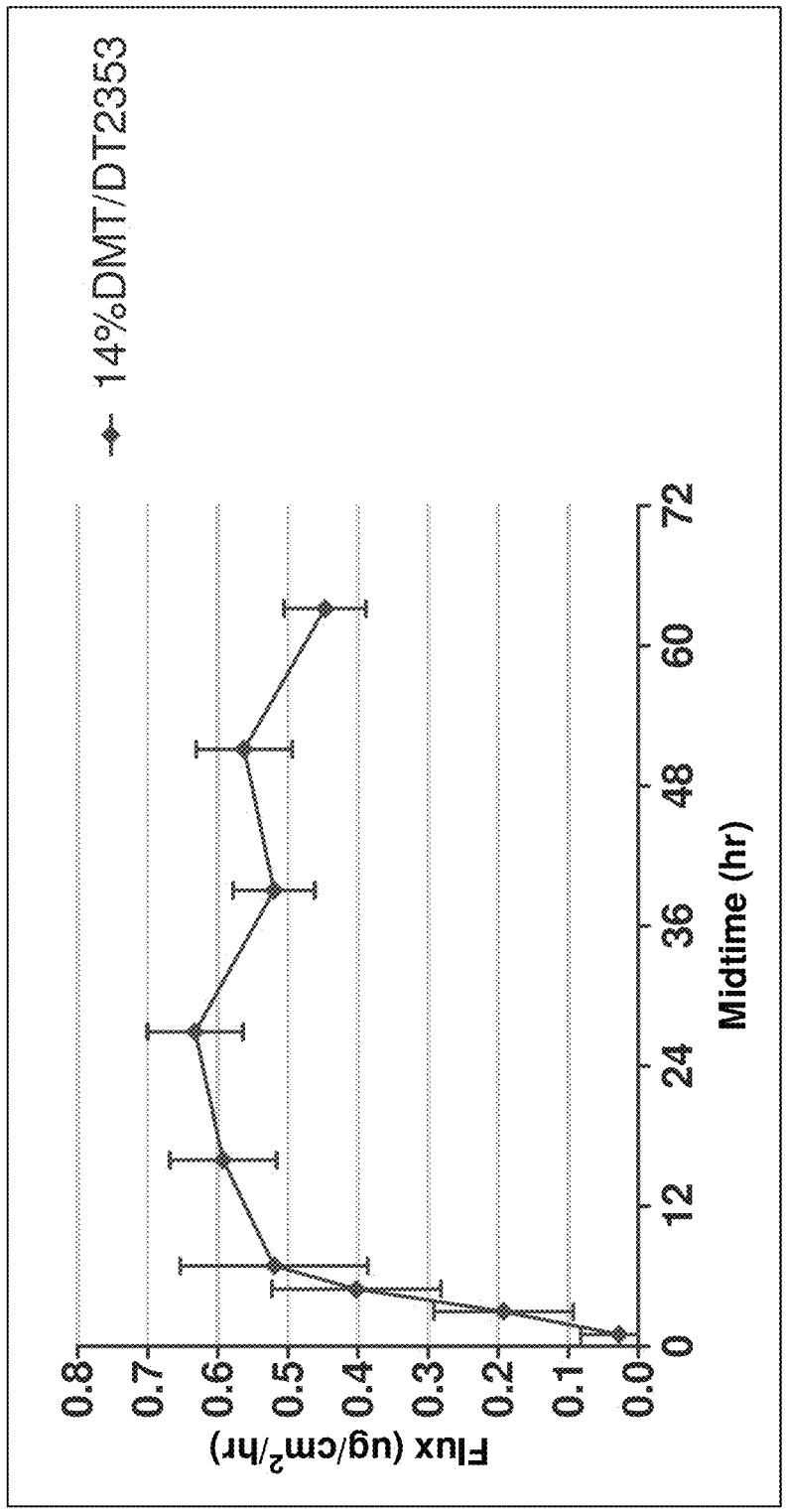
FIG. 8 shows an example of a plot of average dexmedetomidine flux as a function of transdermal delivery device application time for a dexmedetomidine transdermal composition having a carboxylic acid functionalized acrylate adhesive according to another embodiment.
Figure 9:
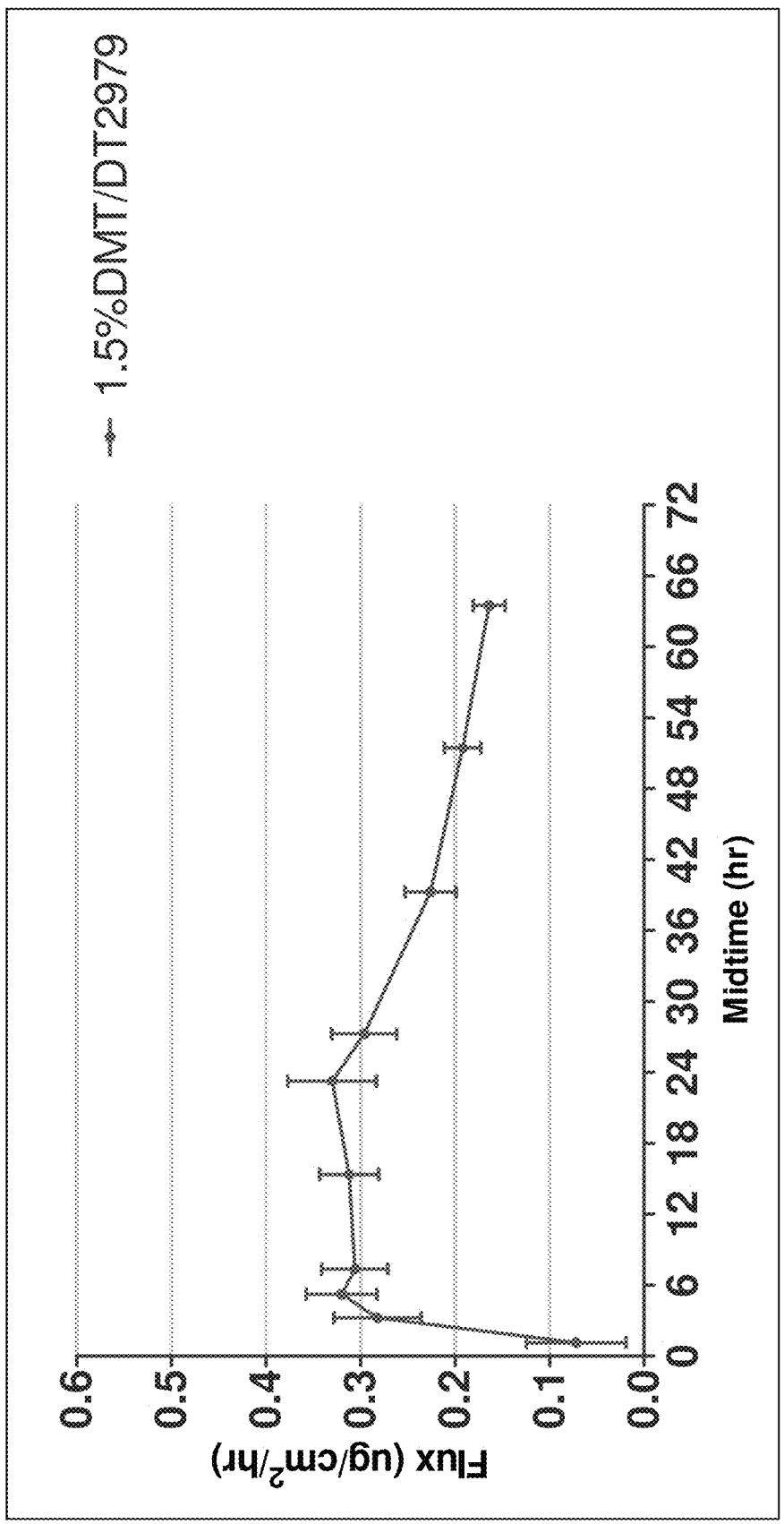
FIG. 9 shows an example of a plot of average dexmedetomidine flux as a function of transdermal delivery device application time for a dexmedetomidine transdermal composition having acrylic adhesive with carboxyl group and hydroxyl group as the functional group containing vinyl acetate according to another embodiment.

In-vitro skin flux study was performed as described above. The mean dexmedetomidine in-vitro fluxes are illustrated in FIGS. 8 and 9.

TABLE 7

| Components | % w/w Formulation 16 (14% DMT/ DT2353) |
|---|---|
| Dexmedetomidine base | 14.00 |
| Pressure Sensitive Adhesive Duro-Tak 387/87-2353 | 86.00 |

TABLE 8

| Components | % w/w Formulation 17 (1.5% DMT/DT2979) |
|---|---|
| Dexmedetomidine base | 1.00 |
| Pressure Sensitive Adhesive Duro-Tak 87-2979 | 99.00 |

Example 6

In-Vitro Flux Obtained from Dexmedetomidine Transdermal Composition Formulations in PIB/PB Polymers Containing PVP-CLM and Duro-Tak 387/87-2353

Another example of dexmedetomidine transdermal composition formulation is shown in Table 9. In order to increase the solubility of drug in PIB/PB (e.g., Indopol H-1900) adhesive, PVP-CLM and acid (—COOH) functionalized acrylate polymer (Duro-Tak 387/87-2353) were used. Formulations 18 to 21 were prepared with different loadings of Duro-Tak 387/87-2353.

Figure 10:
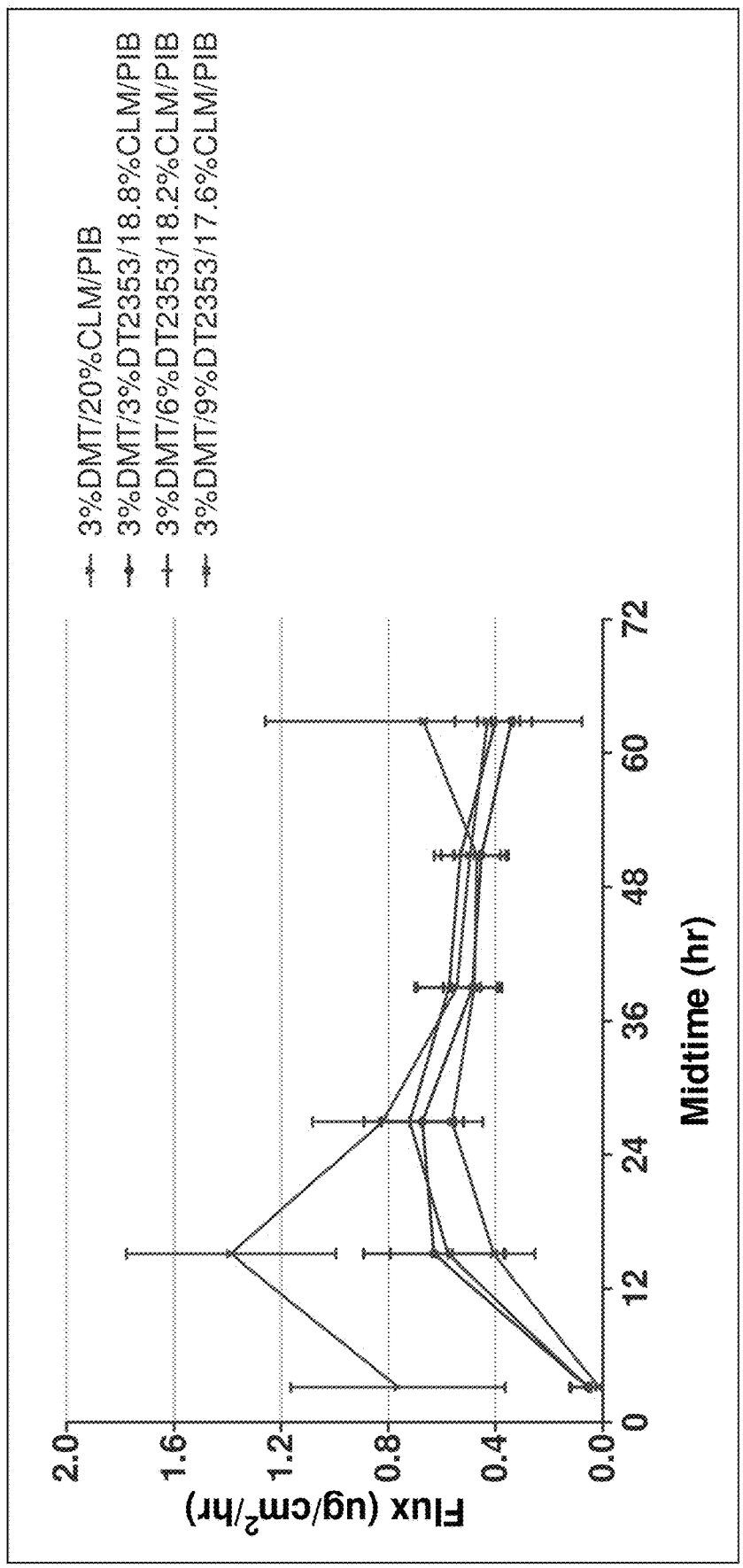
FIG. 10 shows an example of a plot of average dexmedetomidine flux as a function of transdermal delivery device application time for a dexmedetomidine transdermal composition having a polyisobutylene/polybutene adhesive with a carboxylic acid functionalized acrylate adhesive according to one embodiment.

As depicted in FIG. 10, Formulations containing acid (—COOH) functionalized acrylate polymer (Duro-Tak 387/87-2353), Formulations 19, 20 and 21, appear to have lower initial flux compared with Formulations without Duro-Tak 2353 (Formulation 18). The in-vitro flux of dexmedetomidine did not change with 3% and 6% of acid functionalized adhesive, however, at 9% acid functionalized adhesive, a slight decrease in the in-vitro flux is observed.

TABLE 9

| Components | % w/w | | | |
|---|---|---|---|---|
| | Formulation 18 (3% DMT/20% CLM/PIB) | Formulation 19 (3% DMT/3% DT2353/18.8% CLM/PIB) | Formulation 20 (3% DMT/6% DT2353/18.2% CLM/PIB) | Formulation 21 (3% DMT/9% DT2353/17.6% CLM/PIB) |
| Dexmedetomidine base | 3.00 | 3.00 | 3.00 | 3.00 |
| PVP-CLM | 20.00 | 18.8 | 18.7 | 18.6 |
| Pressure Sensitive Adhesive Duro-Tak 387/87-2353 | — | 3.00 | 6.00 | 9.00 |
| PIB/PB (Indopol H-1900) | q.s. to 100 | q.s. to 100 | q.s. to 100 | q.s. to 100 |

Example 7

In-Vitro Flux Obtained from Dexmedetomidine Transdermal Composition Formulations in PIB/PB Polymers Containing PVP-CLM and Levulinic Acid Another example of dexmedetomidine transdermal composition formulation is shown in Table 10. In order to increase the solubility of drug in PIB/PB (e.g., Indopol H-1900) adhesive in presence of 20% PVP-CLM, various concentrations of an acid were used to test increased dexmedetomidine solubility. Formulations 22 to 25 were prepared with different loadings of levulinic acid.

TABLE 10

| | % w/w | | | |
|---|---|---|---|---|
| Components | Formulation 22 (3% DMT/0.6% LA/20% CLM/PIB) | Formulation 23 (3% DMT/0.9% LA/20% CLM/PIB) | Formulation 24 (3% DMT/1.75% LA/20% CLM/PIB) | Formulation 25 (3% DMT/6.9% LA/20% CLM/ PIB) |
| Dexmedetomidine base | 3.00 | 3.00 | 3.00 | 3.00 |
| PVP-CLM | 20.00 | 20.00 | 20.00 | 20.00 |
| Levulinic Acid | 0.60 | 0.90 | 1.75 | 6.90 |
| PIB/PB (Indopol H-1900) | q.s. to 100 | q.s. to 100 | q.s. to 100 | q.s. to 100 |

Figure 11:
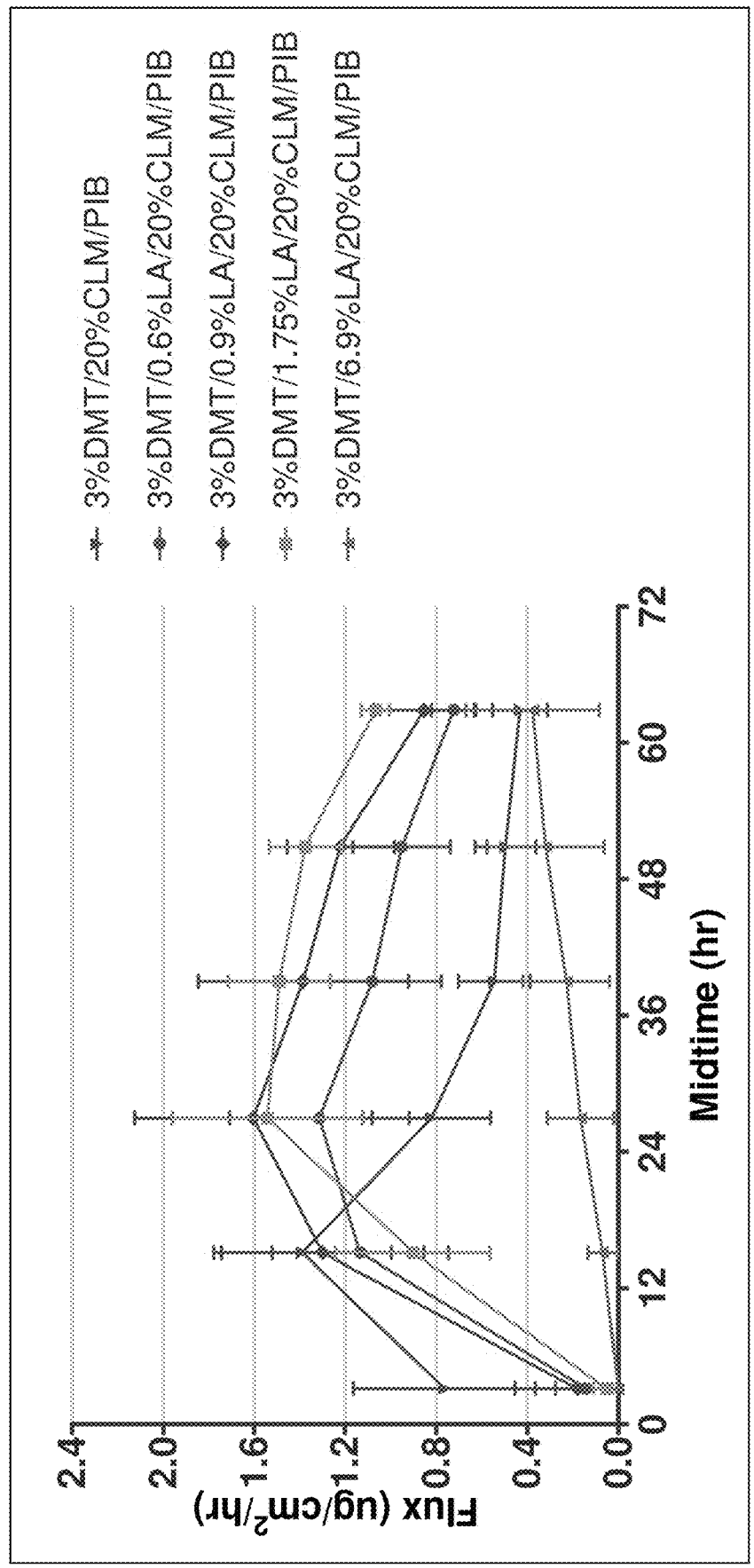
FIG. 11 shows an example of a plot of average dexmedetomidine flux as a function of transdermal delivery device application time for a dexmedetomidine transdermal composition having a polyisobutylene/polybutene adhesive with the solubility enhancer levulinic acid according to one embodiment.

As depicted in FIG. 11, in-vitro flux of dexmedetomidine was reduced dramatically where the formulation included 6.9% of levulinic acid. However, at a concentration of 1.75% levulinic acid, in-vitro flux was comparable to lower concentrations of levulinic acid (i.e., 0.6% and 0.9%). The initial flux obtained from formulations containing levulinic acid (Formulations 22, 23, 24 and 25) was lower than that from formulation without levulinic acid (Formulation 18) However, after 24 hr, the flux obtained from the formulations containing levulinic acid (Formulations 22, 23, 24 and 25) appear to be higher than that from formulation without levulinic acid (Formulation 17). Dexmedetomidine crystals were observed at levulinic acid concentrations of 1.75% and lower.

Example 8

Figure 12:
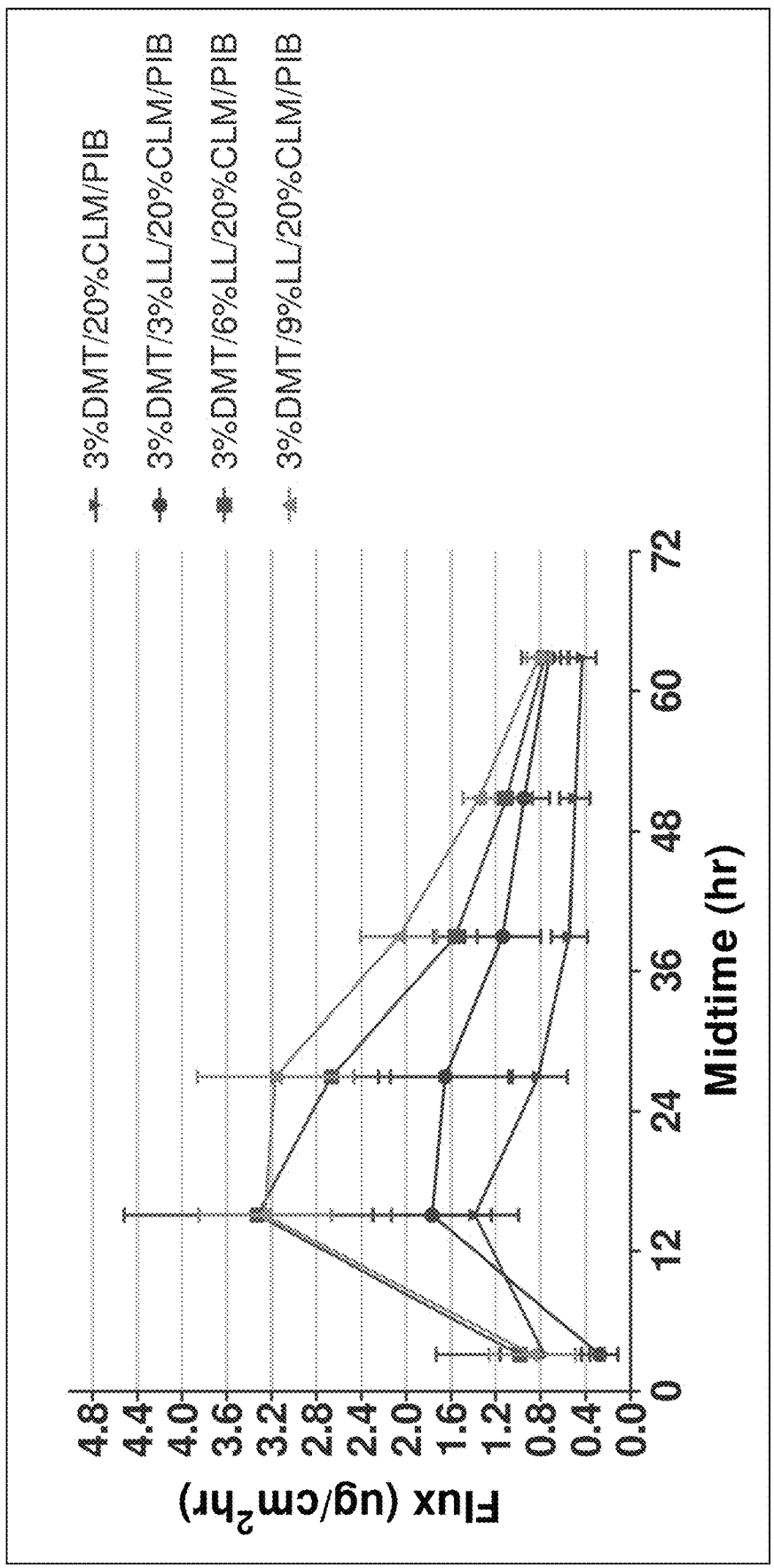
FIG. 12 shows an example of a plot of average dexmedetomidine flux as a function of transdermal delivery device application time for a dexmedetomidine transdermal composition having a polyisobutylene/polybutene adhesive with the solubility enhancer lauryl lactate according to one embodiment.
Figure 13:
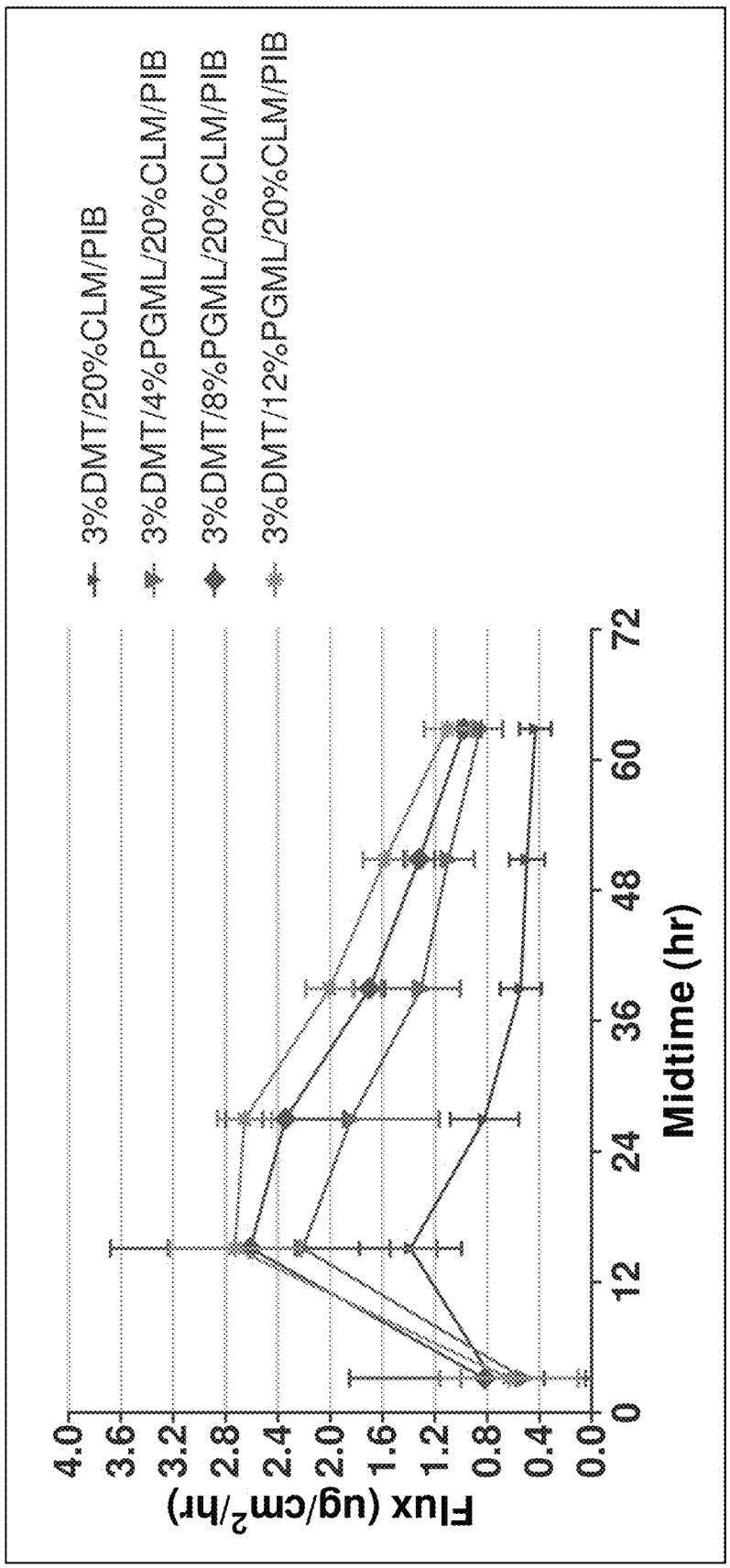
FIG. 13 shows an example of a plot of average dexmedetomidine flux as a function of transdermal delivery device application time for a dexmedetomidine transdermal composition having a polyisobutylene/polybutene adhesive with the solubility enhancer propylene glycolmonolaurate according to one embodiment.

In-Vitro Flux Obtained from Dexmedetomidine Transdermal Composition Formulations in PIB/PB Polymers Containing PVP-CLM and Lauryl Lactate or Propylene Glycolmonolaurate Another example of dexmedetomidine transdermal composition formulations are shown in Tables 11 and 12. Dexmedetomidine has solubility of 5 to 10% in lauryl lactate and propylene glycolmonolaurate. Each of lauryl lactate and propylene glycolmonolaurate increase solubility of dexmedetomidine in the PIB/PB adhesive in the subject formulations. In-vitro flux profiles of Formulations 26 to 28 are shown in FIG. 12. In-vitro flux profiles of Formulations 29 to 31 are shown in FIG. 13. Formulations 26 to 31 were found to have needle-like crystals of dexmedetomidine,

TABLE 11

| | % w/w | | |
|---|---|---|---|
| Components | Formulation 26 (3% DMT/ 3% LL/ 20% CLM/PIB) | Formulation 27 (3% DMT/ 6% LL/ 20% CLM/PIB) | Formulation 28 (3% DMT/ 9% LL/20% CLM/PIB) |
| Dexmedetomidine base | 3.00 | 3.00 | 3.00 |
| PVP-CLM | 20.00 | 20.00 | 20.00 |
| Lauryl lactate | 3.0 | 6.0 | 9.0 |
| PIB/PB (Indopol H-1900) | q.s. to 100 | q.s. to 100 | q.s. to 100 |

TABLE 12

| | % w/w | | |
|---|---|---|---|
| Components | Formulation 29 (3% DMT/4% PGML/ 20% CLM/PIB) | Formulation 30 (3% DMT/ 8% PGML/ 20% CLM/ PIB) | Formulation 31 (3% DMT/ 12% PGML/ 20% CLM/PIB) |
| Dexmedetomidine base | 3.00 | 3.00 | 3.00 |
| PVP-CLM | 20.00 | 20.00 | 20.00 |
| Propylene glycolmonolaurate | 4.0 | 8.0 | 12.0 |
| PIB/PB (Indopol H-1900) | q.s. to 100 | q.s. to 100 | q.s. to 100 |

Example 9

In-Vitro Flux Obtained from Dexmedetomidine Transdermal Composition Formulations in Duro-Tak 387/87-2287 Polymers Containing Levulinic Acid, PVP K90 or Duro-Tak 387/87-2353

Figure 14A:
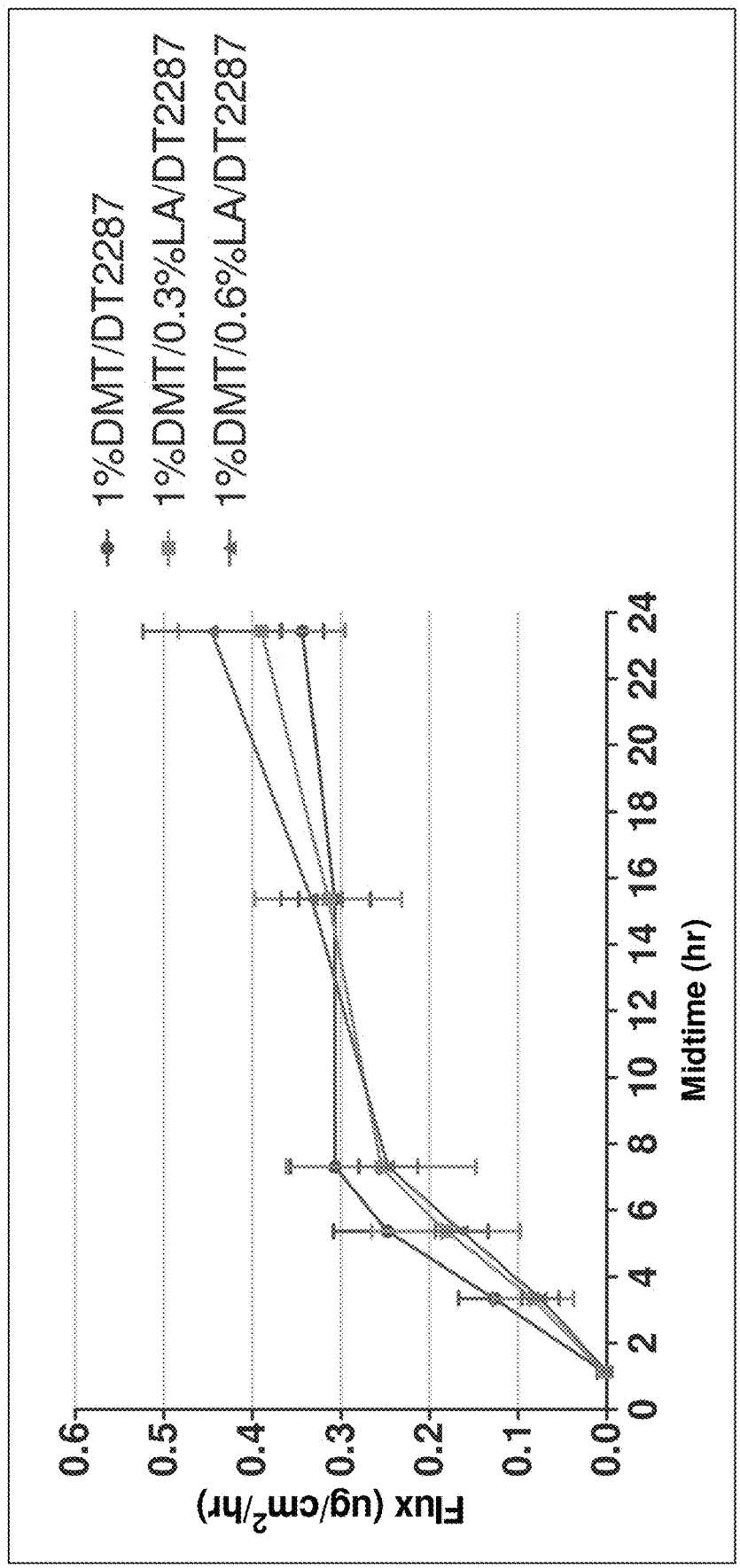
FIG. 14A shows an example of a plot of average dexmedetomidine flux as a function of transdermal delivery device application time for a dexmedetomidine transdermal composition having a hydroxyl functionalized acrylate adhesive containing vinyl acetate with levulinic acid according to one embodiment.
Figure 14B:
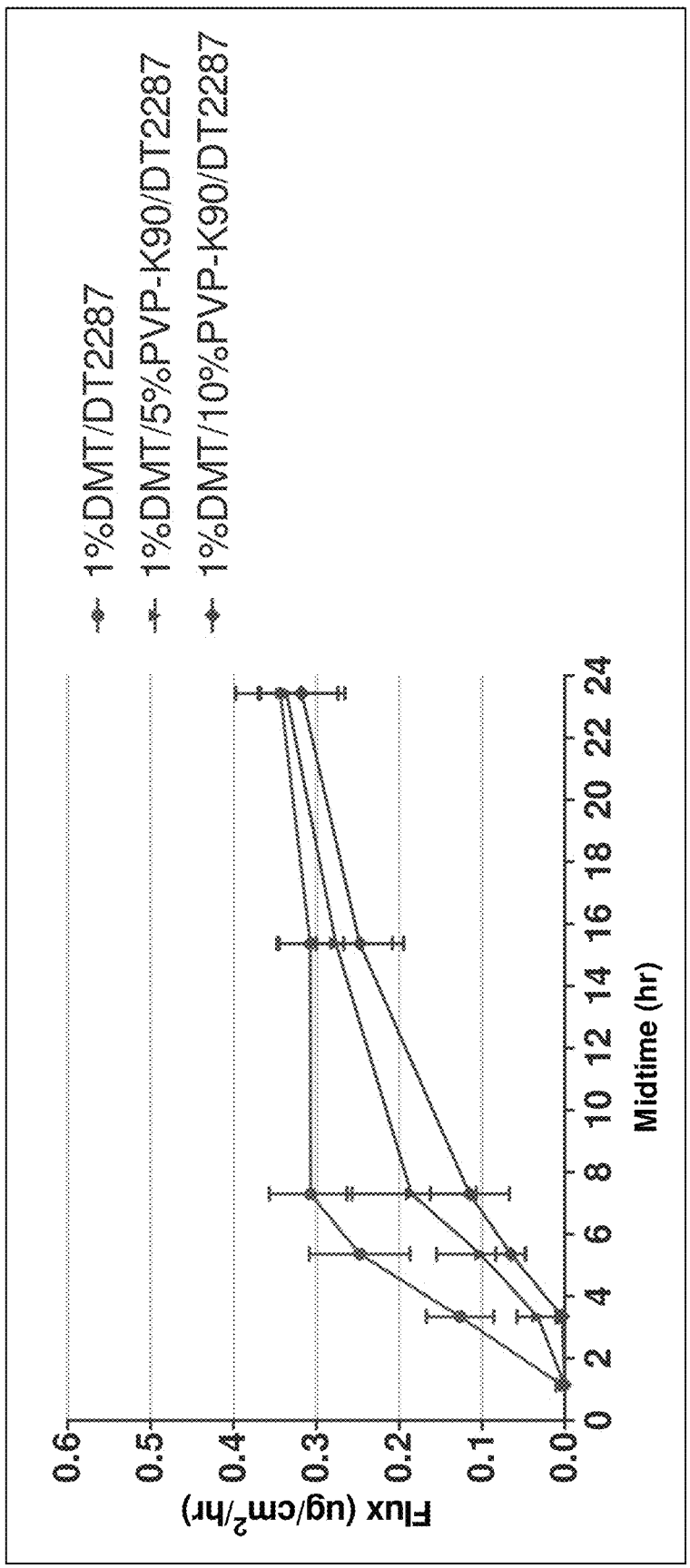
FIG. 14B shows an example of a plot of average dexmedetomidine flux as a function of transdermal delivery device application time for a dexmedetomidine transdermal composition having a hydroxyl functionalized acrylate adhesive containing vinyl acetate with polyvinylpyrrolidone according to one embodiment.
Figure 14C:
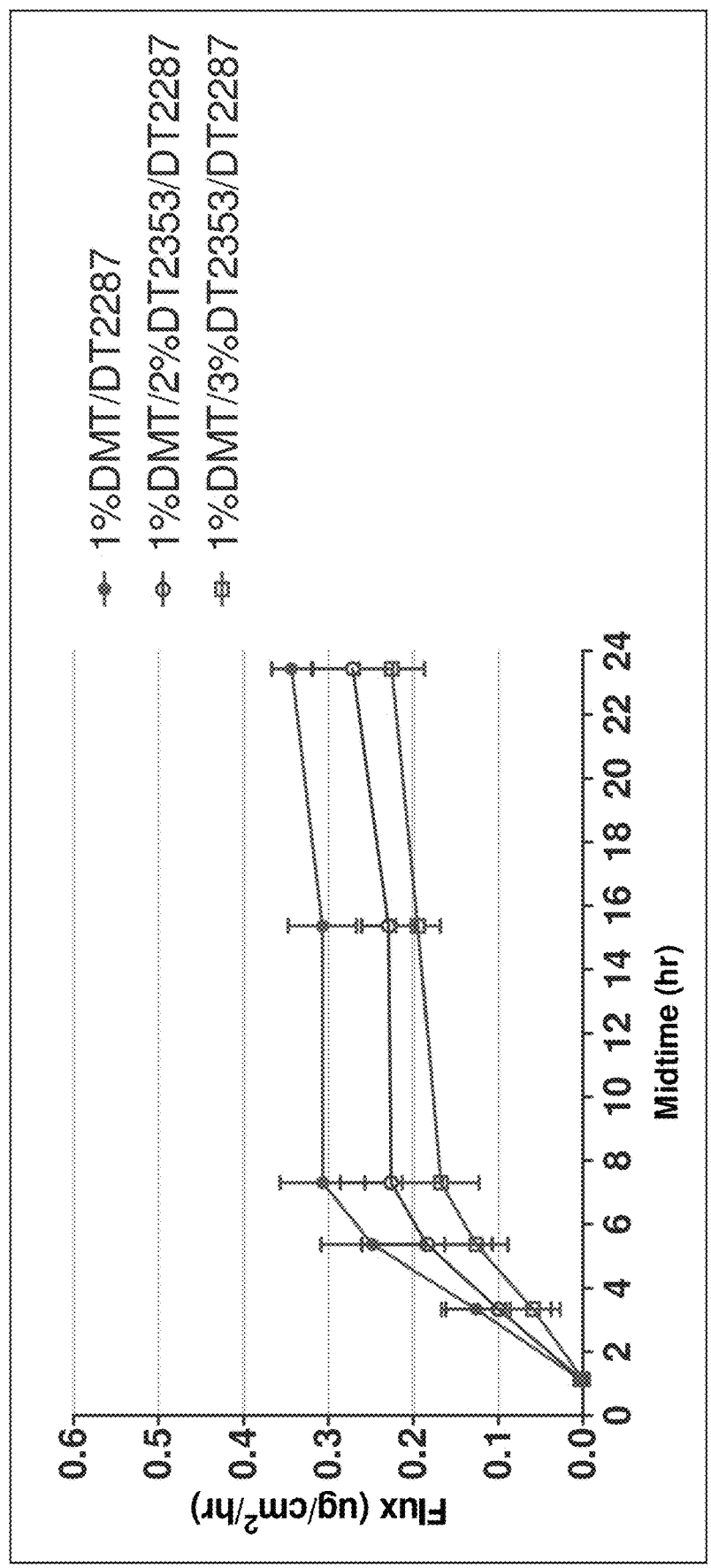
FIG. 14C shows an example of a plot of average dexmedetomidine flux as a function of transdermal delivery device application time for a dexmedetomidine transdermal composition having a hydroxyl functionalized acrylate adhesive containing vinyl acetate with a carboxylic acid functionalized acrylate adhesive according to one embodiment.

Another set of examples of dexmedetomidine transdermal formulation include transdermal compositions having 1% w/w dexmedetomidine with a solubilizer to improve physical stability of the composition. In these formulations, levulinic acid, PVP K90 and Duro-Tak 87-2353 were employed. The formulation compositions are shown in Tables 13, 14 and 15. In-vitro flux profiles for transdermal compositions having 1% dexmedetomidine with 0.3% and 0.6% levulinic acid are shown in FIG. 14(A). In-vitro flux profiles for transdermal compositions having 1% dexmedetomidine with 5% and 10% PVP K90 are shown in FIG. 14(B). In-vitro flux profiles for transdermal compositions having 1% dexmedetomidine with 2% or 3% Duro-Tak 387/87-2353 are shown in FIG. 14(C). From the in-vitro flux profiles, levulinic acid enhanced the permeation after application for 15 hr., PVP K90 delayed transdermal flux of dexmedetomidine whereas Duro-Tak 2353 slightly reduced transdermal flux.

TABLE 13

| Components | % w/w | |
|---|---|---|
| | Formulation 32 (1% DMT/ 0.3% LA/DT2287) | Formulation 33 (1% DMT/ 0.6% LA/DT2287) |
| Dexmedetomidine base | 1.00 | 1.00 |
| Levulinic acid | 0.30 | 0.60 |
| Pressure Sensitive Adhesive Duro-Tak 387/87-2287 | 98.70 | 98.40 |

TABLE 14

| Components | % w/w | |
|---|---|---|
| | Formulation 34 (1% DMT/5% PVP-K90/DT2287) | Formulation 35 (1% DMT/10% PVP-K90/DT2287) |
| Dexmedetomidine base | 1.00 | 1.00 |
| PVP K90 | 5.00 | 10.00 |
| Pressure Sensitive Adhesive Duro-Tak 387/87-2287 | 94.00 | 89.00 |

TABLE 15

| Components | % w/w | |
|---|---|---|
| | Formulation 36 (1% DMT/ 2% DT2353/DT2287) | Formulation 37 (1% DMT/ 3% DT2353/DT2287) |
| Dexmedetomidine base | 1.00 | 1.00 |
| Pressure Sensitive Adhesive Duro-Tak 387/87-2353 | 2.00 | 3.00 |
| Pressure Sensitive Adhesive Duro-Tak 387/87-2287 | 97.00 | 96.00 |

Example 10

In-Vitro Flux obtained from Dexmedetomidine Transdermal Composition Formulations in Duro-Tak 87-9301 Polymers Containing Levulinic Acid, Oleic Acid or Duro-Tak 387/87-2353

Figure 15:
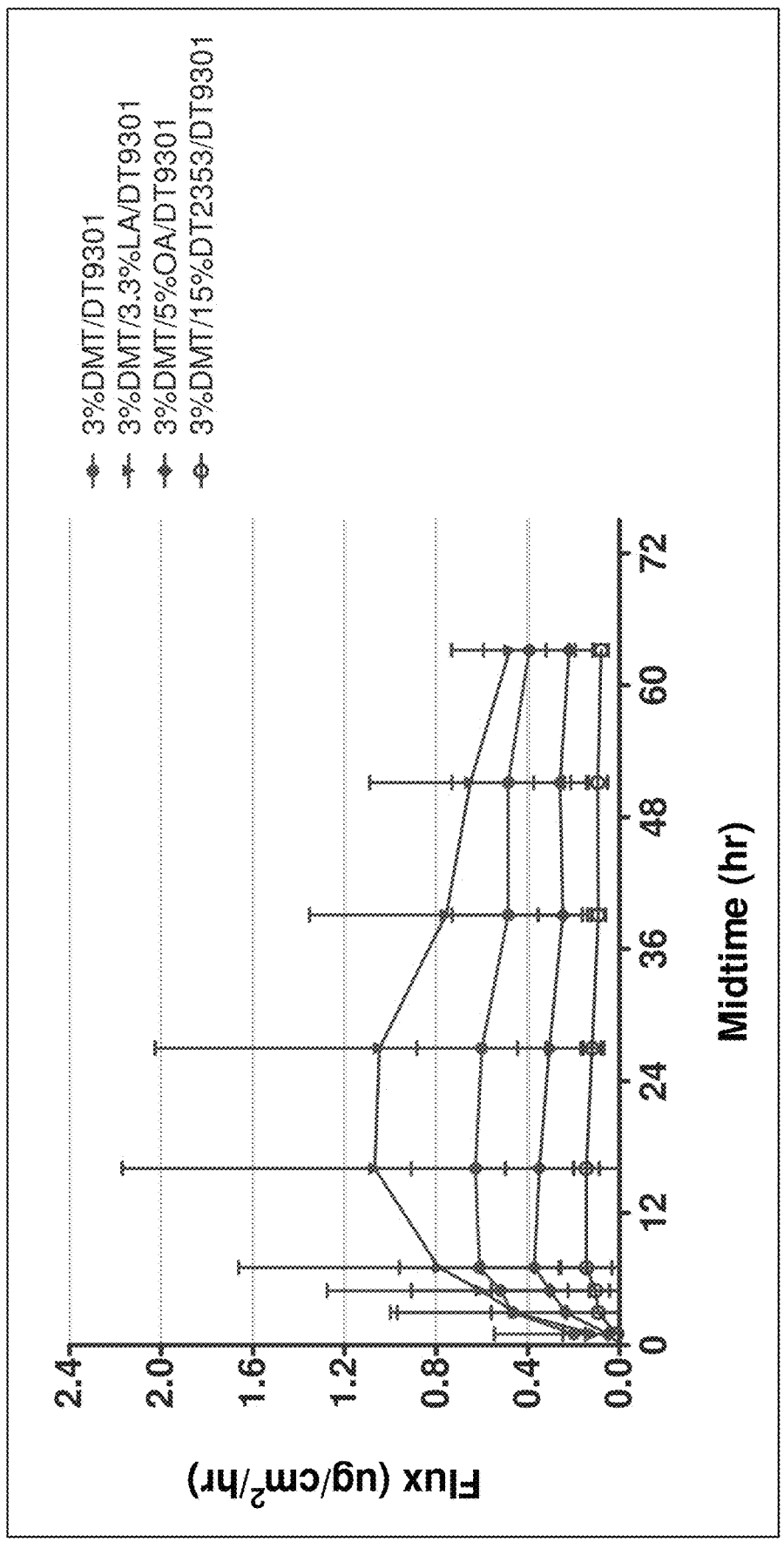
FIG. 15 shows an example of a plot of average dexmedetomidine flux as a function of transdermal delivery device application time for a dexmedetomidine transdermal composition having acrylate pressure sensitive adhesive in the absence and presence of levulinic acid, oleic acid or a carboxylic acid functionalized acrylate adhesive according to one embodiment.

Another set of examples of dexmedetomidine transdermal formulation include transdermal compositions having 3% w/w dexmedetomidine and non-functionalized acrylate polymer Duro-Tak 87-9301 in combination with 3.3% levulinic acid, 5% Oleic acid or 15% Duro-Tak 387/87-2353. The formulation compositions are shown in Table 16. In-vitro flux profiles for these formulations (Formulations 38, 39 and 40), compared with 3% dexmedetomidine in non-functionalized acrylate polymer Duro-Tak 87-9301 without additive (Formulation 7) are illustrated in FIG. 15. Compositions having just 3% dexmedetomidine and non-functionalized acrylate polymer Duro-Tak 87-9301 were supersaturated. Levulinic acid and oleic acid were used as a solubilizer and permeation enhancer and increased flux at the beginning of in-vitro flux, but declined with time. Like with the 1% dexmedetomidine compositions, Duro-Tak 87-2353 reduced flux.

TABLE 16

| Components | % w/w | | |
|---|---|---|---|
| | Formulation 38 (3% DMT/ 3.3% LA/ DT9301) | Formulation 39 (3% DMT/ 5% OA/ DT9301) | Formulation 40 (3% DMT/ 15% DT2353/ DT9301) |
| Dexmedetomidine base | 3.00 | 3.00 | 3.00 |
| Levulinic acid | 3.30 | 0.00 | 0.00 |
| Oleic acid | 0.00 | 5.00 | 0.00 |
| Pressure Sensitive Adhesive Duro-Tak 387/87-2353 | 0.00 | 0.00 | 15.00 |
| Pressure Sensitive Adhesive Duro-Tak 87-9301 | 93.70 | 92.00 | 82.00 |

Example 11

In-Vitro Permeation of Dexmedetomidine Obtained from 1%, 2%, 3% and 4% Dexmedetomidine in the Mixture of Adhesives (15% Duro-Tak2353 in Duro-Tak 2287)

Dexmedetomidine transdermal composition formulations containing the mixture of hydroxyl functionalized acrylate polymer (e.g., Duro-Tak 87-2287) and acid functionalized acrylate polymer (e.g., Duro-Tak 87-2353) are summarized in Table 17. Formulations 41 to 44 were prepared with different loadings of dexmedetomidine.

TABLE 17

| Components | % w/w | | | |
|---|---|---|---|---|
| | Formulation 41 (1% DMT/15% DT2353/DT2287) | Formulation 42 (2% DMT/15% DT2353/DT2287) | Formulation 43 (3% DMT/15% DT2353/DT2287) | Formulation 44 4% DMT/15% DT2353/ DT2287 |
| Dexmedetomidine base | 1.00 | 2.00 | 3.00 | 4.00 |
| Pressure Sensitive Adhesive Duro-Tak 2353 | 15.00 | 15.00 | 15.00 | 15.00 |

TABLE 17-continued

| | % w/w | | | |
|---|---|---|---|---|
| Components | Formulation 41 (1% DMT/15% DT2353/DT2287) | Formulation 42 (2% DMT/15% DT2353/DT2287 | Formulation 43 3% DMT/15% DT2353/DT2287 | Formulation 44 4% DMT/15% DT2353/ DT2287 |
| Pressure Sensitive Adhesive Duro-Tak 2287 | 84.00 | 83.00 | 82.00 | 81.00 |

Figure 16:
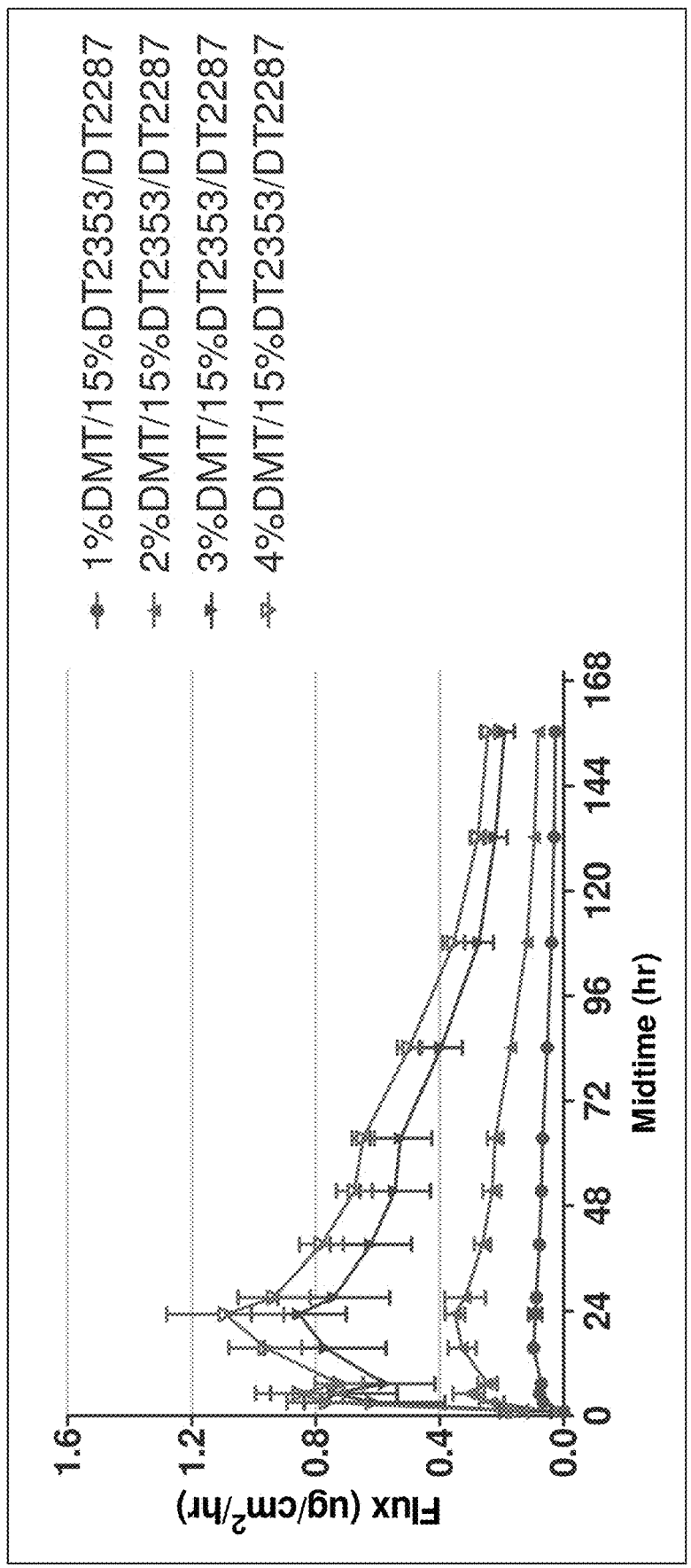
FIG. 16 shows an example of a plot of average dexmedetomidine flux as a function of transdermal delivery device application time for a dexmedetomidine transdermal composition having a hydroxyl functionalized acrylate adhesive containing vinyl acetate with a carboxylic acid functionalized acrylate adhesive according to another embodiment.

As depicted in FIG. 16, in-vitro flux of dexmedetomidine increased with increasing percent of dexmedetomidine loading.

Example 12

In-Vitro Permeation of Dexmedetomidine Obtained from Dexmedetomidine Formulations Containing Oleic Acid Another example of dexmedetomidine transdermal composition formulations is summarized in Table 18. In order to increase the solubility of dexmedetomidine in the hydroxyl functionalized acrylate polymer (e.g., Duro-Tak 87-2287), oleic acid was used. Formulations 45 to 47 were prepared with different loadings of oleic acid and dexmedetomidine.

TABLE 18

| | % w/w | | |
|---|---|---|---|
| Components | Formulation 45 (3% DMT/ 5% OA/DT2287) | Formulation 46 3% DMT/7% OA/ DT2287 | Formulation 47 3% DMT/5% OA/ DT2287 |
| Dexmedetomidine base | 3.00 | 3.00 | 4.00 |
| Oleic acid | 5.00 | 7.00 | 5.00 |
| Pressure Sensitive Adhesive Duro-Tak 2287 | 92.00 | 90.00 | 91.00 |

Figure 17:
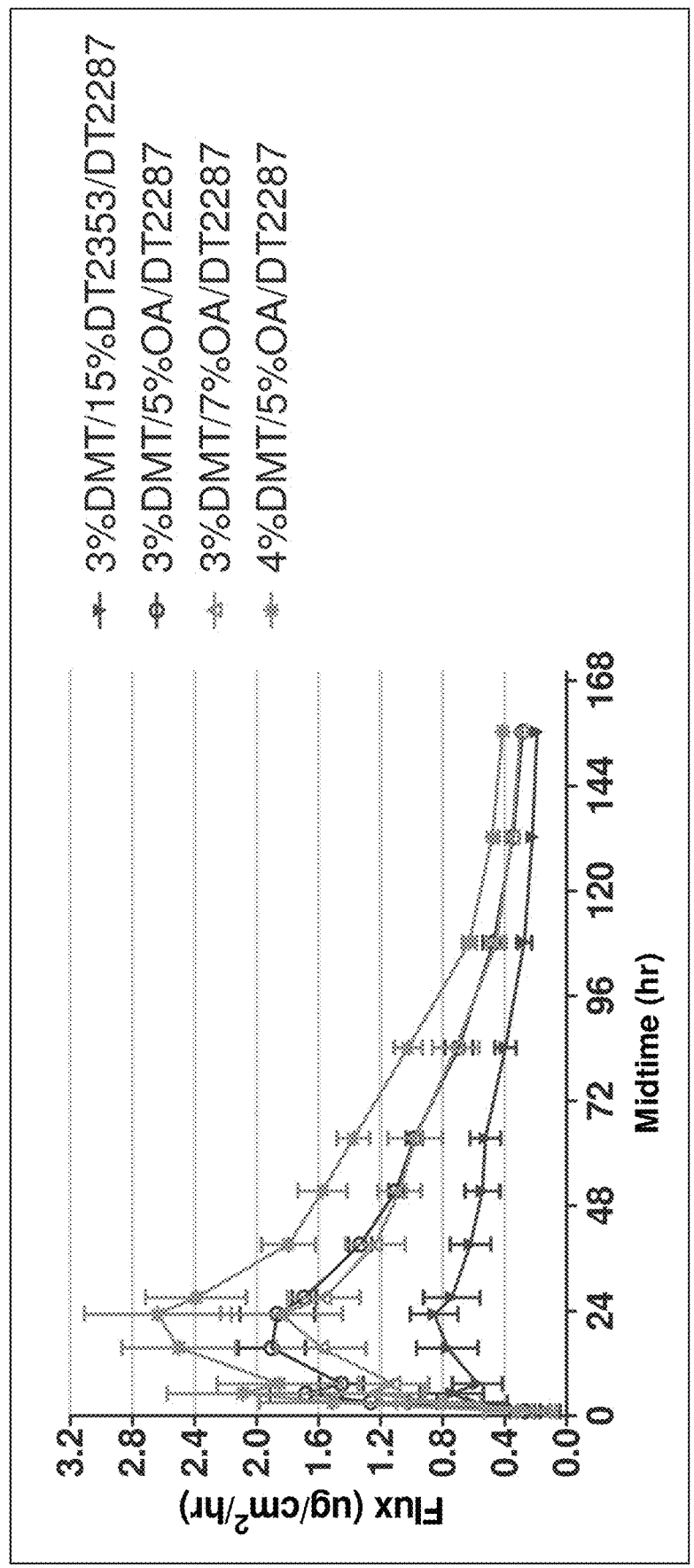
FIG. 17 shows an example of a plot of average dexmedetomidine flux as a function of transdermal delivery device application time for a dexmedetomidine transdermal composition having a hydroxyl functionalized acrylate adhesive containing vinyl acetate with oleic acid or a carboxylic acid functionalized acrylate adhesive according to another embodiment.

As depicted in FIG. 17, dexmedetomidine in formulations containing oleic acid has a higher flux than a dexmedetomidine composition (e.g., Formulation 43) which does not contain oleic acid. Oleic acid enhanced the permeation of dexmedetomidine through the skin. An increase of oleic acid from 5% to 7% (e.g. Formulation 46) did not show an enhancement effect as compared to the formulation containing 5% oleic acid (e.g. Formulation 45). This may be the result of the contribution of oleic acid in increasing in solubility of dexmedetomidine in the composition. A comparison of Formulation 45 and Formulation 47 shows that the in-vitro flux increases with increasing percent drug loading.

Example 13

In-Vitro Permeation of Dexmedetomidine Obtained from Dexmedetomidine Formulations Containing Levulinic Acid Dexmedetomidine transdermal formulations were also prepared with levulinic acid. The composition is shown in Table 19.

TABLE 19

| | % w/w | |
|---|---|---|
| Components | Formulation 48 (3% DMT/ 4% LA/DT2287) | Formulation 49 (4% DMT/4% LA/DT2287) |
| Dexmedetomidine base | 3.00 | 4.00 |
| Levulinic acid | 4.00 | 4.00 |
| Pressure Sensitive Adhesive Duro-Tak 2287 | 93.00 | 92.00 |

Figure 18:
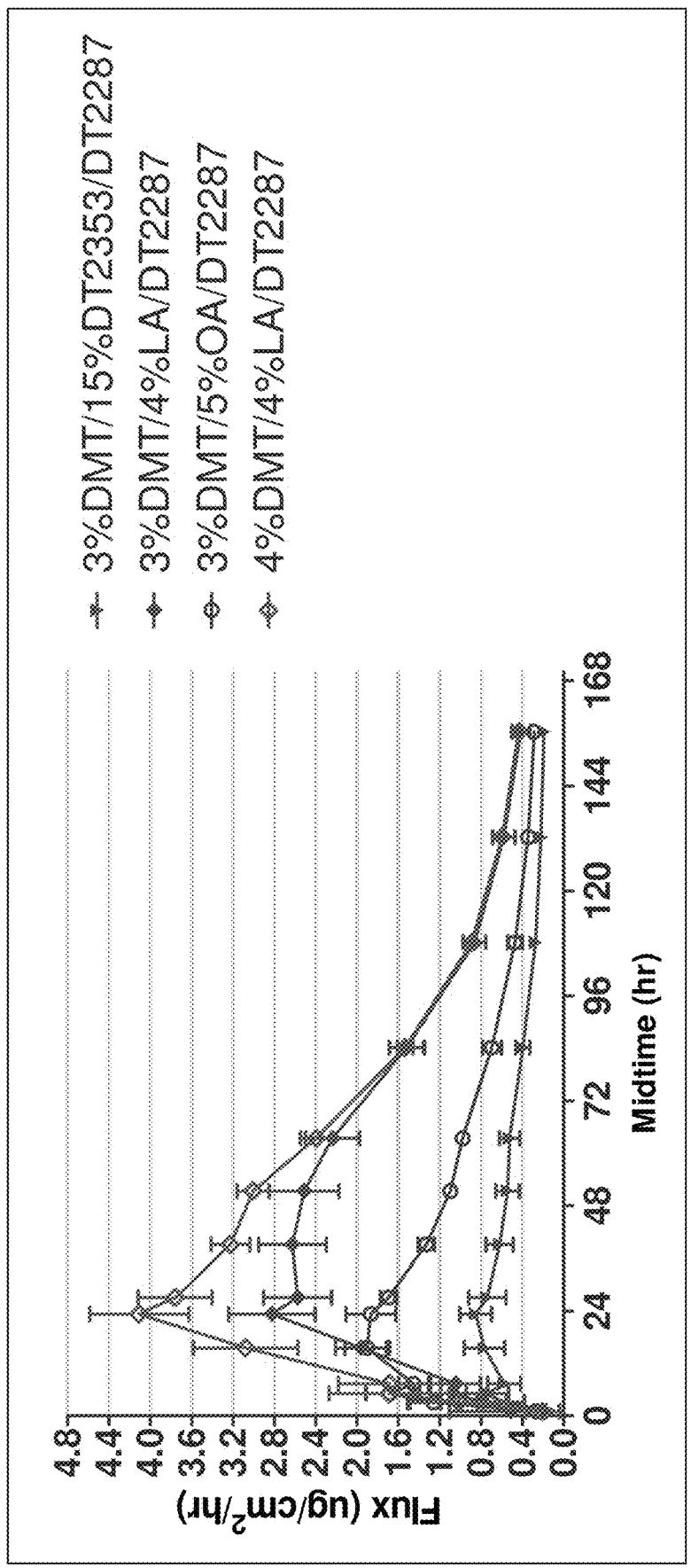
FIG. 18 shows an example of a plot of average dexmedetomidine flux as a function of transdermal delivery device application time for a dexmedetomidine transdermal composition having a hydroxyl functionalized acrylate adhesive containing vinyl acetate with solubility enhancers such as carboxylic acid functionalized acrylate adhesives, lauryl lactate or oleic acid according to another embodiment.

As shown in FIG. 18, in-vitro flux of dexmedetomidine in formulations containing levulinic acid (Formulations 48 and 49) increased with percent dexmedetomidine loading. The enhancement effect of levulinic acid on permeation of dexmedetomidine through the skin was higher than oleic acid.

The results of percent in-vitro penetration of dexmedetomidine in formulations 43, 45 and 48 relative to the amount of dexmedetomidine in the patch are summarized in Table 20. Formulations 45 and 48, which contain levulinic acid and oleic acid, demonstrate a substantial enhancement in permeation of dexmedetomidine under in-vitro condition.

TABLE 20

| Formulation No. | Formulation names | Amount of dexmedetomidine base in patch (µg) | % Permeation of dexmedetomidine base relative to the amount of drug in patch after 7 days | No. of replicates |
|---|---|---|---|---|
| Formulation 43 | 3% DMT/15% DT2353/DT2287 | 690 ± 27 | 18 ± 4 | 4 |
| Formulation 45 | 3% DMT/5% Oleic acid/DT2287 | 486 ± 11 | 52 ± 4 | 4 |
| Formulation 48 | 3% DMT/4% Levulinic acid/DT2287 | 573 ± 39 | 74 ± 5 | 5 |

The solubility of dexmedetomidine in hydroxyl functionalized acrylate polymer was less than 1%. In order to increase the dexmedetomidine, an acid functionalized acrylate polymer (e.g., Duro-Tak2353), oleic acid and levulinic acid were used. The solubility of dexmedetomidine in Duro-Tak2353, oleic acid and levulinic acid was about 10-15%, 40% and 60% respectively. The amount of acid added in the formulation was adjusted according to the solubility of each component in the formulation.

After preparation, the crystal presence was examined using microscope. Results obtained from this microscope examination indicated that all formulations (Formulations 41 to 48) did not contain crystals.

Example 14

In-Vitro Flux Obtained from Different Backings

Pressure-sensitive adhesives used in this example are polyisobutylene/polybutene (PIB/PB) adhesives. The PIB/PB adhesives are mixtures of high molecular weight PIB (5% Oppanol B100), low molecular weight PIB (25% Oppanol B12) and a polybutene tackifier, e.g., Indopol H1900 or Panalane H-300e (20%), in an organic solvent, e.g., heptane (50%). The combination was mixed for about 3 days, until the mixture was homogeneous. Example dexmedetomidine transdermal composition formulations are shown in Table 21. Same formulation was coated on release liner but laminated with three different backing materials: backing 1 has a MVTR value (g/m$^2$/24 hr) around 10, Backing 2 has a MVTR value around 50 (g/m$^2$/24 hr), and backing 3 has MVTR value around 150 (g/m$^2$/24 hr).

Figure 19:
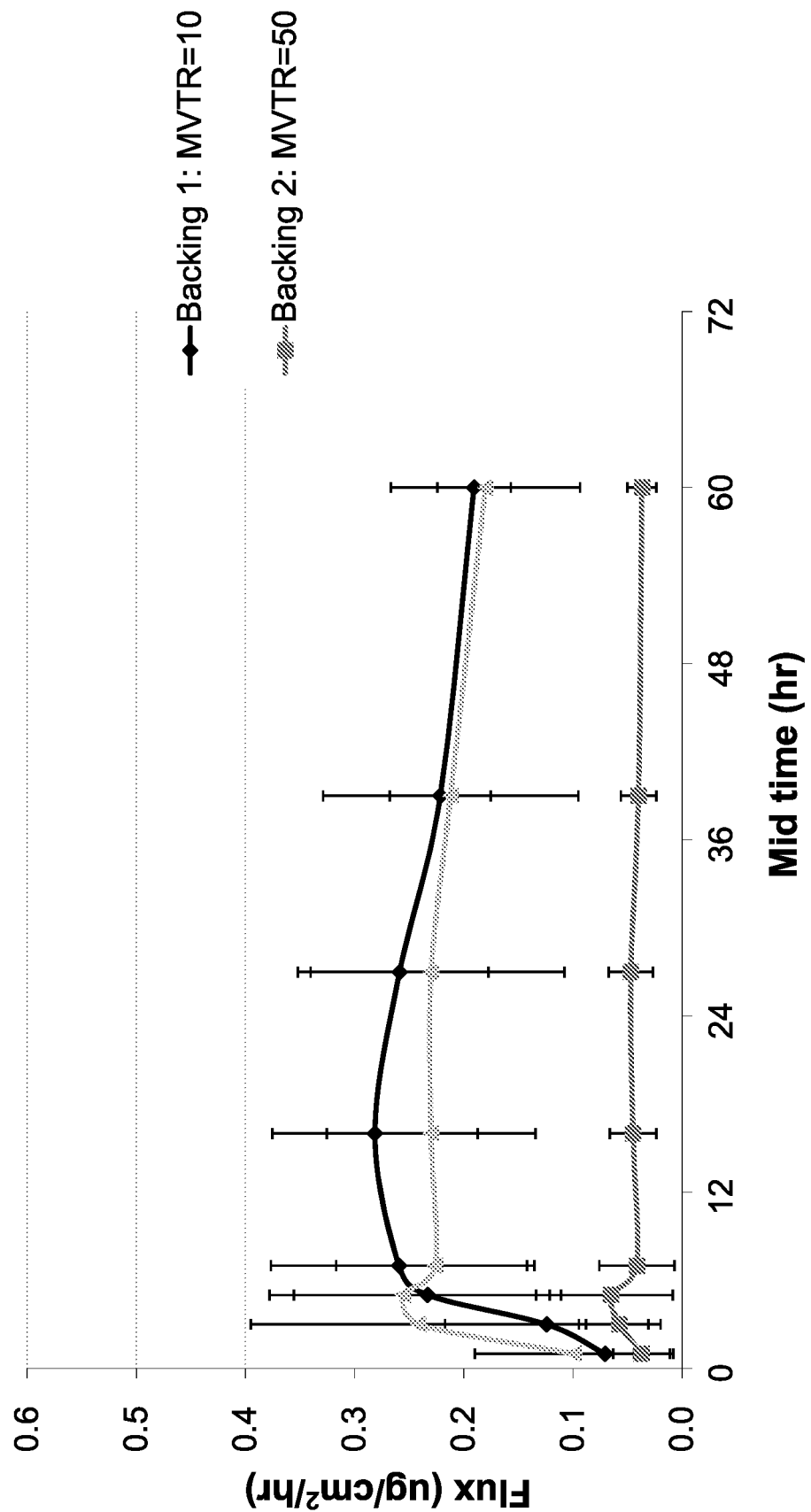
FIG. 19 shows the average dexmedetomidine in-vitro skin flux with respect to time from various formulations.

The average dexmedetomidine in-vitro skin flux with respect to time is illustrated in FIG. 19. As depicted in FIG. 19, dexmedetomidine in-vitro skin flux was similar for backing 1 and 2. But it is significantly lower with backing 3.

TABLE 21

| Components | % w/w |
| --- | --- |
| Dexmedetomidine | 1.00 |
| PVP-CLM | 20.00 |
| PIB/PB (Indopol H1900) | 79.00 |

Example 15

In-Vitro Flux Obtained from Formulations with Lauryl Lactate as Enhancer

Figure 20:
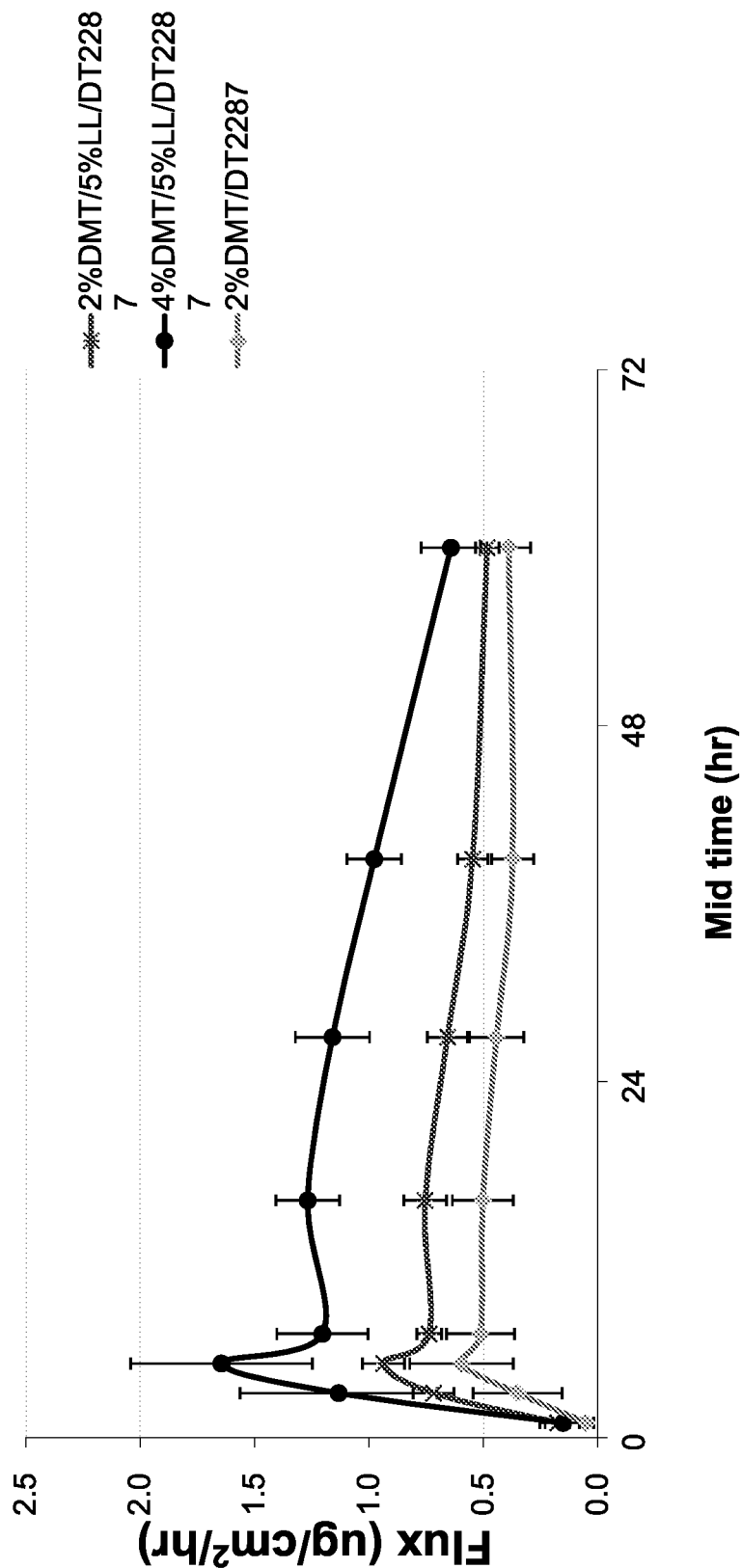
FIGS. 20 and 21 show the flux on two different skin samples from various formulations.
Figure 21:
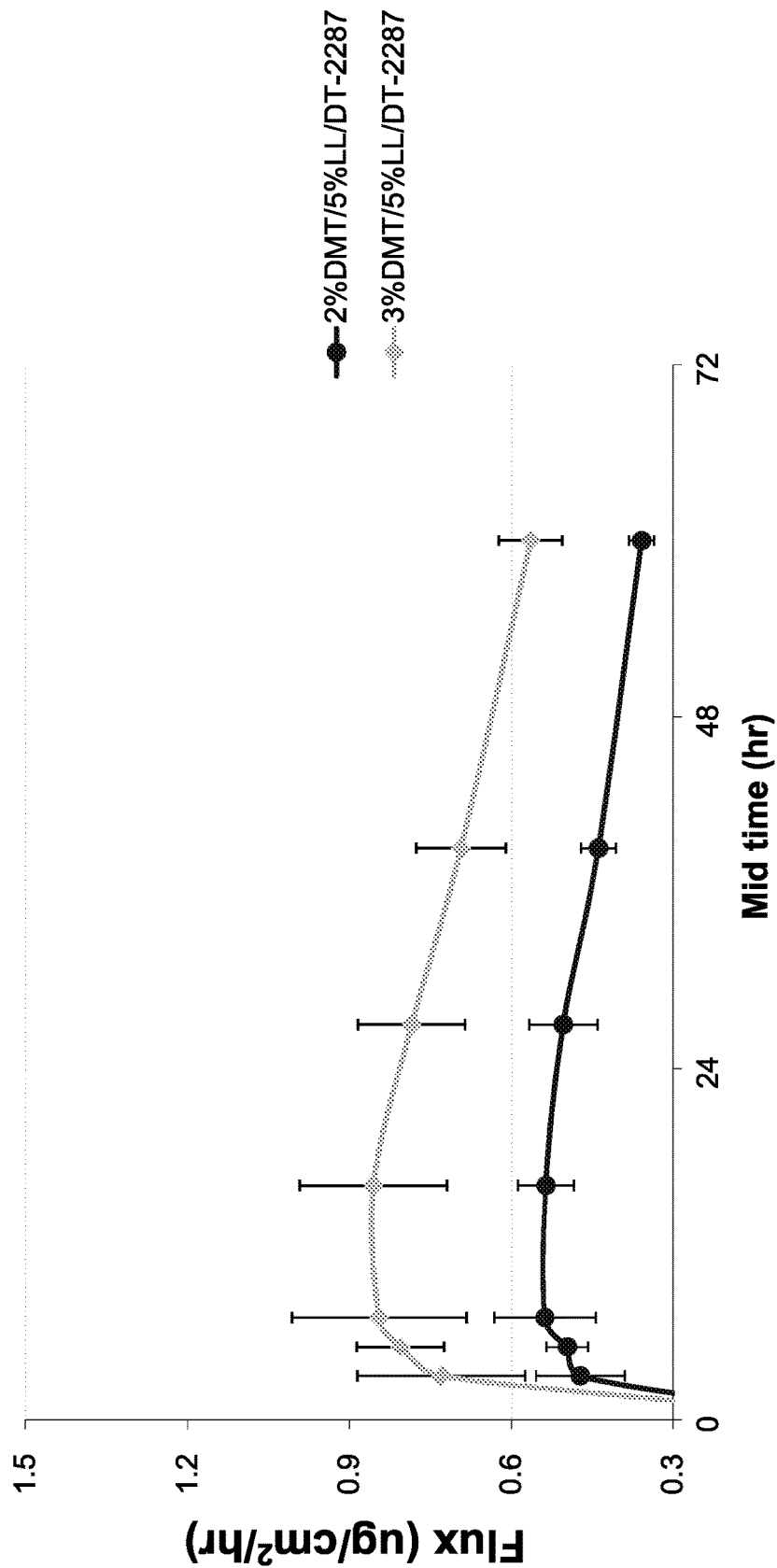

Another set of examples of dexmedetomidine transdermal formulation include transdermal compositions having 2-4% w/w dexmedetomidine with an enhancer to improve skin permeability. In these formulations, lauryl lactate (LL) and Duro-Tak 87-2287 were employed. The formulation compositions are shown in Table 22. In-vitro flux profiles for transdermal compositions. FIGS. 20 and 21 show the flux on two different skin samples. From the in-vitro flux profiles, LL shows its skin permeability enhancement effect. The flux is also proportional to API loading.

TABLE 22

| Components | % w/w | | | |
| --- | --- | --- | --- | --- |
| Dexmedetomidine base | 2 | 2 | 3 | 4 |
| Lauryl lactate | 0 | 5 | 5 | 5 |
| Pressure Sensitive Adhesive Duro-Tak 87-2287 | 98 | 93 | 92 | 91 |

The flux profile of all formulations (Formulations 41 to 48) showed a clear increasing trend in flux with time during the first 24 hours (FIGS. 16 to 18). This is followed by a gradual decrease in flux with time. As such, the increase in flux during the first 24 hours may, in certain instances, be useful for achieving a rapid higher initial therapeutic concentration in the body. Where there is a decrease in flux with time, the decrease in flux could be due to the crystallization of the drug in the adhesive induced by the absorbed water in the patch.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An extended release transdermal delivery device consisting of:
a single layer matrix dexmedetomidine composition, wherein the dexmedetomidine composition consists of:
dexmedetomidine in an amount of from 2% w/w to 3% w/w;
lauryl lactate in an amount of from 1% w/w to 5% w/w; and
an acrylate pressure sensitive adhesive with pendant hydroxyl functional groups; and
a backing layer,
wherein the single layer matrix dexmedetomidine composition is formulated to deliver a therapeutically effective amount of dexmedetomidine to a subject over an extended period of time.

2. The transdermal delivery device according to claim 1, wherein the single layer matrix is formulated to deliver a sedative amount of dexmedetomidine to a subject over an extended period of time.

3. The transdermal delivery device according to claim 1, wherein the single layer matrix is formulated to deliver dexmedetomidine to a subject for 6 hours or longer.

4. The transdermal delivery device according to claim 1, wherein the single layer matrix is formulated to deliver dexmedetomidine to a subject for 1 day or longer.

5. The transdermal delivery device according to claim 1, wherein the single layer matrix is formulated to deliver dexmedetomidine to a subject for 7 days or longer.

6. The transdermal delivery device according to claim 1, wherein the dexmedetomidine composition comprises a saturated amount of dexmedetomidine.

7. The transdermal delivery device according to claim 1, wherein the dexmedetomidine composition comprises a supersaturated amount of dexmedetomidine.

8. The transdermal delivery device according to claim 1, wherein the transdermal delivery device is configured to deliver a non-sedative amount of dexmedetomidine to a subject at a rate ranging from about 10 µg/day to about 1000 µg/day.

9. The transdermal delivery device according to claim 1, wherein the transdermal delivery device is configured to deliver 30% or more of the dexmedetomidine in the single layer matrix to the subject over an extended period of time.

10. The transdermal delivery device according to claim 1, wherein the pressure sensitive adhesive is a vinyl polymer.

11. The transdermal delivery device according to claim 1, wherein the pressure sensitive adhesive is an acrylate-vinyl acetate copolymer that lacks a crosslinker.

12. A method comprising applying to a skin surface of a non-sedated subject an extended release transdermal delivery device consisting of:
a single layer matrix dexmedetomidine composition, wherein the dexmedetomidine composition consists of:
dexmedetomidine in an amount of from 2% w/w to 3% w/w;
lauryl lactate in an amount of from 1% w/w to 5% w/w; and
an acrylate pressure sensitive adhesive with pendant hydroxyl functional groups; and
a backing layer,
wherein the single layer matrix dexmedetomidine composition is formulated to deliver a therapeutically effective amount of dexmedetomidine to a subject over an extended period of time.

13. The method according to claim 12, wherein the method comprises delivering dexmedetomidine to the subject in manner sufficient to maintain a Ramsay score of not greater than 3 in the subject.

14. A kit comprising:
two or more transdermal delivery devices, wherein each transdermal delivery device consists of:
a single layer matrix dexmedetomidine composition, wherein the dexmedetomidine composition consists of:
dexmedetomidine in an amount of from 2% w/w to 3% w/w;
lauryl lactate in an amount of from 1% w/w to 5% w/w; and
an acrylate pressure sensitive adhesive with pendant hydroxyl functional groups; and
a backing layer,
wherein the single layer matrix dexmedetomidine composition is formulated to deliver a therapeutically effective amount of dexmedetomidine to a subject over an extended period of time.

15. The transdermal delivery device according to claim 1, wherein the acrylate pressure sensitive adhesive is an acrylate copolymer having a hydroxyl-functionalized acrylate monomer selected from the group consisting of ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate and tridecyl methacrylate.

16. The transdermal delivery device according to claim 15, wherein the acrylate pressure sensitive adhesive is an acrylate copolymer having hydroxyl-functionalized ethyl acrylate.

17. The transdermal delivery device according to claim 1, wherein the acrylate pressure sensitive adhesive is an acrylate copolymer having 2-ethylhexyl acrylate.

18. The transdermal delivery device according to claim 1, wherein the acrylate pressure sensitive adhesive is an acrylate copolymer having butyl acrylate.

19. The transdermal delivery device according to claim 1, wherein the dexmedetomidine composition is configured to deliver dexmedetomidine to a subject at a flux rate of from 0.5 µg/cm$^2$/hr to 2.0 µg/cm$^2$/hr.

20. The transdermal delivery device according to claim 1, wherein the acrylate pressure sensitive adhesive is a polymer formed from vinyl acetate, ethylhexyl acrylate and hydroxyl-functionalized ethyl acrylate.

21. The transdermal delivery device according to claim 20, wherein the lauryl lactate is present in an amount sufficient to provide for substantially the same transdermal delivery profile of dexmedetomidine over an extended period of time and increased transdermal dexmedetomidine flux as compared to a transdermal delivery device consisting of a backing layer in contact with a dexmedetomidine composition that consists of dexmedetomidine and an acrylate pressure sensitive adhesive having pendant hydroxyl functional groups.

* * * * *